United States Patent [19]

Matsushima et al.

[11] Patent Number: 5,994,524

[45] Date of Patent: *Nov. 30, 1999

[54] POLYNUCLEOTIDES WHICH ENCODE RESHAPED IL-8-SPECIFIC ANTIBODIES AND METHODS TO PRODUCE THE SAME

[75] Inventors: Kouji Matsushima, Kanazawa; Yoshihiro Matsumoto, Gotenba; Yoshiki Yamada, Gotenba; Koh Sato, Gotenba; Masayuki Tsuchiya, Gotenba; Tatsumi Yamazaki, Gotenba, all of Japan

[73] Assignee: Chugai Seiyaku Kabushiki Kaisha, Tokyo, Japan

[*] Notice: This patent is subject to a terminal disclaimer.

[21] Appl. No.: 08/765,783

[22] PCT Filed: Jul. 12, 1995

[86] PCT No.: PCT/JP95/01396

§ 371 Date: Mar. 7, 1997

§ 102(e) Date: Mar. 7, 1997

[87] PCT Pub. No.: WO97/02576

PCT Pub. Date: Feb. 1, 1996

[30] Foreign Application Priority Data

Jul. 13, 1994 [JP] Japan .................................. 6-161481
Nov. 24, 1994 [JP] Japan .................................. 6-289951
Dec. 14, 1994 [JP] Japan .................................. 6-310785

[51] Int. Cl.$^6$ .............................. C12N 15/13; C12N 5/10; C07K 21/04; C07K 16/24
[52] U.S. Cl. .................... 536/23.53; 435/69.1; 435/69.6; 435/69.7; 435/70.21; 435/455; 435/471; 435/326; 435/335; 530/387.3; 530/388.23; 536/23.1; 536/23.4; 536/23.5
[58] Field of Search .................... 435/69.1, 69.7, 435/70.21, 326; 530/387.3, 388.23; 536/23.1, 23.53

[56] References Cited

U.S. PATENT DOCUMENTS 5,530,101   6/1996   Queen et al. .

OTHER PUBLICATIONS

Ko, Yue–chau, et al., "A Sensitive enzyme–linked immunosorbent assay for human interleukin–8" *J Immunol Methods*, 149:227–235 (1992).

Osamu Kanemitsu, "Antibody Engineering" 1st. Edit (Tokyo) *Chijin Shokan K..K.* pp. 195–234 (1995).

Riechmann, L. et al., "Reshaping Human antibodies for therapy" *Nature* 332:323–327 (1988).

Buluwela, L. et al., "The use of chromosomal translocations to study human immunoglobulin gene organization: mapping $D_H$ segments within 35kb of $C\mu$ gene and identification of a new $D_H$ locus" *The EMBO Journal*, 7:2003–2010 (1988).

Sanz, I. et al., "$V_H$ Sequence of a human anti–Sm autoantibody", *J. Immunol.* 142:883–887 (1989).

*Primary Examiner*—Christina Y. Chan
*Assistant Examiner*—Phillip Gambel
*Attorney, Agent, or Firm*—Morrison & Foerster

[57] ABSTRACT

The present invention discloses a reshaped human antibody against human IL-8 comprising:

(A) L chains each comprising:
(1) a human L chain C region; and,
(2) an L chain V region comprising a human L chain FR, and an L chain CDR of mouse monoclonal antibody against human IL-8; and, (B) H chains each comprising:
(1) a human H chain C region; and,
(2) an H chain V region comprising a human H chain FR, and an H chain CDR of mouse monoclonal antibody against human IL-8. Since the majority of this reshaped human antibody originates in human antibody and the CDR has low antigenicity, the reshaped human antibody of the present invention has low antigenicity to humans, and can therefore be expected to be useful in medical treatment. The present invention further discloses polynucleotides which encode reshaped antibodies against IL-8, as well as host cells and methods to produce these antibodies.

30 Claims, 8 Drawing Sheets

Fig. 3
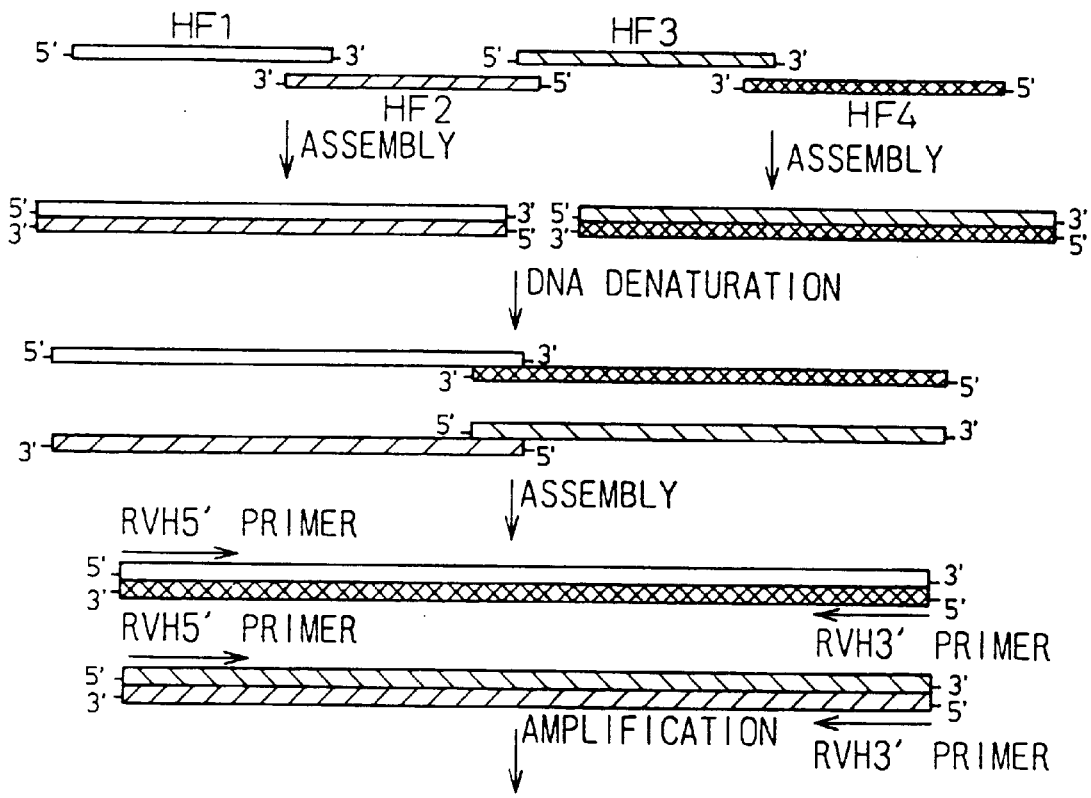
A
OLIGONUCLEOTIDE SYNTHESIS
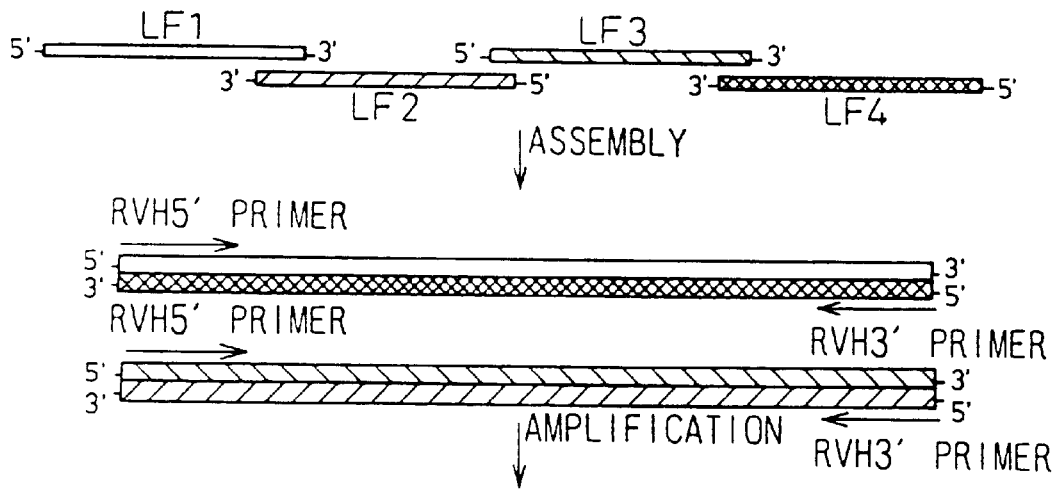
B
OLIGONUCLEOTIDE SYNTHESIS

POLYNUCLEOTIDES WHICH ENCODE RESHAPED IL-8-SPECIFIC ANTIBODIES AND METHODS TO PRODUCE THE SAME

TECHNICAL FIELD

The present invention relates to the complementarity determining regions (CDRs) and the variable regions (V regions) of mouse monoclonal antibody against human interleukin-8 (IL-8), to human/mouse chimeric antibody against human IL-8, as well as to a reshaped human antibody wherein the complementarity determining regions of the human light chain (L chain) variable region and the human heavy chain (H chain) variable region are substituted with the CDR of mouse monoclonal antibody against human IL-8. Moreover, the present invention provides DNAs that code for the above-mentioned antibody and its portions. The present invention also relates to a vector that contains the above-mentioned DNA, and more particularly, to an expression vector and a host transformed with said vector. Moreover, the present invention provides a process for producing reshaped human antibody against human IL-8 as well as a process for producing a chimeric antibody against human IL-8.

BACKGROUND ART

Interleukin-8 (IL-8) was discovered in the culture supernatant of monocytes stimulated with lipopolysaccharide (LPS), and is a chemokine known also as monocyte-derived neutrophil chemotactic factor (MDNCF) or neutrophil activating protein-1 (NAP-1). IL-8 is produced by various cells, acts on polymorphonuclear leukocytes and lymphocytes, and possesses activity that causes chemotaxis along its concentration gradient. In addition, not only does it induce chemotaxis in neutrophils, but it also activates neutrophilic functions such as degranulation, the release of superoxide, and the promotion of adhesion to endothelial cells.

In inflammatory diseases, and more specifically in respiratory diseases such as pulmonary cystic fibrosis, idiopathic pulmonary fibrosis, adult respiratory distress syndrome, sarcoidosis and empyema, as well as in skin diseases such as psoriasis, and in chronic rheumatoid arthritis, Crohn's disease and ulcerative colitis, leukocyte infiltration is observed pathologically at the inflamed site of these diseases. In addition, IL-8 is detected in test samples from patients with these diseases, suggesting that IL-8 may play a central role in inflammation. (McElvaney, N. G. et al., J. Clin. Invest., 90, 1296–1301, 1992; Lynch III, J. P. et al., Am. Rev. Respir. Dis., 145, 1433–1439, 1992; Donnelly, S. C. et al., Lancet, 341, 643–647, 1993; Car, B. D. et al., Am. J. Respir. Crit. Care Med., 149, 655–659, 1994; Antony, V. B. et al., J. Immunol., 151, 7216–7223, 1993; Takematsu, H. et al., Arch. Dermatol., 129, 74–80, 1993; Brennan, F. M. et al., Eur. J. Immunol., 20, 2141–2144, 1990; Izzo, R. S. et al., Scand. J. Gastroenterol., 28, 296–300, 1993; Izzo, R. S. et al., Am. J. Gastroenterol., 87, 1447–1452, 1992).

Subsequence to immunizing mice with human IL-8 as antigen, Ko, Y-C. et al. prepared the mouse monoclonal antibody WS-4 that binds to human IL-8 and inhibits the binding of human IL-8 to neutrophils as a result of that binding, namely that neutralizes the biological activity possessed by human IL-8. It has been clearly shown that the isotypes of mouse monoclonal antibody WS-4 consist of a κ-type L chain and a Cγ1-type H chain (J. Immunol. Methods, 149, 227–235, 1992).

Known examples of antibodies against human IL-8 other than WS-4 include A.5.12.14 (Boylan, A. M. et al., J. Clin. Invest., 89, 1257–1267, 1992), the anti-Pep-1 antibody and anti-Pep-3 antibody disclosed in International Patent Application No. WO92–04372, and DM/C7 (Mulligan, M. S. et al., J. Immunol., 150, 5585–5595, 1993).

It was also found by administration of the mouse monoclonal antibody WS-4 into experimental models using rabbits that neutrophil infiltration is inhibited in pulmonary ischemic and reperfusion injury (Sekido, N. et al., Nature, 365, 654–657, 1993), LPS-induced dermatitis (Harada, A. et al., Internatl. Immunol., 5, 681–690, 1993) and LPS- or interleukin-1 (IL-1)-induced arthritis (Akahoshi, T. et al., Lymphokine Cytokine Res., 13, 113–116, 1994).

A homologue of human IL-8 exists in rabbits, and is referred to as rabbit IL-8. Since it has been clearly shown that the mouse monoclonal antibody WS-4 cross-reacts with rabbit IL-8, and that the antibody inhibits binding of rabbit IL-8 to rabbit neutrophils (Harada, A. et al., Internatl. Immunol., 5, 681–690, 1993), these findings suggest that anti-human IL-8 antibody would be useful as a therapeutic agent for the treatment of inflammatory diseases in humans.

Monoclonal antibodies originating in mammals other than humans exhibit a high degree of immunogenicity (also referred to as antigenicity) in humans. For this reason, even if mouse antibody is administered to humans, as a result of its being metabolized as a foreign substance, the half life of mouse antibody in humans is relatively short, thus preventing its anticipated effects from being adequately demonstrated. Moreover, human anti-mouse antibody that is produced in response to administered mouse antibody causes an immune response that is both uncomfortable and dangerous for the patient, examples of which include serum sickness or other allergic response. For this reason, mouse antibody cannot be administered frequently to humans.

In order to resolve these problems, a process for producing a humanized antibody was developed. Mouse antibody can be humanized by two methods. The simpler method involves producing a chimeric antibody in which the variable region (V region) is derived from the original mouse monoclonal antibody, and the constant region (C region) is derived from a suitable human antibody. Since the resulting chimeric antibody contains the variable region of the mouse antibody in its complete form, it has identical specificity to the original mouse antibody, and can be expected to bind to antigen.

Moreover, in the chimeric antibody, since the proportion of protein sequences derived from an animal other than human is substantially reduced in comparison to the original mouse antibody, it is predicted to have less immunogenicity in comparison to the original mouse antibody. Although the chimeric antibody binds well to antigen and has low immunogenicity, there is still the possibility of an immune response to the mouse variable region occurring, however (LoBuglio, A. F. et al., Proc. Natl. Acad. Sci. USA, 86, 4220–4224, 1989).

Although the second method for humanizing mouse antibody is more complex, the latent immunogenicity of the mouse antibody is reduced considerably. In this method, only the complementarity determining region (CDR) is grafted from the variable region of mouse antibody onto the human variable region to create a reshaped human variable region. However, in order to approximate more closely the structure of the CDR of the reshaped human variable region to the structure of the original mouse antibody, there are cases in which it may be necessary to graft a portion of the protein sequence of the framework region (FR) supporting the CDR from the variable region of the mouse antibody to the human variable region.

Next, these reshaped human variable regions are linked to the human constant region. Those portions derived from non-human protein sequences consist only of the CDR and a very slight portion of the FR in the humanized antibody. CDR is composed of hyper-variable protein sequences, and these do not exhibit species specificity. For this reason, the reshaped human antibody that contains the mouse CDRs ought not to have immunogenicity stronger than that of a natural human antibody containing human CDRs.

Additional details regarding reshaped human antibodies can be found by referring to Riechmann, L. et al., Nature, 332, 323–327, 1988; Verhoeyen, M. et al., Science, 239, 1534–1536, 1988; Kettleborough, C. A. et al., Protein Eng., 4, 773–783, 1991; Maeda, H. et al., Hum. Antibodies Hybridomas, 2, 124–134, 1991; Gorman, S. D. et al., Proc. Natl. Acad. Sci. USA, 88, 4181–4185, 1991; Tempest, P. R. et al., Bio/Technology, 9, 266–271, 1991; Co, M. S. et al., Proc. Natl. Acad. Sci. USA, 88, 2869–2873, 1991; Carter, P. et al., Proc. Natl. Acad. Sci. USA, 89, 4285–4289, 1992; Co, M. S. et al., J. Immunol., 148, 1149–1154, 1992; and, Sato, K. et al., Cancer Res., 53, 851–856, 1993.

DISCLOSURE OF THE INVENTION

As stated above, although reshaped human antibodies are predicted to be useful for the purpose of therapy, there are no known reshaped human antibodies against human IL-8. Moreover, there are no standard processes that can be applied universally to an arbitrary antibody for producing reshaped human antibody. Thus, various contrivances are necessary to create a reshaped human antibody that exhibits sufficient binding activity and/or neutralizing activity with respect to a specific antigen (for example, Sato, K. et al., Cancer Res., 53, 851–856, 1993). The present invention provides an antibody against human IL-8 having a low degree of immunogenicity.

The present invention provides a reshaped human antibody against human IL-8. The present invention also provides a human/mouse chimeric antibody that is useful in the production process of said reshaped human antibody. Moreover, the present invention also provides a fragment of reshaped human antibody. In addition, the present invention provides an expression system for producing chimeric antibody and reshaped human antibody and fragments thereof. Moreover, the present invention also provides a process for producing chimeric antibody against human IL-8 and fragments thereof, as well as a process for producing reshaped human antibody against human IL-8 and fragments thereof.

More specifically, the present invention provides:
(1) an L chain V region of mouse monoclonal antibody against human IL-8; and,
(2) an H chain V region of mouse monoclonal antibody against human IL-8.

Moreover, the present invention provides:
(1) an L chain comprising a human L chain C region, and an L chain V region of mouse monoclonal antibody against human IL-8; and,
(2) an H chain comprising a human H chain C region, and an H chain V region of mouse monoclonal antibody against human IL-8.

Moreover, the present invention also provides chimeric antibody against human IL-8 comprising:
(1) L chains each comprising a human L chain C region, and an L chain V region of mouse monoclonal antibody against human IL-8; and,
(2) H chains each comprising a human H chain C region, and an H chain V region of mouse monoclonal antibody against human IL-8.

Moreover, the present invention provides:
(1) an L chain V region of mouse monoclonal antibody WS-4 against human IL-8; and,
(2) an H chain V region of mouse monoclonal antibody WS-4 against human IL-8.

Moreover, the present invention also provides:
(1) an L chain comprising a human L chain C region, and an L chain V region of mouse monoclonal antibody WS-4 against human IL-8; and,
(2) an H chain comprising a human H chain C region, and an H chain V region of mouse monoclonal antibody WS-4 against human IL-8.

In addition, the present invention provides chimeric antibody against human IL-8 comprising:
(1) L chains each comprising a human L chain C region, and an L chain V region of mouse monoclonal antibody WS-4 against human IL-8; and,
(2) H chains each comprising a human H chain C region, and an H chain V region of mouse monoclonal antibody WS-4 against human IL-8.

Moreover, the present invention provides:
(1) CDR of an L chain V region of monoclonal antibody against human IL-8; and,
(2) CDR of an H chain V region of monoclonal antibody against human IL-8.

Moreover, the present invention also provides:
(1) CDR of an L chain V region of mouse monoclonal antibody against human IL-8; and,
(2) CDR of an H chain V region of mouse monoclonal antibody against human IL-8.

Moreover, the present invention also provides a reshaped human L chain V region of an antibody against human IL-8 comprising:
(1) framework regions (FRs) of a human L chain V region; and,
(2) CDRs of an L chain V region of mouse monoclonal antibody against human IL-8;
as well as a reshaped human H chain V region of antibody against human IL-8 comprising:
(1) FRs of a human H chain V region; and,
(2) CDRs of an H chain V region of mouse monoclonal antibody against human IL-8.

Moreover, the present invention provides a reshaped human L chain of antibody against human IL-8 comprising:
(1) a human L chain C region; and,
(2) an L chain V region comprising human L chain FRs and L chain CDRs of mouse monoclonal antibody against human IL-8;
as well as a reshaped human H chain of antibody against human IL-8 comprising:
(1) a human H chain C region; and,
(2) an H chain V region comprising human H chain FRs and H chain CDRs of mouse monoclonal antibody against human IL-8.

In addition, the present invention also provides reshaped human antibody against human IL-8 comprising:
(A) L chains each comprising:
(1) a human L chain C region; and,
(2) an L chain V region comprising FRs of a human L chain, and CDRs of an L chain of mouse monoclonal antibody against human IL-8; as well as
(B) H chains each comprising:
(1) a human H chain C region; and,.
(2) an H chain V region comprising FRs of a human H chain, and CDRs of an H chain of mouse monoclonal antibody against human IL-8.

More specifically, the present invention provides:

(1) CDRs of an L chain V region of mouse monoclonal antibody WS-4 against human IL-8 having the following sequences or a portion thereof:
CDR1: Arg Ala Ser Glu Ile Ile Tyr Ser Tyr Leu Ala (SEQ ID NO:81)
CDR2: Asn Ala Lys Thr Leu Ala Asp (SEQ ID NO:82)
CDR3: Gln His His Phe Gly Phe Pro Arg Thr (SEQ ID NO:83)
as well as (2) CDRs of an H chain V region of mouse monoclonal antibody WS-4 against human IL-8 having the following sequences or a portion thereof:
CDR1: Asp Tyr Tyr Leu Ser (SEQ ID NO:84)
CDR2: Leu Ile Arg Asn Lys Ala Asn Gly Tyr Thr Arg Glu Tyr Ser Ala Ser Val Lys Gly (SEQ ID NO:85)
CDR3: Glu Asn Tyr Arg Tyr Asp Val Glu Leu Ala Tyr (SEQ ID NO:86)

Moreover, the present invention provides a reshaped human L chain V region of antibody against human IL-8 comprising:
(1) framework regions (FRs) of a human L chain V region; and,
(2) CDRs of an L chain V region of mouse monoclonal antibody WS-4 against human IL-8; as well as
a reshaped human H chain V region of antibody against human IL-8 comprising:
(1) FRs of a human H chain V region; and,
(2) CDRs of an H chain V region of monoclonal antibody WS-4 against human IL-8.

Moreover, the present invention provides a reshaped human L chain of antibody against human IL-8 comprising:
(1) a human L chain C region; and,
(2) an L chain V region comprising FRs of a human L chain, and CDRs of an L chain of mouse monoclonal antibody WS-4 against human IL-8; as well as
a reshaped human H chain of antibody against human IL-8 comprising:
(1) a human H chain C region; and,
(2) an H chain V region comprising FRs of a human H chain, and CDRs of an H chain of monoclonal antibody WS-4 against human IL-8.

In addition, the present invention also provides a reshaped human antibody against human IL-8 comprising:
(A) L chains each comprising:
(1) a human L chain C region; and,
(2) an L chain V region comprising FRs of a human L chain and CDRs of an L chain of mouse monoclonal antibody WS-4 against human IL-8; and
(B) H chains each comprising:
(1) a human H chain C region; and,
(2) an H chain V region comprising FRs of a human H chain and CDRs of an H chain of mouse monoclonal antibody WS-4 against human IL-8.

Examples of the above-mentioned FRs of a human L chain include those having the following amino acid sequences or a portion thereof:
FR1: Asp Ile Gln Met Thr Gln Ser Pro Ser Ser Leu Ser Ala Ser Val Gly Asp Arg Val Thr Ile Thr Cys (SEQ ID NO:87)
FR2: Trp Tyr Gln Gln Lys Pro Gly Lys Ala Pro Lys Leu Leu Ile Tyr (SEQ ID NO:88)
FR3: Gly Val Pro Ser Arg Phe Ser Gly Ser Gly Ser Gly Thr Asp Phe Thr Phe Thr Ile Ser Ser Leu Gln Pro Glu Asp Ile Ala Thr Tyr Tyr Cys (SEQ ID NO:89)
FR4: Phe Gly Gln Gly Thr Lys Val Glu Ile Lys (SEQ ID NO:90)

or,
FR1: Asp Ile Gln Met Thr Gln Ser Pro Ser Ser Leu Ser Ala Ser Val Gly Asp Arg Val Thr Ile Thr Cys (SEQ ID NO:87)
FR2: Trp Tyr Gln Gln Lys Pro Gly Lys Ala Pro Lys Leu Leu Ile Tyr (SEQ ID NO:88)
FR3: Gly Val Pro Ser Arg Phe Ser Gly Ser Gly Ser Gly Thr Asp Tyr Thr Phe Thr Ile Ser Ser Leu Gln Pro Glu Asp Ile Ala Thr Tyr Tyr Cys (SEQ ID NO:91)
FR4: Phe Gly Gln Gly Thr Lys Val Glu Ile Lys (SEQ ID NO:90)

Examples of the above-mentioned FRs of a human H chain include those having the following amino acid sequences or a portion thereof:
FR1: Glu Val Gln Leu Leu Glu Ser Gly Gly Gly Leu Val Gln Pro Gly Gly Ser Leu Arg Leu Ser Cys Ala Ala Ser Gly Phe Thr Phe Ser (SEQ ID NO:92)
FR2: Trp Val Arg Gln Ala Gln Gly Lys Gly Leu Glu Leu Val Gly (SEQ ID NO:93)
FR3: Arg Leu Thr Ile Ser Arg Glu Asp Ser Lys Asn Thr Leu Tyr Leu Gln Met Ser Ser Leu Lys Thr Glu Asp Leu Ala Val Tyr Tyr Cys Ala Arg (SEQ ID NO:94)
FR4: Trp Gly Gln Gly Thr Leu Val Thr Val Ser Ser (SEQ ID NO:95);

FR1: Glu Val Gln Leu Leu Glu Ser Gly Gly Gly Leu Val Gln Pro Gly Gly Ser Leu Arg Leu Ser Cys Ala Ala Ser Gly Phe Thr Phe Ser (SEQ ID NO:92)
FR2: Trp Val Arg Gln Ala Gln Gly Lys Gly Leu Glu Trp Val Gly (SEQ ID NO:96)
FR3: Arg Leu Thr Ile Ser Arg Glu Asp Ser Lys Asn Thr Leu Tyr Leu Gln Met Ser Ser Leu Lys Thr Glu Asp Leu Ala Val Tyr Tyr Cys Ala Arg (SEQ ID NO:94)
FR4: Trp Gly Gln Gly Thr Leu Val Thr Val Ser Ser (SEQ ID NO:95);

FR1: Glu Val Gln Leu Leu Glu Ser Gly Gly Gly Leu Val Gln Pro Gly Gly Ser Leu Arg Leu Ser Cys Ala Ala Ser Gly Phe Thr Phe Ser (SEQ ID NO:92)
FR2: Trp Val Arg Gln Ala Pro Gly Lys Gly Leu Glu Leu Val Gly (SEQ ID NO:97)
FR3: Arg Leu Thr Ile Ser Arg Glu Asp Ser Lys Asn Thr Leu Tyr Leu Gln Met Ser Ser Leu Lys Thr Glu Asp Leu Ala Val Tyr Tyr Cys Ala Arg (SEQ ID NO:94)
FR4: Trp Gly Gln Gly Thr Leu Val Thr Val Ser Ser (SEQ ID.NO:95);

FR1: Glu Val Gln Leu Leu Glu Ser Gly Gly Gly Leu Val Gln Pro Gly Gly Ser Leu Arg Leu Ser Cys Ala Ala Ser Gly Phe Thr Phe Ser (SEQ ID NO:92)
FR2: Trp Val Arg Gln Ala Pro Gly Lys Gly Leu Glu Trp Val Gly (SEQ ID NO:98)
FR3: Arg Leu Thr Ile Ser Arg Glu Asp Ser Lys Asn Thr Leu Tyr Leu Gln Met Ser Ser Leu Lys Thr Glu Asp Leu Ala Val Tyr Tyr Cys Ala Arg (SEQ ID NO:94)
FR4: Trp Gly Gln Gly Thr Leu Val Thr Val Ser Ser (SEQ ID NO:95);

FR1: Glu Val Gln Leu Leu Glu Ser Gly Gly Gly Leu Val Gln Pro Gly Gly Ser Leu Arg Leu Ser Cys Ala Ala Ser Gly Phe Thr Phe Ser (SEQ ID NO:92)
FR2: Trp Val Arg Gln Pro Pro Gly Lys Gly Leu Glu Trp Val Gly (SEQ ID NO:99)
FR3: Arg Leu Thr Ile Ser Arg Glu Asp Ser Lys Asn Thr Leu Tyr Leu Gln Met Ser Ser Leu Lys Thr Glu Asp Leu Ala Val Tyr Tyr Cys Ala Arg (SEQ ID NO:94)
FR4: Trp Gly Gln Gly Thr Leu Val Thr Val Ser Ser (SEQ ID NO:95);

FR1: Glu Val Gln Leu Leu Glu Ser Gly Gly Gly Leu Val Gln Pro Gly Gly Ser Leu Arg Leu Ser Cys Ala Ala Ser Gly Phe Thr Phe Ser (SEQ ID NO:92)
FR2: Trp Val Arg Gln Ala Pro Gly Lys Ala Leu Glu Trp Val Gly (SEQ ID NO:100)

FR3: Arg Leu Thr Ile Ser Arg Glu Asp Ser Lys Asn Thr Leu Tyr Leu Gln Met Ser Ser Leu Lys Thr Glu Asp Leu Ala Val Tyr Tyr Cys Ala Arg (SEQ ID NO:94)

FR4: Trp Gly Gln Gly Thr Leu Val Thr Val Ser Ser (SEQ ID NO:95);

FR1: Glu Val Gln Leu Leu Glu Ser Gly Gly Gly Leu Val Gln Pro Gly Gly Ser Leu Arg Leu Ser Cys Ala Ala Ser Gly Phe Thr Phe Ser (SEQ ID NO:92)

FR2: Trp Val Arg Gln Ala Pro Gly Lys Gly Leu Glu Trp Val Gly (SEQ ID NO:101)

FR3: Arg Phe Thr Ile Ser Arg Glu Asp Ser Lys Asn Thr Leu Tyr Leu Gln Met Ser Ser Leu Lys Thr Glu Asp Leu Ala Val Tyr Tyr Cys Ala Arg (SEQ ID NO:102)

FR4: Trp Gly Gln Gly Thr Leu Val Thr Val Ser Ser (SEQ ID NO:95); or,

FR1: Glu Val Gln Leu Leu Glu Ser Gly Gly Gly Leu Val Gln Pro Gly Gly Ser Leu Arg Leu Ser Cys Ala Ala Ser Gly Phe Thr Phe Ser (SEQ ID NO:92)

FR2: Trp Val Arg Gln Ala Gln Gly Lys Gly Leu Glu Trp Val Gly (SEQ ID NO:103)

FR3: Arg Phe Thr Ile Ser Arg Glu Asp Ser Lys Asn Thr Leu Tyr Leu Gln Met Ser Ser Leu Lys Thr Glu Asp Leu Ala Val Tyr Tyr Cys Ala Arg (SEQ ID NO:102)

FR4: Trp Gly Gln Gly Thr Leu Val Thr Val Ser Ser (SEQ ID NO:95)

In addition, the present invention also relates to DNA that codes for polypeptide that comprises the above-mentioned various antibodies, and their fragments. The present invention also relates to a vector that contains the above-mentioned DNA, an example of which is an expression vector. Moreover, the present invention provides a host that is transformed by the above-mentioned vector.

Moreover, the present invention also provides a process for producing chimeric antibody against human IL-8, and its fragments, as well as a process for producing reshaped human antibody against human IL-8, and its fragments.

BRIEF DESCRIPTION OF THE DRAWINGS

FIG. 3 is a diagram of the construction of DNA that codes for the amino acid sequences of each of the first version "a" (RVHa) of the H chain V region of reshaped human WS-4 antibody of the present invention (A), and the first version "a" (RVLa) of the L chain V region of reshaped human WS-4 antibody (B).

SPECIFIC MODE FOR CARRYING OUT THE INVENTION

Figure 1:
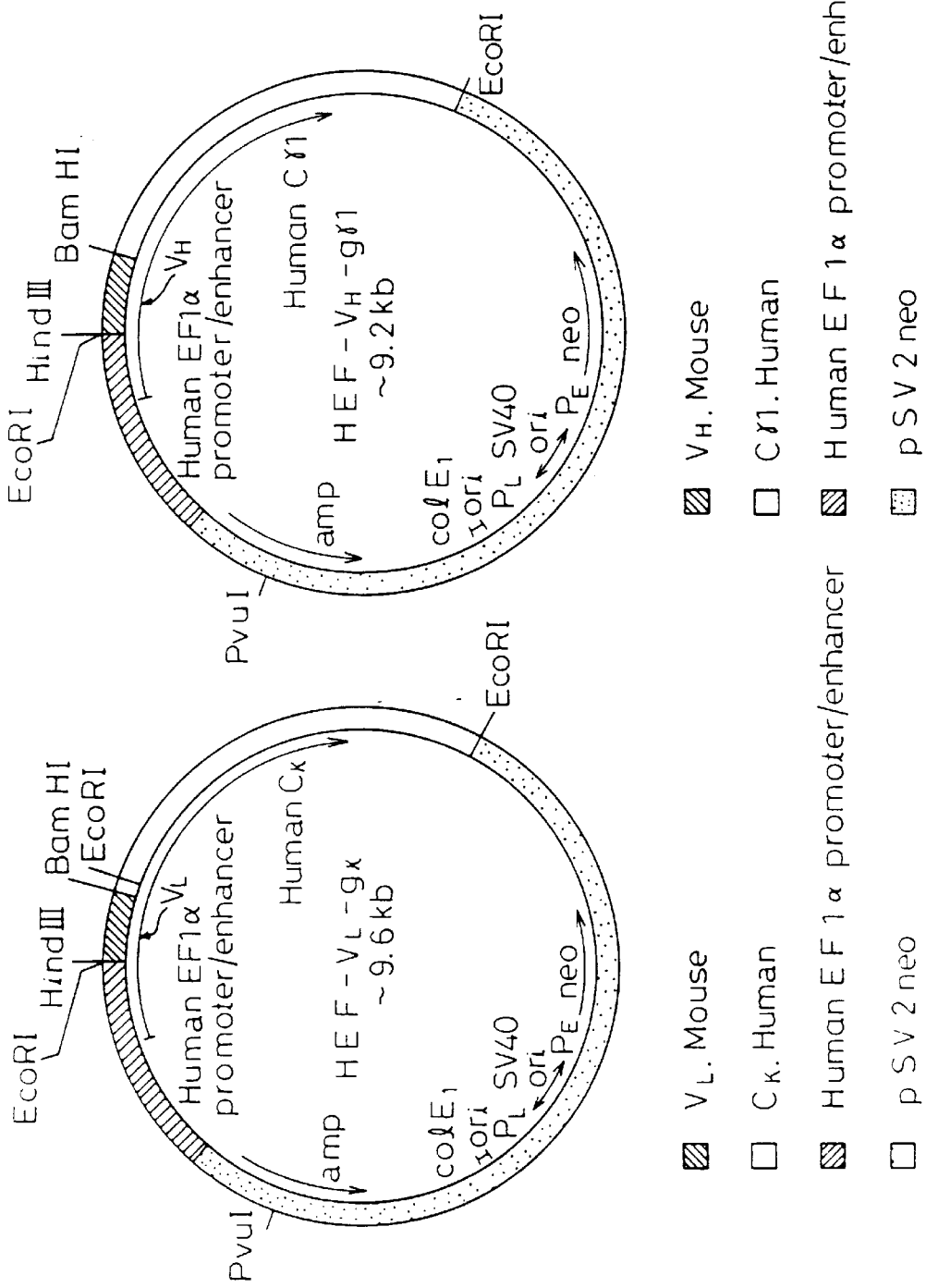
FIG. 1 indicates the expression vectors HEF-VL-gκ and HEF-VH-gγ1, containing the human elongation factor-1α (HEF-1α) promoter/enhancer, which are useful for expression of the L chain and H chain, respectively, of the antibody of the present invention.

Cloning of DNA Coding for Mouse V Region

In order to clone a gene that codes for the V region of mouse monoclonal antibody against human IL-8, it is necessary to prepare a hybridoma that produces mouse monoclonal antibody against human IL-8 for the acquisition of such a gene. After the extraction of mRNA from the hybridoma, the mRNA is converted into single-stranded cDNA according to known methods, followed by amplification of the target DNA using the polymerase chain reaction (PCR) to obtain the gene. An example of a source of this gene is the hybridoma WS-4, which produces mouse monoclonal antibody against human IL-8, produced by Ko, Y. C. et al. The process for preparing this hybridoma is described in J. Immunol. Methods, 149, 227–235, 1992, and is described later as Reference Example 1.

(1) Extraction of Total RNA

In order to clone the target DNA that codes for the V region of mouse monoclonal antibody against human IL-8, total RNA can be obtained by disrupting the hybridoma cells by guanidine thiocyanate treatment and performing cesium chloride density gradient centrifugation (Chirgwin, J. M. et al., Biochemistry, 18, 5294–5299, 1979). Furthermore, other methods that are used during the cloning of genes, such as that in which detergent treatment and phenol treatment are performed in the presence of a ribonuclease (RNase) inhibitor such as vanadium complex (Berger, S. L. et al., Biochemistry, 18, 5143–5149, 1979), can also be used.

(2) cDNA Synthesis

Next, single-stranded cDNA complementary to mRNA can be obtained by treating the total RNA with reverse transcriptase using oligo(dT), an oligonucleotide complementary to the poly (A) tail located at the 3' end of mRNA, as primer, and the mRNA contained in the total RNA obtained in the above manner as template (Larrick, J. W. et al., Bio/Technology, 7, 934–938, 1989). In addition, a random primer may also be used at the same time. Furthermore, in the case that it is desired first to isolate mRNA, this may be done by applying the total RNA to a column of oligo (dT)-cellulose, to which the poly(A) tail of mRNA binds.

(3) Amplification of DNA Coding for V Region by Polymerase Chain Reaction

Next, cDNA that codes for the above-mentioned V region is specifically amplified using the polymerase chain reaction (PCR). In order to amplify the kappa (κ) type L chain V region of mouse monoclonal antibody, the 11 types of oligonucleotide primers shown in SEQ ID NOs:1 to 11 (Mouse Kappa Variable; MKV) and the oligonucleotide primer shown in SEQ ID No:12 (Mouse Kappa Constant; MKC) are used as the 5' terminal primer and the 3' terminal primer, respectively. The above-mentioned MKV primers hybridize to the DNA sequence that codes for the mouse kappa-type L chain leader sequence, while the above-mentioned MKC primer hybridizes to the DNA sequence that codes for the mouse kappa-type L chain C region.

In order to amplify the H chain V region of mouse monoclonal antibody, the 12 types of oligonucleotide primers shown in SEQ ID NOs:13 to 24 (Mouse Heavy Variable; MHV) and the oligonucleotide primer shown in SEQ ID No:25 (Mouse Heavy Constant; MHC) are used as the 5' terminal primer and the 3' terminal primer, respectively. The above-mentioned MHV primers hybridize to the DNA sequence that codes for the mouse H chain leader sequence, while the above-mentioned MHC primer hybridizes to the DNA sequence that codes for the mouse H chain C region.

Furthermore, all 5' terminal primers (MKV and MHV) contain the sequence GTCGAC that provides a SalI restriction enzyme cleavage site near the 3' terminus, while both 3'-terminal primers (MKC and MHC) contain the nucleotide sequence CCCGGG that provides an XmaI restriction enzyme cleavage site near the 5' terminus. These restriction enzyme cleavage sites are used for the subcloning of target DNA fragments that code for both V regions into the respective cloning vectors. In the case that these restriction enzyme cleavage sites are also present in the target DNA sequence that codes for both V regions, other restriction enzyme cleavage sites should be used for subcloning into the respective cloning vectors.

(4) Isolation of DNA Coding for V Region

Next, in order to obtain the DNA fragment that codes for the target V region of mouse monoclonal antibody, the PCR amplification products are separated and purified on a low melting-point agarose gel or by a column [PCR Product Purification kit (QIAGEN PCR Purification Spin Kit: QIAGEN); DNA purification kit (GENECLEAN II, BIO101). A DNA fragment is obtained that codes for the target V region of mouse monoclonal antibody by enzyme treatment of the purified. amplification product with the restriction enzymes SalI and XmaI.

Further, by cleaving a suitable cloning vector, like plasmid pUC19, with the same restriction enzymes, SalI and XmaI, and enzymatically linking the above-mentioned DNA fragment to this pUC19, a plasmid is obtained which contains a DNA fragment that codes for the target V region of mouse monoclonal antibody. Determination of the sequence of the cloned DNA can be performed in accordance with any routine method, an example of which is the use of an automated DNA sequencer (Applied Biosystems). Cloning and sequence determination of the target DNA are described in detail in Examples 1 and 2.

Complementarity Determining Regions (CDRs)

The present invention also provides hyper-V region or complementarity determining region (CDR) of the V region of mouse monoclonal antibody against human IL-8. V regions of both the L chain and H chain of the antibody form an antigen binding site. These regions on the L chain and the H chain have a similar basic structure. The V regions of both chains contain four framework regions for which the sequence is relatively conserved, and these four framework regions are linked by three hyper-V regions or CDR (Kabat, E. A. et al, "Sequences of Proteins of Immunological Interest", U.S. Dept. Health and Human Services, 1991).

The majority of the portions of the above-mentioned four framework regions (FR) have a β-sheet structure, and the three CDRs form loops. The CDRs may form a portion of the β sheet structure in some cases. The three CDRs are maintained at extremely close positions three-dimensionally by the FRs, and contribute to formation of the antigen binding site together with three paired CDRs. The present invention provides CDRs that are useful as components of humanized antibody, as well as the DNA that codes for them. These CDRs can be determined from the experimental rules of Kabat, E. A. et al. "Sequences of Proteins of Immunological Interest", by comparing V region sequences with known amino acid sequences of the V region, a detailed explanation of which is provided in Embodiment 3.

Preparation of Chimeric Antibody

Prior to designing a reshaped human V region of antibody against human IL-8, it is necessary to confirm whether the CDRs used actually form an antigen-binding region. Chimeric antibody was prepared for this purpose. In order to prepare chimeric antibody, it is necessary to construct DNA that codes for the L chain and the H chain of chimeric antibody. The basic method for constructing both DNA involves linking the respective DNA sequences of the mouse leader sequence observed in PCR-cloned DNA and the mouse V region sequence to a DNA sequence that codes for human C region already present in a mammalian cell expression vector.

The above-mentioned human antibody C regions can be any human L chain C region and any human H chain C region, and with respect to the L chain, examples include human L chain Cκ or Cλ, while with respect to the H chain if IgG, examples include Cγ1, Cγ2, Cγ3 or Cγ4 (Ellison, J. et al., DNA, 1, 11-18 (1981), Takahashi, N. et al., Cell, 29, 671–679 (1982), Krawinkel, U. et al., EMBO J., 1, 403–407 (1982)), or other isotypes.

Two types of expression vectors are prepared for production of chimeric antibody, namely, an expression vector that contains DNA that codes for mouse L chain V region and human L chain C region under the control of an enhancer/promoter expression control region, and an expression vector that contains DNA that codes for mouse H chain V region and human H chain C region under the control of an enhancer/promoter type of expression control region. Next, host cells such as mammalian cells are simultaneously transformed by both of these expression vectors, and the transformed cells are cultured either in vitro or in vivo to produce chimeric antigen (e.g. WO91–16928).

Alternatively, DNA that codes for mouse L chain V region and human L chain C region and DNA that codes for mouse H chain V region and human H chain C region can be introduced into a single expression vector, host cells are transformed using said vector, and are then cultured either in vitro or in vivo to produce chimeric antibody.

The production of chimeric antibody from monoclonal antibody WS-4 is described in Embodiment 4.

cDNA that codes for mouse WS-4 κ-type L chain leader sequence and the V region is cloned using PCR, and linked to an expression vector that contains human genome DNA that codes for the human L chain Cκ region. Similarly, cDNA that codes for the H chain leader sequence and V region of mouse WS-4 antibody is cloned using PCR and linked to an expression vector that contains human genome DNA that codes for human Cγ1 region.

More specifically, suitable nucleotide sequences are introduced at the 5' and 3' termini of cDNAs that code for the V regions of mouse WS-4 antibody using specially designed PCR primers so that (1) they can be easily inserted into the expression vector, and (2) they function suitably in said expression vector (for example, transcription efficiency is improved by introducing a Kozak sequence in the present invention).

Next, DNA that codes for the V region of mouse WS-4 antibody obtained by amplification by PCR using these primers is introduced into HEF expression vector (see FIG. 1) that already contains the desired human C region. These vectors are suitable for transient or stable expression of antibody genetically engineered in various mammalian cell systems.

Figure 2:
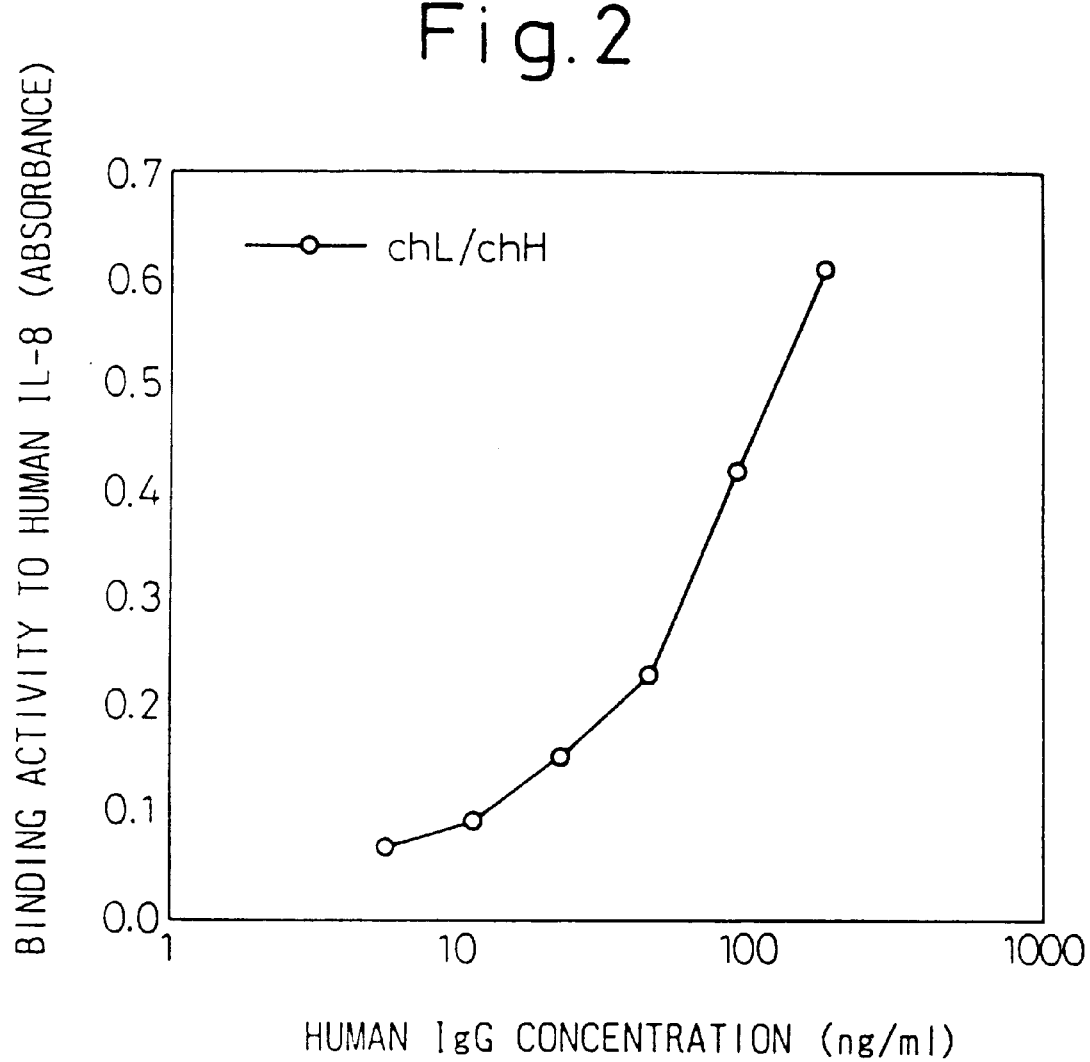
FIG. 2 is a graph indicating the results of ELISA for confirmation of the binding ability to human IL-8 of the chimeric WS-4 antibody (chL/chH) of the present invention secreted into the culture medium of COS cells.

When the antigen-binding activity of the chimeric WS-4 antibody prepared in this manner was tested, the chimeric WS-4 antibody demonstrated binding activity to human IL-8 (see FIG. 2). Thus, it was concluded that the correct mouse V region had been cloned, and the correct sequence had been determined.

Design of Reshaped Human WS-4 Antibody

In order to prepare a reshaped human antibody in which the CDRs of mouse monoclonal antibody are grafted onto human antibody, it is desirable that there be a high degree of homology between the amino acid sequences of the FRs of the mouse monoclonal antibody having the CDRs to be grafted, and the amino acid sequences of the FRs of the human monoclonal antibody into which the CDRs are to be grafted.

For this purpose, the human V regions to serve as the basis for designing the V regions of the reshaped human WS-4 antibody can be selected by comparing the amino acid sequences of the FRs of the mouse monoclonal antibody with the amino acid sequence of the FR of the human antibodies. More specifically, the V regions of the L and H chains of mouse WS-4 antibody were compared with all known human V regions found in the database of the National Biomedical Research Foundation (NBRF) using the genetic analytical software, GENETEX (Software Development Co., Ltd.).

In a comparison with known human L chain V regions, the L chain V region of mouse WS-4 antibody was found to resemble most closely that of human antibody HAU (Watanabe, S. et al., Hoppe-Seyler's Z. Physiol. Chem., 351, 1291–1295, 1970), having homology of 69.2%. On the other hand, in a comparison with known human antibody H chain V regions, the H chain V region of WS-4 antibody was found to resemble most closely that of human antibody VDH26 (Buluwela, L. et al., EMBO J., 7, 2003–2010, 1988), having homology of 71.4%.

In general, homology of the amino acid sequences of mouse V regions to the amino acid sequences of human V regions is less than the homology to amino acid sequences of mouse V regions. This indicates that the V region of mouse WS-4 antibody does not completely resemble the human V region, and at the same time, indicates that humanization of mouse WS-4 V region is the best way to solve the problem of immunogenicity in human patients.

The V region of mouse WS-4 antibody was further compared with the consensus sequence of human V region subgroup defined by Kabat, E. A. et al., (1991), Sequences of Proteins of Immunological Interest, Fifth Edition, U.S. Department of Health and Human Services, U.S. Government Printing Office, to compare between V region FR. Those results are shown in Table 1.

TABLE 1

Homology (%) Between FR of Mouse WS-4 V Region and FR of the Consensus Sequence of the Human V Regions of Various Subgroups

| HSGI | HSGII | HSGIII | HSGIV |
|---|---|---|---|
| A. FR in L Chain V Region | | | |
| 64.4 | 51.3 | 57.3 | 57.5 |
| B. FR in H Chain V Region | | | |
| 46.9 | 40.9 | 62.3 | |

The FRs of the L chain V region of mouse WS-4 antibody most closely resembled the consensus sequence of FR of the human L chain V region subgroup I (HSGI), having homology of 64.4%. On the other hand, the FRs of the H chain V region of mouse WS-4 antibody most closely resembled the consensus sequence of human H chain V region subgroup III (HSGIII), having homology of 62.3%.

These results support the results obtained from the comparison with known human antibodies, the L chain V region of human antibody HAU belonging to human L chain V region subgroup I, and the H chain V region of human antibody VDH26 belonging to human H chain V region subgroup III. In order to design the L chain V region of reshaped human WS-4 antibody, it is probably best to use a human L chain V region belonging to subgroup I (HSGI), while in order to design the H chain V region of reshaped human WS-4 antibody, it is probably best to use the H chain V region of a human antibody belonging to subgroup III (HSGIII).

In a comparison with the L chain V region of known human antibodies, the L chain V region of mouse antibody WS-4 most closely resembled the L chain V region of human antibody REI, a member of subgroup I of human L chain V region. Thus, the FR of REI were used in designing the L chain V region of reshaped human WS-4 antibody. Within these human FR based on REI, there are differences in five amino acids (at positions 39, 71, 104, 105 and 107; see Table 2) in comparison with the human REI documented in the original literature (Palm, W. et al., Hoppe-Seyler's Z. Physiol. Chem., 356, 167–191, 1975; and, Epp, O. et al., Biochemistry, 14, 4943–4952, 1975).

The amino acid numbers shown in the table are based on the experience of Kabat, E. A. et al. (1991). The changes in the two amino acids at positions 39 and 71 were same changes caused by the amino acids present in the FR of the L chain V region of rat CAMPATH-1H antibody (Riechmann, et al., 1988). According to Kabat, et al. (1991), the changes in the other three amino acids in FR4 (positions 104, 105 and 107) are based on the J region from other human κL chains, and do not deviate from humans.

Two versions of the L chain V region of reshaped human WS-4 antibody were designed. In the first version RVLa, FR was identical to the FR based on REI present in reshaped human CAMPATH-1H antibody (Riechmann, et al., 1988), while the CDR was identical to the CDR in the L chain V region of mouse WS-4 antibody. The second version, RVLb, was based on RVLa, and differed only by one amino acid at position 71 in human FR3. As defined by Chothia, C. et al., J. Mol. Biol., 196, 901–917, 1987, residue 71 is a portion of the canonical structure of the CDR1 of the L chain V region.

Amino acid at this position is predicted to directly affect the structure of the CDR1 loop of the L chain V region, and for this reason, it considered to have a significant effect on antigen binding. In RVLb of the L chain V region of reshaped human WS-4 antibody, the phenylalanine at position 71 is changed to tyrosine. Table 2 shows the respective amino acid sequences of the L chain V region of mouse WS-4 antibody, the FR of the modified REI for use in reshaped human CAMPATH-IH antibody (Riechmann, et al., 1988) and the two versions of the L chain V region of reshaped human WS-4 antibody.

The FR in the H chain V region of mouse WS-4 antibody most closely resemble the human H chain V region belonging to subgroup III (Table 1).

In a comparison with known human H chain V regions, the H chain V region of mouse WS-4 antibody most closely resembled the H chain V region of human antibody VDH26, a member of subgroup III of the human H chain V region, from FRI to FR3 (Buluwela, L. et al., EMBO J., 7, 2003–2010, 1988). With respect to FR4, since the FR4 sequence of VDH26 was not reported, it was decided to use the amino acid sequence of FR4 of human antibody 4B4 belonging to subgroup III (Sanz, I. et al., J. Immunol., 142, 883–887, 1989). These human H chain V regions were used as the basis for designing the H chain V region of reshaped human WS-4 antibody.

Eight versions of the H chain V region of reshaped human WS-4 antibody were designed. In all eight versions, human FR1, FR2 and FR3 were based on FR1, FR2 and FR3 of human antibody VDH26, while FR4 was based on FR4 of human antibody 4B4. Mouse CDR was identical to the CDR of the H chain V region of mouse WS-4 antibody.

TABLE 2

Design of L Chain V Region of Reshaped Human WS-4

```
              1               2           3              4
       12345678901234567890123   45678901234  567890123456789

WS-4L  DIQMTQSPASLSASVGETVTITC   RASEIIYSYLA  WYQQKQGKSPQLLVY

REI    DIQMTQSPSSLSASVGDRVTITC                WYQQKPGKAPKLLIY

RVLa   DIQMTQSPSSLSASVGDRVTITC   RASEIIYSYLA  WYQQKPGKAPKLLIY

RVLb   -----------------------   -----------  ---------------
                FR1                 CDR1           FR2

5         6         7           8                9

0123456    789012345678901234567890123456789   901234567

WS-4l  NAKTLAD    GVSSRFSGSGSGTQFSLRISSLQPEDFGSYYC    QHHFGFPRT

REI               GVPSRFSGSGSGTDFTFTISSLQPEDIATYYC

RVLa   NAKTLAD    GVPSRFSGSGSGTDFTFTISSLQPEDIATYYC    QHHFGFPRT

RVLb   -------    ---------------y----------------    ---------
           CDR2              FR3                        CDR3

10

8901234567

WS-4L   FGGGTKLELK    (Residues 1-107 of SEQ ID NO:26)

REI     FGQGTKVEIK    (SEQ ID NO:104)

RVLa    RGQGTKVEIK    (Residues 1-107 of SEQ ID NO:73)

RVLb    ----------    (Residues 1-107 of SEQ ID NO:77)
```

Note: FR of REI is found in reshaped human CAMPATH-1H antibody (Riechmann, et al., 1988). The five underlined amino acids in the FR of REI are amino acids that differ from the amino acid sequence of human REI. Amino acids are designated using the single letter code. Amino acid numbers are in accordance with the definition of Kabat et al.

Tables 3 and 4 show the respective amino acid sequences of the H chain V region of mouse WS-4 antibody, the template FR1 through FR3 of human antibody VDH26, FR4 of human antibody 4B4, and the 8 versions of the H chain V region of reshaped human WS-4 antibody.

TABLE 3

Design of H Chain V Region of Reshaped Human WS-4 Antibody

```
                          1         2         3
             12345678901234567890123456789 0    12345

WS-4H     EVKLVESGGGLIQPGDSLRLSCVTSGFTFS       DYYLS  (Residues 1-30 of
                                                      SEQ ID NO:29)

VDH26     EVQLLESGGGLVQPGGSLRLSCAASGFTFS

RVha~h    EVQLLESGGGLVQPGGSLRLSCAASGFTFS       DYYLS

FR1                  CDR1

4              5         6
             67890123456789    012ABC3456789012345

WS-4H     WVRQPPGKALEWVG     LIRNKANGYTREYSASVKG   (Residues 36-68 of
                                                   SEQ ID NO:29)

VDH26     WVRQAQGKGLELVG

RVHa      WVRQAQGKGLELVG     LIRNKANGYTREYSASVKG

RVHb      -----------W--     -------------------

RVHc      -----P--------     -------------------

RVHd      -----P-----W--     -------------------

RVHe      ----PP-----W--     -------------------

RVHf      -----P--A--W--     -------------------

RVHg      -----P-----W--     -------------------

RVHh      -----------W--     -------------------

FR2                CDR2
```

TABLE 4

Design of H Chain V Region of Reshaped Human WS-4

```
               7         8         9        10
          67890123456789012ABC345678901234  567890ABC12

WS-4H   RFTISRDDSQSILYLQMNTLRGEDSATYYCAR    ENYRYDVELAY  (Residues 69-111
                                                         of SEQ ID NO:29)

VDH26   RLTISREDSKNTLYLQMSSLKTEDLAVYYCAR

RVHa    RLTISREDSKNTLYLQMSSLKTEDLAVYYCAR    ENYRYDVELAY

RVHb    -------------------------------    -----------  (Residues 1-122
                                                         of SEQ ID NO:45)

RVHc    -------------------------------    -----------  (Residues 1-122
                                                         of SEQ ID NO:49)

RVHd    -------------------------------    -----------  (Residues 1-122
                                                         of SEQ ID NO:51)

RVHe    -------------------------------    -----------  (Residues 1-122
                                                         of SEQ ID NO:55)
```

TABLE 4-continued

Design of H Chain V Region of Reshaped Human WS-4

```
RVHf    --------------------------------  -----------  (Residues 1-122
                                                        of SEQ ID NO:59)
RVHg    -F-------------------------------  -----------  (Residues 1-122
                                                        of SEQ ID NO:63)
RVHh    -F-------------------------------  -----------  (Residues 1-122
                                                        of SEQ ID NO:65)

FR3                    CDR3

11
          34567890123

WS-4H   WGQGTLVTVSA (Residues 112-122 of SEQ ID NO:29)

4B4     WGQGTLVTVSS (SEQ ID NO:105)

RVHa    WGQGTLVTVSS (Residues 1-106 of SEQ ID NO:41)
```

Note: RVHa-h indicates RVHa, RVHb, RVHc, RVHd, RVHe, RVHf, RVHg and RVHh.

Amino acids are designated using the single letter code. Amino acid numbers are in accordance with the definition of Kabat et al.

Preparation of DNA Coding for V Region of Reshaped Human WS-4 Antibody

Preparation of the V region of reshaped human WS-4 antibody is described in detail in Example 5.

DNAs that code for the respective first versions of the L chain and H chain V regions of reshaped human WS-4 antibody were synthesized. It was then confirmed that the entire DNA sequence of version "a" of the L chain and H chain V regions of reshaped human WS-4 antibody codes for the correct amino acid sequence by sequence determination. The sequence of version "a" of the L chain v region of reshaped human WS-4 antibody is shown in SEQ ID NO:73, while the sequence of version "a" of the H chain V region of reshaped human WS-4 antibody is shown in SEQ ID NO:41.

DNAs that code for other versions of V region of reshaped human WS-4 antibody were prepared using a slight variation of the publicly disclosed PCR-mutation induction method (Kammann, M. et al., Nucleic Acids Res., 17, 5404, 1989) with the first version "a" as the template. As previously described in relation to the design of the V region of the reshaped human WS-4 antibody, DNA that codes for one additional version of the L chain V region of reshaped human WS-4 antibody (version "b"), as well as DNA that code for seven additional versions of the H chain V region of reshaped human WS-4 antibody (versions "b", "c", "d", "e", "f", "g" and "h") were prepared.

These additional versions contained slight changes in a series of amino acid sequences from the first version, and these changes in the amino acid sequences were achieved by making slight changes in the DNA sequence using PCR mutation induction. A PCR primer was designed that introduces the required change in the DNA sequence. After a series of PCR reactions, the PCR product was cloned followed by sequence determination to confirm that the changes in the DNA sequence had occurred as designed. The sequence of version "b" of the L chain V region of reshaped human WS-4 antibody is shown in SEQ ID NO:77, while the sequences of versions "b", "c", "d", "e", "f", "g" and "h" of the H chain V region of reshaped human WS-4 antibody are shown in SEQ ID NOs:45, 49, 51, 55, 59, 63 and 65, respectively.

After confirming the DNA sequences of various versions of the V region of reshaped human WS-4 antibody by sequence determination, the DNAs that code for the V region of reshaped human WS-4 antibody were subcloned to mammalian cell expression vectors that already contain DNA that codes for the human C region. Namely, DNA that codes for the V chain L region of reshaped human WS-4 antibody was linked to a DNA sequence that codes for human L chain C region, while DNA that codes for the H chain V region of reshaped human WS-4 antibody was linked to a DNA sequence that codes for the human Cγ1 region.

Figure 7:
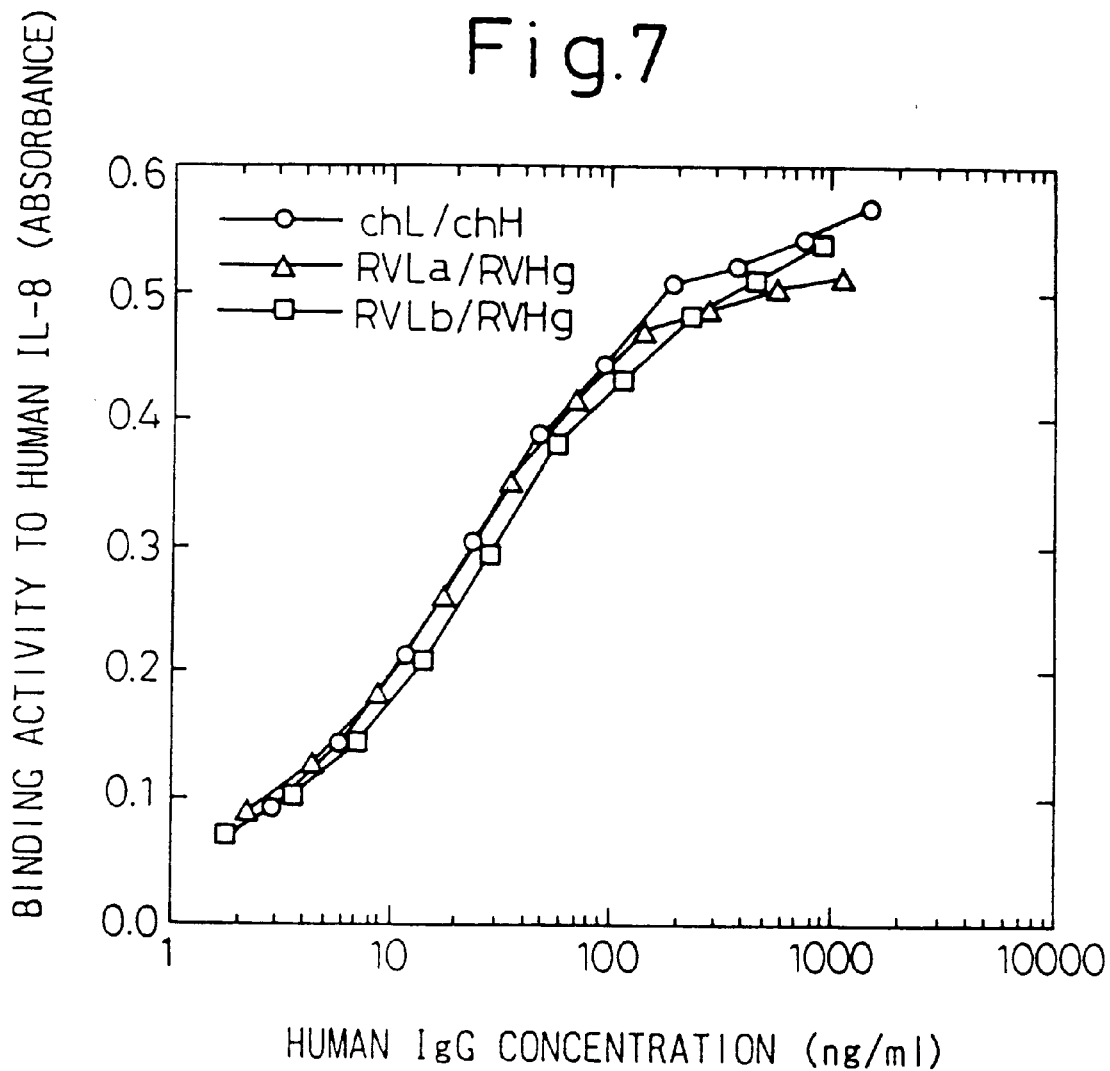
FIG. 7 is a graph indicating the results of ELISA for comparing the binding abilities to human IL-8 of the purified reshaped human WS-4 antibodies RVLa/RVHg and RVLb/ RVHg of the present invention and the purified chimeric WS-4 antibody (chL/chH) of the present invention.

Next, all combinations of version "a" or "b" of the reshaped human L chain V region, and versions "a" through "h" of the H chain V region were tested for binding to human IL-8. As a result, as is shown in FIG. 7, both reshaped human antibodies containing L chain version "a" or "b" and H chain version "g" (RVLa/RVHg and RVLb/RVHg) demonstrated the ability to bind to human IL-8 to the same extent as chimeric WS-4 antibody.

Any expression system, including eukaryotic cells such as animal cells or established mammalian cells, fugus cells, yeast cells and procaryotic cells such as bacterial cells (e.g. Escherichia coli) can be used for producing the chimeric antibody or reshaped human antibody against human IL-8 of the present invention. Preferably, however, the chimeric antibody or reshaped antibody of the present invention is expressed in mammalian cells, such as COS cells or CHO cells. In these cases, a useful, commonly used promoter can be used to express in mammalian cells. For example, it is preferable to use the human cytomegalovirus immediate early (HCMV) promoter. Examples of expression vectors that contain HCMV promoter include HCMV-VH-HCγ1 and HCMV-VL-HCκ, as well as those derived from pSV2neo (International Patent Application Publication No. WO92-19759) are also included.

In addition, examples of other promoters of genetic expression in mammalian cells that can be used in the present invention that should be used include virus promoters such as retrovirus, polioma virus, adenovirus and simian virus 40 (SV40), as well as promoters originating in mammalian cells such as human polypeptide chain elongation factor-1α (HEF-1α). For example, in the case of using SV40 promoter, expression can be performed by following the method of Mulligan, R. C. et al. (Nature, 277, 108–114, 1979) or in the case of using HEF-1α promoter, expression can be performed by following the method of Mizushima, S. et al. (Nucleic Acids Res., 18, 5322, 1990).

Another specific example of a useful promoter for the present invention is HEF-1α promoter. HEF-VH-gγ1 and HEF-VL-gκ (FIG. 1) are contained in an expression vector containing this promoter. DNA sequences originating in polyoma virus, adenovirus, SV40 or bovine papilloma virus (BPV) and so forth can be used as repricator points. Moreover, in order to amplify the number of genetic copies in the host cells, aminoglucoside-3'-phosphotransferase, neo-resistant gene, thymidine kinase (TK) gene, *E. coli* xanthin-guanine phosphoribosyl-transferase (XGPRT) gene or dihydrofolate reductase (dhfr) can be used as selection markers.

In summary, the present invention first provides an L chain V region and H chain V region of mouse monoclonal antibody against human IL-8, as well as DNA that codes for said L chain V region and DNA that codes for said H chain V region. These are useful in the preparation of human/mouse chimeric antibody and reshaped human antibody to human IL-8. An example of monoclonal antibody is WS-4. The L chain V region has the amino acid sequence shown in, for example, SEQ ID NO:26, while the H chain V region has the amino acid sequence shown, for example, in SEQ ID NO:29. These amino acid sequences are coded for by nucleotide sequences shown, for example, in SEQ ID NOs:26 and 29, respectively.

The chimeric antibody against human IL-8 of the present invention comprises:

(1) a human L chain C region and mouse L chain V region; and, (2) a human H chain C region and mouse H chain V region.

The mouse L chain V region, mouse H chain V region and DNAs that code for these are as previously described. The above-mentioned human L chain C region can be any human L chain C region, examples of which include the human Cκ and Cλ regions. The above-mentioned human H chain C region can be any human H chain C region, examples of which include the human Cγ1, Cγ2, Cγ3 or Cγ4 region (Ellison, J. et al., DNA, 1, 11–18 (1981), Takahashi, N. et al., Cell, 29, 671–679 (1982), and Krawinkel, U. et al., EMBO J., 1, 403–407 (1982)).

Two types of expression vectors are prepared for producing chimeric antibody. Namely, an expression vector that contains DNA that codes for the mouse L chain V region and human L chain C region under the control of an enhancer/promoter type of expression control region, and an expression vector that contains DNA that codes for the mouse H chain V region and human H chain C region under the control of an enhancer/promoter type of expression control region. Next, host cells in the manner of mammalian cells are simultaneously transformed with these expression vectors, and the transformed cells are cultured either in vitro or in vivo to produce chimeric antibody.

Alternatively, DNA that codes for mouse L chain V region and human L chain C region and DNA that codes for mouse H chain V region and human H chain C region can be introduced into a single expression vector, host cells are transformed using said vector, and those transformed cells are then cultured either in vitro or in vivo to produce chimeric antibody.

The reshaped human WS-4 antibody of the present invention comprises:

(A) L chains each comprising:
(1) a human L chain C region; and,
(2) an L chain V region comprising a human L chain FRs, and an L chain CDRs of mouse monoclonal antibody WS-4 against human IL-8, as well as (B) H chains each comprising:
(1) a human H chain C region; and,
(2) an H chain V region comprising a human H chain FRs, and H chain CDRs of mouse monoclonal antibody WS-4 against human IL-8.

In a preferable mode of the present invention, the above-mentioned L chain CDR is within the amino acid sequence shown in SEQ ID NO:26, with the extents of said amino acid sequence being defined in Table 5; the above-mentioned H chain CDR is within the amino acid sequence shown in SEQ ID NO:29, with the extents of said amino acid sequence being defined in Table 5; the above-mentioned human L chain FR is derived from REI; the above-mentioned human H chain FR1, FR2 and FR3 are derived from VDH26, and FR4 is derived from 4B4; the above-mentioned human L chain C region is the human Cκ region; and, the above-mentioned human H chain C region is the human Cγ1 region. In addition, the above-mentioned human H chain C region may be the human Cγ4 region, or a radioisotope may be bound instead of the above-mentioned human L chain C region and/or human H chain C region.

It is preferable to substitute a portion of the amino acid sequence of the above-mentioned human FR to prepare reshaped human antibody that has sufficient activity with respect to a specific antigen.

In a preferable mode of the present invention, the L chain V region has the amino acid sequence shown as RVLa or RVLb in Table 2, while the H chain V region has the amino acid sequence shown as RVHa, RVHb, RVHc, RVHd, RVHe, RVHf, RVHg or RVHh in Tables 3 and 4. Moreover, the amino acid at position 41 in the H chain V region FR2 should be proline, the amino acid at said position 47 should be tryptophan, and/or the amino acid at position 67 of said FR3 should be phenylalanine, and those having the amino acid sequences shown as RVHb, RVHd, RVHe, RVHf, RVHg or RVHh are more preferable. That in which RVHg is present as the H chain V region is the most preferable.

Two types of expression vectors are prepared for production of reshaped antibody. Namely, an expression vector that contains DNA that codes for the previously defined reshaped human L chain under control by an enhancer/promoter type of expression control region, as well as another expression vector that contains DNA that codes for the previously defined reshaped human H chain under control by an enhancer/promoter type of expression control region, are prepared. Next, host cells such as mammalian cells are simultaneously transformed by these expression vectors, and the transformed cells are cultured either in vitro or in vivo to produce reshaped human antibody.

Alternatively, DNA that codes for reshaped human L chain and DNA that codes for reshaped human H chain are introduced into a single expression vector, host cells are transformed using said vector, and those transformed cells are then cultured either in vitro or in vivo to produce the target reshaped human antibody.

The chimeric antibody or reshaped human antibody produced in this manner can be isolated and purified in accordance with routine methods such as protein A affinity chromatography, ion exchange chromatography or gel filtration.

The chimeric L chain or reshaped human L chain of the present invention can be used to prepare complete antibody by combining with an H chain. Similarly, the chimeric H chain or reshaped human H chain of the present invention can be used to prepare complete antibody by combining with an L chain.

The mouse L chain V region, reshaped human L chain V region, mouse H chain V region and reshaped human H chain V region are inherently regions that bind to antigen in the form of human IL-8. They are considered to be useful as pharmaceuticals, diagnostic drugs and so forth either alone or in the form of fused protein with other proteins.

In addition, the L chain V region CDR and H chain V region CDR of the present invention are also inherently portions that bind to antigen in the form of human IL-8. These are considered to be useful as pharmaceuticals, diagnostic drugs and so forth either alone or in the form of fused protein with other proteins.

The DNA that codes for mouse L chain V region of the present invention is useful for preparing DNA that codes for chimeric L chain, or DNA that codes for reshaped human L chain. Similarly, the DNA that codes for mouse H chain V region is useful for preparing DNA that codes for chimeric H chain or DNA that codes for reshaped human H chain. In addition, the DNA that codes for the L chain V region CDR of the present invention is useful for preparing DNA that codes for reshaped human L chain V region, or DNA that codes for reshaped human L chain.

Similarly, the DNA that codes for the H chain V region CDR of the present invention is useful for preparing DNA that codes for reshaped human H chain V region, and DNA that codes for reshaped human H chain. Moreover, reshaped human antibody F(ab')$_2$, Fab or Fv, or single chain Fv that couples both Fv of the H chain and L chain, can be produced in a suitable host and used for the purposes described above (see, for example, Bird, R. E. et al., TIBTECH, 9, 132–137, 1991).

Single chain Fv is composed by linking the H chain V region and L chain V region of reshaped human antibody to human IL-8. In this single chain Fv, the H chain V region and L chain V region are linked by a linker, and preferably a peptide linker (Huston, J. S. et al., Proc. Natl. Acad. Sci. USA, 85, 5879–5883, 1988).

The H chain V region and L chain V region of this single chain Fv may be either of the above-mentioned H chain and L chain V regions of reshaped human antibody. Specific examples of these include the H chain V regions composed of the amino acid sequences described in SEQ ID NOs:41, 45, 49, 51, 55, 59 and 63, and single chain Fv containing an L chain V region composed of the amino acid sequences described in SEQ ID NO:73 or 77 (see WO88-01649).

These V regions are preferably linked by a peptide linker. Examples of peptide linkers that are used include any arbitrary single chain peptide composed of, for example 12–19 residues (see WO88–09344).

DNA that codes for single chain Fv is obtained by using DNA that codes for the H chain or H chain V region and DNA that codes for the L chain or L chain V region of the above-mentioned reshaped human antibody as template, amplifying the portion of DNA that codes for those amino acid sequences that are desired using a primer pair that defines both ends by PCR, and amplifying by combining a primer pair that defines DNA that codes for a polypeptide linker along with both its ends so as to respectively link the H and L chains.

In addition, once the DNA that code for single chain Fv are prepared, an expression vector that contains them along with a host that is transformed by said expression vector can be obtained in accordance with routine methods. In addition, single chain Fv can be obtained in accordance with routine methods by using that host.

In comparison with antibody molecules, single chain Fv exhibit better permeability into tissue, and are expected to be used in imaging by labelling with a radioisotope, and as a therapeutic agent having similar functions to reshaped human antibody.

ELISA (Enzyme-linked immunosorbent assay), EIA (Enzyme immunoassay), RIA (radioimmunoassay) or fluorescent antibody techniques can be used to confirm the binding activity of the chimeric antibody, reshaped human antibody and its F(ab')$_2$, Fab, Fv or single chain Fv against IL-8 of the present invention. For example, in the case of using enzyme immunoassay with chimeric antibody and reshaped human antibody, human IL-8 is added to a plate coated with anti-human IL-8 polyclonal antibody, a culture supernatant or purified sample of cells that produce chimeric antibody or reshaped human antibody against human IL-8 is added, and a suitable secondary antibody is added that is labeled with an enzyme such as alkaline phosphatase. After incubating and washing the plate, an enzyme substrate such as p-nitrophenylphosphate is added followed by measurement of absorbance to evaluate the antigen binding activity.

The IL-8 binding inhibitory activity to IL-8 receptors of the chimeric antibody, reshaped human antibody, and its F(ab')$_2$, Fab, Fv or single chain Fv against human IL-8 is evaluated by an ordinary ligand receptor binding inhibition assay. For example, in order to assay the inhibition of binding of IL-8 to IL-8 receptors on neutrophils, after separating neutrophils obtained from heparinized blood by centrifugation or other means, a cell suspension is prepared having a suitable number of cells that can be used in the above-mentioned assay.

A solution containing IL-8 suitably labeled with $^{125}$I and so forth and non-labeled IL-8 is mixed with a solution containing the antibody of the present invention or its fragments prepared at a suitable concentration, followed by the addition of this mixture to the above- mentioned neutrophil suspension. After a certain period of time, the neutrophils are separated, and the labeled activity on the neutrophils is assayed.

Routine known methods, such as the method described in Grob, P. M. et al., J. Biol. Chem., 265, 8311–8316, 1990, can be used for evaluation of the inhibition of neutrophil chemotaxis by the antibody or its fragments of the present invention.

In the case of using a commercially available chemotaxis chamber, after diluting the antibody or its fragments of the present invention with a suitable culture medium, IL-8 is added to the chamber followed by the addition of the diluted antibody or fragments. Next, the prepared neutrophil suspension is added to the chamber and allowed to stand for a certain period of time. Since migrating neutrophils adhere to the filter installed in the chamber, the number of such neutrophils may be measured by ordinary methods such as staining or fluorescent antibody methods. In addition, measurement may also be performed by microscopic evaluation using a microscope or by automated measurement using a machine.

After sterilizing by filtration using a membrane filter, the chimeric antibody, reshaped human antibody and its F(ab')$_2$, Fab, Fv or single chain Fv fragment against human IL-8 of the present invention can be administered as a pharmaceutical therapeutic agent preferably parenterally, by for example intravenous injection, intramuscular injection, intraperitoneal injection or subcutaneous injection, or transtracheally, by for example using a nebulizer. Although varying according to the age and symptoms of the patient, the normal dose in humans is 1–1000 mg/body, for which divided doses of 1–10 mg/kg/week can be selected.

After evaluating their purified binding activity, the chimeric antibody, reshaped human antibody and its F(ab')$_2$, Fab, Fv or single chain Fv fragment against human IL-8 of the present invention can be prepared into a pharmaceutical therapeutic agent by methods routinely used for making preparations of physiologically active proteins. For example, a preparation for injection consists of dissolving refined chimeric antibody, reshaped human antibody or its F(ab')$_2$, Fab, Fv or single chain Fv fragment against human IL-8 in a a solvent such as physiological saline or buffer, followed by the addition of an anti-adsorption agent such as Tween 80, gelatin or human serum albumin (HSA). Alternatively, this preparation may also be freeze-dried for dissolution and reconstitution prior to use. Examples of vehicles that can be used for freeze-drying include sugar-alcohols or sugars such as mannitol and glucose.

EXAMPLES

Although the following provides a detailed explanation of the present invention through its embodiments described below, the scope of the present invention is not limited by these examples.

Example 1

Cloning of DNA Coding for the V Region of Mouse Monoclonal Antibody Against Human IL-8

DNA that codes for the variable region of mouse monoclonal antibody against human IL-8 was cloned in the manner described below.

1. Preparation of Total RNA

Total RNA was prepared from hybridoma WS-4 by modifying the cesium chloride density gradient centrifugation method of Chirgwin, J. M. et al. described in Biochemistry, 18, 5294–5299, 1979.

Namely, 1×10$^7$ hybridoma WS-4 cells were completely homogenized in 25 ml of 4 M guanidine thiocyanate (Fluka). The homogenate was layered over a 5.7 M cesium chloride solution in a centrifuge tube followed by precipitation of the RNA by centrifuging for 14 hours at 20° C. at 31,000 rpm in a Beckman SW40 rotor.

The RNA precipitate was washed with 80% ethanol and then dissolved in 200 μl of 20 mM Tris-HCl (pH 7.5) containing 10 mM EDTA and 0.5% sodium N-laurylsarcosinate. After adding Protenase (Boehringer) to a concentration of 0.5 mg/ml, the resulting mixture was incubated in a water bath for 30 minutes at 37° C. The mixture was extracted with phenol and chloroform and the RNA was precipitated with ethanol. Next, the RNA precipitate was dissolved in 200 μl of 10 mM Tris-HCl (pH 7.5) containing 1 mM EDTA.

2. Extraction of Messenger RNA (mRNA)

In order to extract mRNA coding for the H chain of mouse monoclonal antibody WS-4, poly(A)-positive mRNA was extracted from the total RNA obtained step 1 above using the Fast Track mRNA Isolation Kit Version 3.2 (Invitrogen) and following the procedure described in the manufacturer's instructions.

3. Synthesis of Single Stranded cDNA

Single stranded cDNA was synthesized from approximately 40 ng of the mRNA obtained in step 2 above using the cDNA Cycle Kit (Invitrogen) and following the procedure described in the instructions. The resultant product was then used to amplify cDNA that codes for mouse H chain V region. Furthermore, in order to amplify cDNA that codes for mouse L chain V region, single stranded cDNA was synthesized from approximately 10 μg of the above-mentioned total RNA.

4. Amplification of Gene Coding for Antibody Variable Region by PCR (1) Amplication of cDNA Coding for Mouse H Chain V Region MHV (mouse heavy variable) primers 1 to 12 shown in SEQ ID NOs:13 to 24 and MHC (mouse heavy constant) primer shown in SEQ ID NO:25 (Jones, S. T. et al., Bio/Technology, 9, 88–89, 1991) were used for the PCR primers. 100 μl of PCR solution containing 10 mM Tris-HCl (pH 8.3), 50 mM KCl, 0.1 mM dNTPs (DATP, dGTP, dCTP, dTTP), 1.5 mM MgCl$_2$, 0.001% (w/v) gelatin, 5 units of DNA polymerase AmpliTaq (Perkin Elmer Cetus), 0.25 μM of one of the MHV primers shown in SEQ ID NOs:13 to 24, 75 μM of the MCH primer shown in SEQ ID NO:25, and 1.5 μl of the single stranded cDNA solution obtained in step 3 above. PCR solutions were prepared for each of the MHV primers 1–12. After covering each solution with 50 μl of mineral oil, it was heated in the order of 3 minutes at the initial temperature of 94° C., followed by a cycle of 1 minute at 94° C., 1 minute at 55° C. and 1 minute at 72° C. After repeating this heating cycle 30 times, the reaction mixture was further incubated for 10 minutes at 72° C.

(2) Amplification of cDNA Coding for Mouse L Chain V Region

MKV (mouse kappa variable) primers 1 to 11 shown in SEQ ID NOs:1 to 11 and MKC (mouse kappa constant) primer shown in SEQ ID NO:12 (Jones, S. T. et al., Bio/Technology, 9, 88–89, 1991) were used for the PCR primers.

Amplification of cDNA was performed from 2.0 μl of the single stranded cDNA obtained in step 3 above using the same method as that described for amplification of H chain V region gene in step 4 part (1) above with the exception that amplification was performed using 0.25 μM each of the MKV primer mixtures and 3.0 μM of MCK primer.

5. Purification and Fragmentation of PCR Product

The respective DNA fragments of the H chain V region and L chain V region amplified by PCR as described above were separated by agarose gel electrophoresis using 1.5% low melting point agarose (Sigma). Agarose pieces containing an H chain DNA fragment approximately 450 bp in length and an L chain DNA fragment approximately 400 bp in length were separately cut out and melted for 5 minutes at 65° C. followed by the addition of an equal volume of 20 mM Tris-HCl (pH 7.5) containing 2 mM EDTA and 300 mM NaCl.

This mixture was extracted by phenol and chloroform, the DNA fragments were recovered by ethanol precipitation, and dissolved in 10 mM Tris-HCl (pH 7.5) containing 1 mM EDTA. Next, the fragments were digested for 3 hours at 37° C. using 5 units of restriction enzyme XmaI (New England BioLabs) in 10 mM Tris-HCl (pH 7.9) containing 10 mM MgCl$_2$ and 1 mM dithiothreitol. Next, the DNA fragments were digested for 2 hours at 37° C. with 40 units of restriction enzyme SalI (Takara Shuzo), and the resulting DNA fragments were separated by agarose gel electrophoresis using 1.5% low melting point agarose (Sigma).

The agarose pieces containing DNA fragments were cut out and melted for 5 minutes at 65° C. followed by the addition of an equal volume of 20 mM Tris-HCl (pH 7.5) containing 2 mM EDTA and 300 mM NaCl. This mixture was then extracted from phenol and chloroform, the DNA fragments were recovered by ethanol precipitation and dissolved in 10 mM Tris-HCl (pH 7.5) containing 1 mM EDTA.

Thus, a DNA fragment containing a gene that codes for mouse κ-type L chain V region, and a DNA fragment containing a gene that codes for mouse H chain V region were respectively obtained. The above-mentioned DNA fragments both have an SalI attachment site at their 5' terminus, and an XmaI attachment site at their 3' terminus.

6. Linkage and Transformation

Approximately 0.3 μg of the SalI-XmaI DNA fragment containing gene that codes for mouse kappa-type L chain V region prepared in the manner described above were mixed with approximately 0.1 μg of pUC19 vector (Takara Shuzo), prepared by digesting with SalI, XmaI and alkaline phosphatase of *Escherichia coli* (BAP; Takara Shuzo), for 4 hours at 16° C. in a buffered reaction mixture containing 1 unit of T4 DNA ligase (Gibco BRL) and added suplemented buffer to link.

Next, 5 μl of the above-mentioned linkage mixture were added to 50 μl of competent cells of *E. coli* DH5α (GIBCO BRL) after which the cells were allowed to stand for 30 minutes on ice, for 1 minute at 42° C. and again for 1 minute on ice. Next, 400 μl of 2× YT medium (Molecular Cloning: A Laboratory Manual, Sambrook, et al., Cold Spring Harbor Laboratory Press, 1989) were added. After incubating for 1 hour at 37° C, the *E. coli* was spread onto 2× YT agar medium (Molecular Cloning: A Laboratory Manual, Sambrook, et al., Cold Spring Harbor Laboratory Press, 1989) containing 50 μg/ml of ampicillin (Meiji Seika) followed by incubation overnight at 37° C. to obtain the *E. coli* transformant.

Subsequently, 50 μg of X-Gal (5-bromo-4-chloro-3-indolyl-β-D-galactoside, Takara Shuzo) were applied as selection marker at this time.

This transformant was incubated overnight at 37° C. in 10 ml of 2× YT medium containing 50 μg/ml of ampicillin, and plasmid DNA was prepared from this culture using the QIAGEN Plasmid Mini Kit (QIAGEN) and following the procedure described in the instructions.

The plasmid containing gene that codes for mouse κ-type L chain V region originating in hybridoma WS-4 obtained in this manner was named pUC-WS4-VL.

A plasmid containing gene that codes for mouse H chain V region derived from hybridoma WS-4 was prepared from SalI-XmaI DNA fragments by following the same method as described above with the exception of using JM109 for the *E. coli* competent cells. The resulting plasmid was named pUC-WS4-VH.

Example 2

Determination of DNA Nucleotide Sequence

The nucleotide sequence of the cDNA coding region in the above-mentioned plasmids was determined using M13 Primer RV and M13 Primer M4 (both Takara Shuzo) as sequence primers, an automated DNA sequencer (Applied Biosystems Inc.) and the Taq Dye Deoxy Terminator Cycle Sequencing Kit (Applied Biosystems Inc.) and following the protocol specified by the manufacturers. The nucleotide sequence of the gene that codes for the L chain V region of mouse WS-4 antibody contained in plasmid pUC-WS4-VL is shown in SEQ ID NO:26. In addition, the nucleotide sequence of the gene that codes for the H chain V region of mouse WS-4 antibody contained in plasmid pUC-WS4-VH is shown in SEQ ID NO:28.

Example 3

Determination of CDR

The basic structure of the V regions of the L and H chains has mutual similarities, each having four framework regions linked by three hyper variable regions, namely complementarity determining regions (CDR). Although the amino acid sequence of the framework region is relatively well preserved, the variability of the amino acid sequence of the CDR regions is extremely high (Kabat, E. A. et al., "Sequences of Proteins of Immunological Interest", U.S. Dept. of Health and Human Services, 1991).

On the basis of this fact, the CDR were determined as shown in Table 5 by investigating their homology by attempting to match the amino acid sequence of the variable region of mouse monoclonal antibody to human IL-8 with the database of amino acid sequences of antibodies prepared by Kabat, et al.

TABLE 5

CDR in the L Chain V Region and H Chain V Region of Mouse WS-4 Antibody

| Plasmid | Sequence Number | CDR1 | CDR2 | CDR3 |
|---|---|---|---|---|
| pUC-WS4-VL | 26 | 24–34 | 50–56 | 89–97 |
| pUC-WS4-VH | 29 | 31–35 | 50–68 | 101–111 |

Example 4

Confirmation of Expression of Cloned cDNA (Preparation of Chimeric WS-4 Antibody)

Preparation of Expression Vector

In order to prepare a vector that expresses chimeric WS-4 antibody, cDNA clones pUC-WS4-VL and pUC-WS4-VH, which code for the L chain and H chain V regions of mouse WS-4, respectively, were modified by PCR. These were then introduced into HEF expression vector (refer to that previously described, WO92–19759 and and FIG. 1).

The backward primer (SEQ ID NO:30) for the L chain V region and the backward primer (SEQ ID NO:31) for the H chain V region were respectively hybridized to DNA that codes for the start of the leader sequence of the V region, and designed to have a Kozak consensus sequence (Kozak, M. et al., J. Mol. Biol., 196, 947–950, 1987) and a HindIII restriction site. The forward primer (SEQ ID NO:32) for the L chain V region and the forward primer (SEQ ID NO:33) for the H chain V region were hybridized to a DNA sequence that codes for the terminal of the J chain, and designed to add a splice donor sequence and BamHI restriction site.

100 μl of PCR reaction mixture containing 20 mM Tris-HCl (pH 8.2), 10 mM KCl, 6 mM $(NH_4)_2SO_4$, 1% Triton X-100, 100 μM dNTPs, 1.5 mM $MgCl_2$, 100 pmoles of each primer, 100 ng of template DNA (pUC-VL or pUC-VH) and 2.5 U of AmpliTaq enzyme, were covered with 50 μl of mineral oil. After initially denaturing for 3 minutes at 94° C., a heating cycle consisting of 1 minute at 94° C., 1 minute at 55° C. and 1 minute at 72° C. was repeated 30 times followed by final incubation for 10 minutes at 72° C.

The PCR product was purified using 1.5% low melting point agarose gel followed by digestion with HindIII and BamHI. The L chain V region was cloned into HEF expression vector HEF-VL-gκ, while the H chain V region was cloned into HEF expression vector HEF-VH-gγ1. After determining the DNA sequences, plasmids containing the DNA fragment having the correct DNA sequence were named HEF-chWS4L-gκ and HEF-chWS4H-gγ1 respectively.

Transfection into COS Cells

In order to observe the transient expression of chimeric WS-4 antibody, the above-mentioned expression vectors were tested in COS cells. HEF-chWS4L-gκ and HEF-chWS4H-gγ1 were simultaneously transfected into COS cells by electroporation using the Gene Pulser system (BioRad). Each DNA (10 μg) was added to 0.8 ml of aliquot containing $1 \times 10^7$ cells/ml in PBS, and then pulsed at 1.5 kV with a capacitance of 25 μF.

After allowing a recovery period of 10 minutes at room temperature, the electroporated cells were suspended in 15 ml of DMEM culture medium (GIBCO) containing 5% γ-globulin-free fetal bovine serum placed in a tissue culture dish. After incubating for 96 hours, the culture medium was collected, cell debris were removed by centrifugation, and the supernatant was then filtered with a disk filter having a pore diameter of 0.45 μm (Gelman Science).

ELISA

ELISA plates for measurement of antigen binding and antibody concentration were prepared as described below. The ELISA plates for measurement of antigen binding activity were prepared in the following manner. After forming a solid layer in each well of a 96-well plate (Nunc) with 100 μl of goat anti-human IL-8 polyclonal antibody (R & D Systems) dissolved in a solid layer of buffer at a concentration of 2 μg/ml (0.1 M sodium bicarbonate, 0.02% sodium azide), and blocking with 200 μl of dilution buffer (50 mM Tris-HCl (pH 7.2), 1% bovine serum albumin (BSA), 1 mM $MgCl_2$, 0.15 M NaCl, 0.05% Tween 20, and 0.02% sodium azide), 100 μl of recombinant human IL-8 (Amersham) (5 ng/ml) was added.

A purified sample of chimeric antibody or culture supernatant of COS cells that expressed these was serially diluted and added to each well. Next, 100 μl of alkaline phosphatase-labeled goat anti-human IgG antibody (TAGO) (1 μg/ml) were added. After incubation and washing, substrate solution (1 mg/ml p-nitrophenyl-phosphate) was added followed by measurement of absorbance at 405 nm.

For measurement of antibody concentration, after forming a solid layer in the wells of a 96-well plate with 100 μl of goat anti-human IgG antibody (TAGO) at a concentration of 1 μg/ml and blocking, a purified sample of chimeric antibody or culture medium of COS cells that expressed these was serially diluted and added to each well. Next, 100 μl of alkaline phosphatase-labeled goat anti-human IgG antibody (TAGO) (1 μg/ml) was added. After incubation and washing, substrate solution (1 mg/ml p-nitrophenylphosphate) was added and absorbance was measured at 405 nm.

As a result, since the chimeric antibody WS-4 showed specific binding to IL-8, it was considered that this chimeric antibody has the correct structure of the V region of mouse monoclonal antibody WS-4 (see FIG. 2).

Furthermore, the Escherichia coli having above-mentioned plasmid HEF-chWS4L-gκ was deposited as Escherichia coli DH5α (HEF-chWS4L-gκ), and the Escherichia coli having the above-mentioned plasmid HEF-chWS4H-gγ1 was deposited as Escherichia coli JM109 (HEF-chWS4H-gγ1) at the Bioengineering Industrial Technology Research Institute of the Agency of Industrial Science and Technology (1-1-3 Higashi, Tsukuba, Ibaraki, Japan) on Jul. 12, 1994 under the respective names FERM BP-4739 and FERM BP-4740 in accorrdance the provisions of the Budapest Convention.

Example 5

Preparation of Reshaped Human WS-4 Antibody

Preparation of the H Chain V Region of Reshaped Human WS-4 Antibody

DNA that codes for the H chain V region of reshaped human WS-4 antibody was designed in the manner described below. Complete DNA that codes for the H chain V region of reshaped human WS-4 antibody was designed so that known DNA sequences that respectively code for FR1 through FR3 of human antibody VDH26 and FR4 of human antibody 4B4 are linked to the DNA sequence that codes for the CDR of the H chain V region of mouse WS-4 antibody.

Next, a HindIII recognition site/Kozak consensus sequence and BamHI recognition site/splice donor sequence were respectively added to the 5' and 3' sides of this DNA sequence, followed by introduction into an HEF expression vector. The DNA sequence designed in this manner was then divided into four approximately equal oligonucleotides after which the secondary structure of those oligonucleotides for which there is the possibility of obstructing the assembly of these oligonucleotides were analyzed by computer.

The four oligonucleotide sequences are shown in SEQ ID NOs:34 to 37. These oligonucleotides have lengths of 113 to 143 bases, and adjacent oligonucleotides have an overlap region mutually consisting of 20 bases. HF1 (SEQ ID NO:34) and HF3 (SEQ ID NO:36) of these four oligonucleotides have a sense DNA sequence, while the other HF2 (SEQ ID NO:35) and HF4 (SEQ ID NO:37) have an antisense DNA sequence. These oligonucleotides were synthesized by an automated DNA synthesizer (Applied Biosystems).

In addition, the method of assembly of these four oligonucleotides by PCR is illustrated in FIG. 3. Approximately 100 ng each of HF1 and HF2 as well as HF3 and HF4 were combined and added to a PCR reaction mixture having a final volume of 98 μl and containing 2.5 U of Pfu DNA polymerase. After initially denaturing for 3 minutes at 94° C., the solutions were incubated for 2 cycles each cycle consisting of incubation for 2 minutes at 94° C., 2 minutes at 55° C. and 2 minutes at 72° C.

After mutually replacing half the volume of the PCR reaction solutions, incubation was continued for an additional two cycles. After adding 100 pmoles each of RVH5' primer (SEQ ID NO:38) and RVH3' primer (SEQ ID NO:39) as external primers, the PCR reaction solutions were covered with 50 μl of mineral oil. After initially denaturing for 3 minutes at 94° C., the reaction solutions were incubated for 45 cycles of 1 minute at 94° C., 1 minute at 55° C. and 1 minute at 72° C., followed finally by incubation for 10 minutes at 72° C.

A DNA fragment containing approximately 450 base pairs was purified on a 1.5% low melting point agarose gel, digested with HindIII and BamHI and cloned into HEF expression vector HEF-VH-gγ1 (FIG. 1). After determining the DNA sequence using EF-1 primer (SEQ ID NO:78) and HIP primer (SEQ ID NO:79), the plasmid that contained a DNA fragment that codes for the correct amino acid sequence of the H chain V region was named HEF-RVHa-gγ1. The amino acid sequence and nucleotide sequence of the H chain V region contained in this plasmid HEF-RVHa-gγ1 are shown in SEQ ID NOs:41 and 40, respectively.

Each of the versions "b", "c", "d", "e", "f", "g" and "h" of the H chain V region of reshaped human WS-4 antibody was prepared in the manner described below.

Version "b" (RVHb) was amplified by PCR using mutagen primers LTW1 (SEQ ID NO:42) and LTW2 (SEQ ID NO:43), designed so that leucine at position 47 was replaced by tryptophan, RVH5' (SEQ ID NO:38) and RVH3' (SEQ ID NO:39) for the primers that define both ends, and plasmid HEF-RVHa-gγ1 as the template DNA to obtain plasmid HEF-RVHb-gγ1. The amino acid sequence and nucleotide sequence of the H chain V region contained in this plasmid HEF-RVHb-gγ1 are shown in SEQ ID NO:45 and 44, respectively.

Version "c" was amplified by PCR using mutagen primers QTP1 (SEQ ID NO:46) and QTP2 (SEQ ID NO:47), designed so that glutamic acid at position 41 was replaced by proline, and plasmid HEF-RVHa-gγ1. as the template DNA to obtain plasmid HEF-RVHc-gγ1. The amino acid sequence and nucleotide sequence of the H chain V region contained in this plasmid HEF-RVHc-gγ1 are shown in SEQ ID NO:49 and 48, respectively.

Version "d" was amplified by PCR using mutagen primers QTP1 and QTP2 and plasmid HEF-RVHb-gγ1 as the template DNA to obtain plasmid HEF-RVHd-gγ1. The amino acid sequence and nucleotide sequence of the H chain V region contained in this plasmid HEF-RVHd-gγ1 are shown in SEQ ID NO:51 and 50, respectively.

Version "e" was amplified by using mutagen primers ATP1 (SEQ ID NO:52) and ATP2 (SEQ ID NO:53), designed so that alanine at position 40 was replaced by proline, and plasmid HEF-RVHd-gγ1 as the template DNA to obtain plasmid HEF-RVHe-gγ1. The amino acid sequence and nucleotide sequence of the H chain V region contained in this plasmid HEF-RVHe-gγ1 are shown in SEQ ID NO:55 and 54, respectively.

Version "f" was amplified using mutagen primers GTA1 (SEQ ID NO:56) and GTA2 (SEQ ID NO:57), designed so that glycine at position 44 was replaced by alanine, and plasmid HEF-RVHd-gγ1 for the template DNA to obtain plasmid HEF-RVHf-gγ1. The amino acid sequence and nucleotide sequence of the H chain V region contained in this plasmid HEF-RVHf-gγ1 are shown in SEQ ID NO:59 and 58, respectively.

Version "g" was amplified using mutagen primers LTF1 (SEQ ID NO:60) and LTF2 (SEQ ID NO:61), designed so that leucine at position 67 was replaced by phenylalanine, and plasmid HEF-RVHd-gγ1 as the template DNA to obtain plasmid HEF-RVHg-gγ1. The amino acid sequence and nucleotide sequence of the H chain V region contained in this plasmid HEF-RVHg-gγ1 are shown in SEQ ID NO:63 and 62, respectively.

Version "h" was amplified using mutagen primers LTF1 and LTF2, and plasmid HEF-RVHb-gγ1 as the template DNA to obtain plasmid HEF-RVHh-gγ1. The amino acid sequence and nucleotide sequence of the H chain V region contained in this plasmid HEF-RVHh-gγ1 are shown in SEQ ID NO:65 and 64, respectively.

Preparation of L Chain V Region of Reshaped Human WS-4 Antibody

DNA that codes for the L chain V region of reshaped human WS-4 antibody was designed in the manner described below. Complete DNA that codes for the L chain V region of reshaped human WS-4 antibody was designed so that a DNA sequence that codes for the FR of human antibody REI is linked to the DNA sequence that codes for the CDR of the L chain V region of mouse WS-4 antibody.

Next, a HindIII recognition site/Kozak consensus sequence and BamHI recognition site/splice donor sequence were respectively added to the 5' and 3' sides of this DNA sequence so as to enable it to be introduced into an HEF expression vector. The DNA sequence designed in this manner was then divided into four approximately equal oligonucleotides after which the secondary structure of those oligonucleotides for which there is the possibility of obstructing the assembly of these oligonucleotides were analyzed by computer.

The four oligonucleotide sequences are shown in SEQ ID NOs:66 to 69. These oligonucleotides have lengths of 106 to 124 bases, and adjacent oligonucleotides have an overlap region mutually consisting of 19 to 23 bases. LF1 (SEQ ID NO:66) and LF3 (SEQ ID NO:68) of these four oligonucleotides have a sense DNA sequence, while the other LF2 (SEQ ID NO:67) and LF4 (SEQ ID NO:69) have an anti-sense DNA sequence. These oligonucleotides were synthesized using the same method as that employed for the above-mentioned HF1 through HF4.

For assembly, after initially denaturing 98 μl of a PCR mixture containing 100 ng of each of the four types of the nucleotides and 5 U of Ampli Taq for 3 minutes at 94° C., the mixture was incubated for 2 cycles, each cycle consisting of incubation for 2 minutes at 94° C., 2 minutes at 55° C. and 2 minutes at 72° C. After adding 100 pmoles each of RVL5' primer (SEQ ID NO:70) and RVL3' primer (SEQ ID NO:71) as external primers, the PCR reaction mixture was covered with 50 μl of mineral oil. After initially denaturing for 3 minutes at 94° C., the reaction solution was incubated for 30 cycles of 1 minute at 94° C., 1 minute at 55° C. and 1 minute at 72° C., followed finally by incubation for 10 minutes at 72° C. (see FIG. 3).

A DNA fragment containing approximately 400 base pairs was purified using 1.5% low melting point agarose gel, digested with HindIII and BamHI and cloned into HEF expression vector HEF-VL-gκ (FIG. 1). After determining the DNA sequence using EF-1 primer (SEQ ID NO:78) and KIP primer (SEQ ID NO:80), the plasmid that contained a DNA fragment that codes for the correct amino acid sequence of the L chain V region was named HEF-RVLa-gκ. The amino acid sequence and nucleotide sequence of the L chain V region contained in this plasmid HEF-RVLa-gK are shown in SEQ ID NO:73 and 72, respectively.

Version "b" (RVLb) was amplified by PCR using mutagen primers FTY1 (SEQ ID NO:74) and FTY2 (SEQ ID NO:75), designed so that phenylalanine at position 71 was replaced by tyrosine, RVL5' (SEQ ID NO:70) and RVL3' (SEQ ID NO:71) for the primers that define both ends, and replaced by tyrosine, RVL5' (SEQ ID NO:70) and RVL3' (SEQ ID NO:71) for the primers that define both ends, and plasmid HEF-RVLa-gκ as the template DNA to obtain plasmid HEF-RVLb-gκ. The amino acid sequence and nucleotide sequence of the L chain V region contained in this plasmid HEF-RVLb-gκ are shown in SEQ ID NO:77 and 76, respectively.

Figure 4:
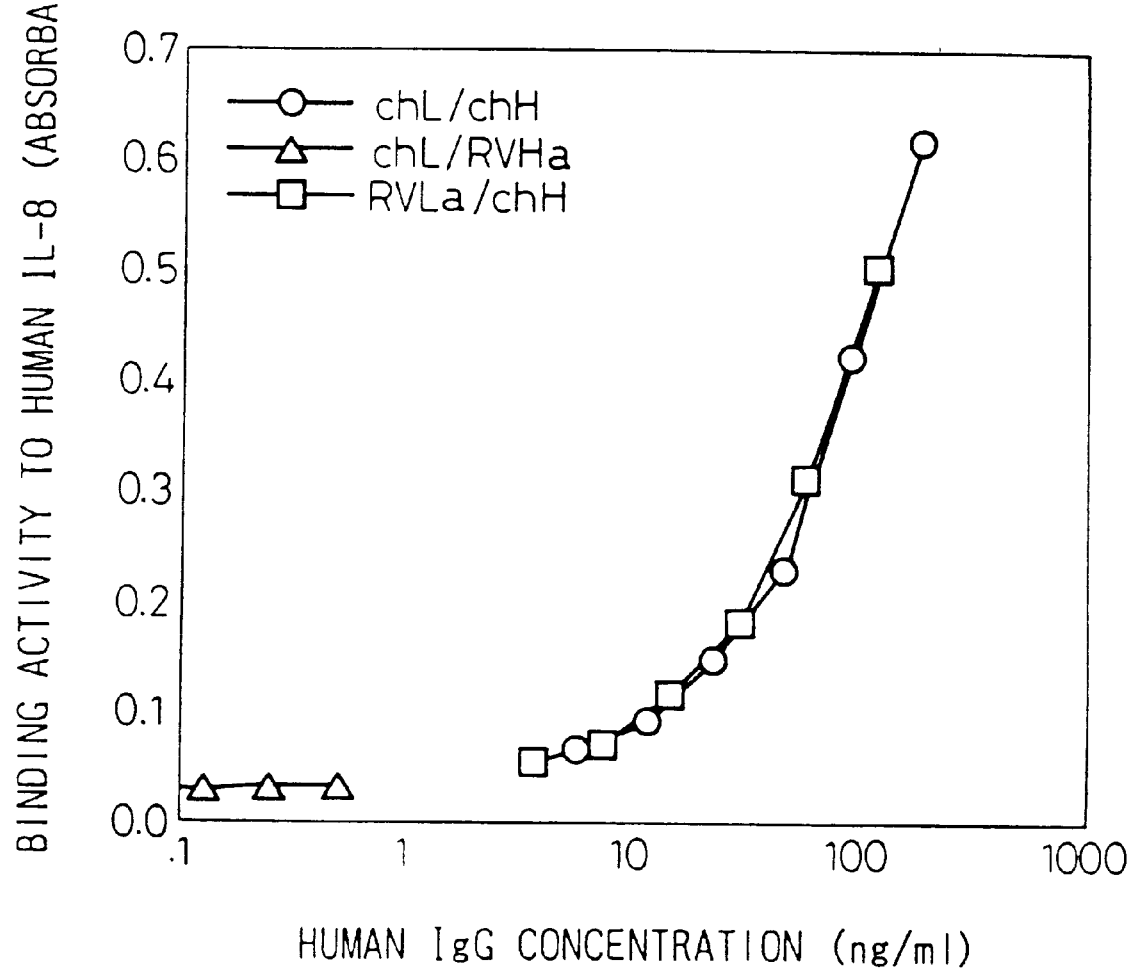
FIG. 4 is a graph indicating the results of ELISA for comparing the binding ability to human IL-8 of the L chain V region (RVLa) and the H chain V region (RVHa) of the reshaped human WS-4 antibody of the present invention in combination with, respectively, the H chain V region of chimeric WS-4 antibody (chH) and the L chain V region of chimeric WS-4 antibody (chL) expressed in COS cells, with that of the chimeric WS-4 antibody (chL/chH) of the present invention secreted into the culture medium of COS cells.

In order to evaluate the antigen binding activity of each chain of the reshaped human WS-4 antibody, COS cells were first simultaneously transfected in the manner previously described in relation to expression vector HEF-RVLa-gκ for version "a" of the L chain of reshaped human WS-4 antibody, and expression vector HEF-chWS4H-gγ1 for the H chain of chimeric WS-4 antibody. After collecting the culture medium as previously described, the amount of antibody produced and antigen binding activity were measured for the antibodies produced using the method described in the section on ELISA in the above Example 4. Those results are shown in FIG. 4. As shown in FIG. 4, it was confirmed that there was no difference in antigen binding activity between chimeric antibody (chL/chH), used as the positive control, and antibody consisting of a reshaped L chain and chimeric H chain (RVLa/chH).

At the same time, in order to evaluate the combination of expression vector HEF-chWS4L-gκ for the L chain of chimeric WS-4 antibody and version "a" of the H chain of reshaped human WS-4 antibody, both were simultaneously CO-transfected into COS cells and the amount of antibody produced and antigen binding activity were measured for the resulting antibody using the method described in the section on ELISA in the above Example 4. Antigen binding activity was not demonstrated for this antibody (chL/RVHa) (see FIG. 4).

As previously described, since version "a" of the L chain of reshaped human WS-4 antibody exhibited antigen binding activity equal to that of the L chain of chimeric cells with each version of the reshaped H chain and version "a" of the L chain of reshaped human WS-4 antibody (RVLa).

Figure 5:
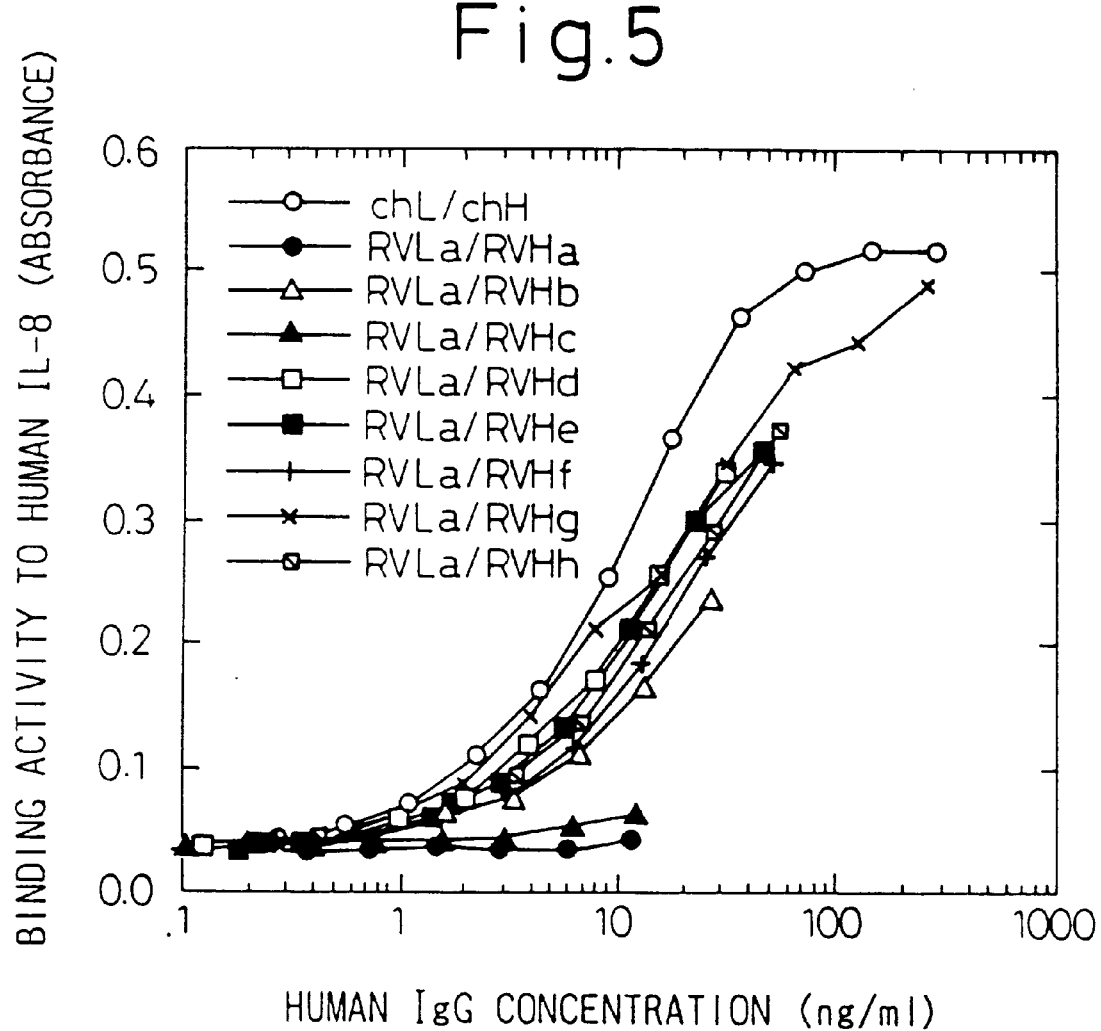
FIG. 5 is a graph indicating the results of ELISA for comparing the binding ability against human IL-8 of 8 types of reshaped human WS-4 antibody containing the RVLa of the present invention (RVLa/RVHa, RVLa/RVHb, RVLa/ RVHc, RVLa/RVHd, RVLa/RVHe, RVLa/RVHf, RVLa/ RVHg and RVLa/RVHh) secreted into the culture medium of COS cells, with that of the chimeric WS-4 antibody (chL/chH) of the present invention secreted into the culture medium of COS cells.

The result was that those antibodies having versions "b", "d", "e", "f", "g" and "h" of the reshaped H chain exhibited antigen binding activity comparable to that of chimeric WS-4 antibody (chL/chH) used as the positive control, thus indicating that this combination forms a functional antigen binding site in human antibody. However, with respect to the amount of antibody produced, all versions were produced in lesser amount than chimeric WS-4 antibody (chL/chH) with the exception of version "g" (RVHg). Furthermore, antigen binding activity was not observed in antibody having H chain version "c" (see FIG. 5).

Based on these findings, it was concluded that antibody having version "a" of the L chain of reshaped human WS-4 antibody (RVLa) and version "g" of the H chain of reshaped human WS-4 antibody reforms a functional antigen binding site that exhibits favorable antigen binding activity, and that the amount of antibody produced is comparable to chimeric WS-4 antibody (chL/chH) following simultaneous transfection into COS cells.

Figure 6:
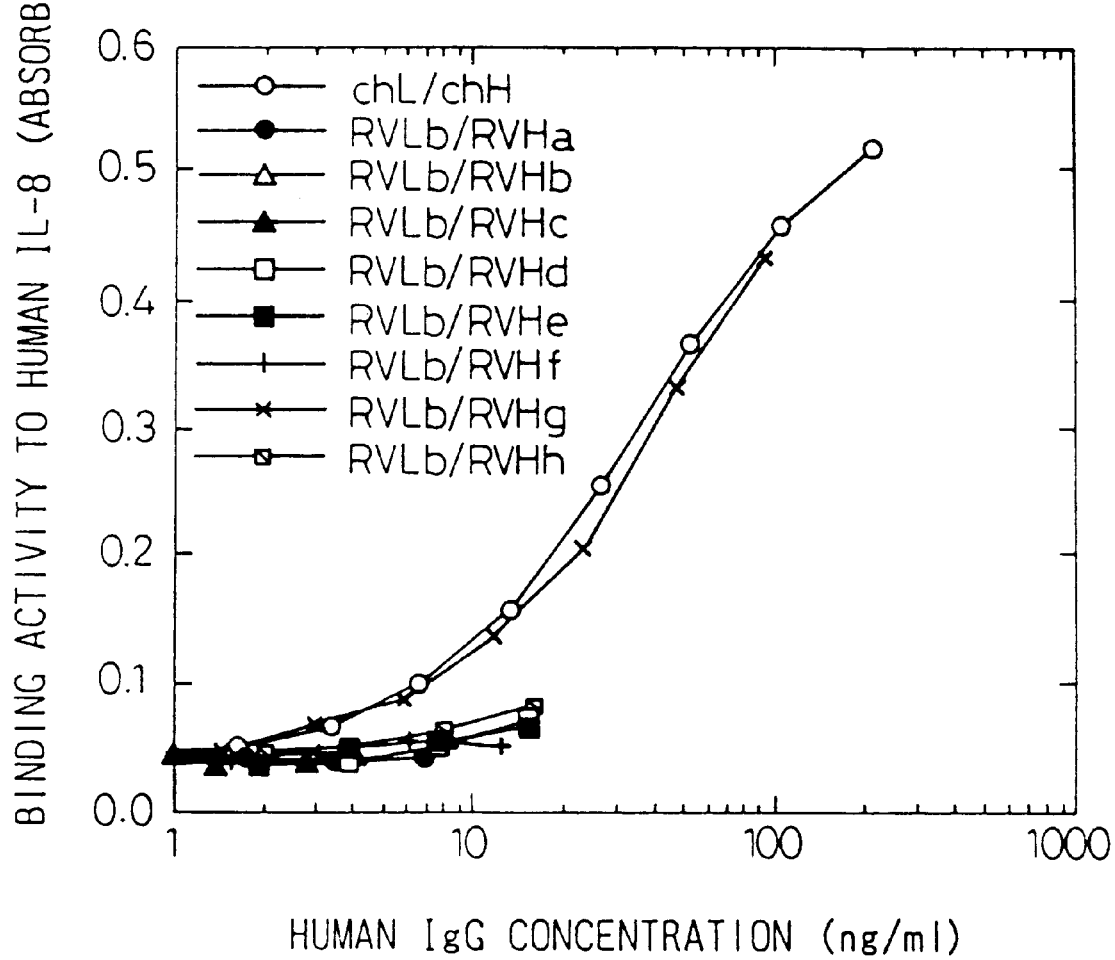
FIG. 6 is a graph indicating the results of ELISA for comparing the binding ability to human IL-8 of 8 types of reshaped human WS-4 antibody containing the second version RVLb of the present invention (RVLb/RVHa, RVLb/ RVHb, RVLb/RVHc, RVLb/RVHd, RVLb/RVHe, RVLb/ RVHf, RVLb/RVHg and RVLb/RVHh) produced in the culture supernatant of COS cells, with that of the chimeric WS-4 antibody (chL/chH) of the present invention secreted into the culture medium of COS cells.

Next, an evaluation of version "b" of the L chain of reshaped human WS-4 antibody (RVLb) was performed by simultaneously transfecting COS cells with each version of the H chain with version "b" of the L chain of reshaped human WS-4 antibody (RVLb). The result showed that only antibody having version "g" of the H chain of reshaped human WS-4 antibody (RVLb/RVHg) exhibited antigen binding activity comparable to chimeric WS-4 antibody (chL/chH) used as the positive control, and it was concluded that this combination forms a functional antigen binding site in human antibody. In addition, with respect to amount of antibody produced, all versions were produced in lesser amount than chimeric WS-4 antibody (chL/chH) with the exception of version "g" (RVHg) (see FIG. 6).

In the above-mentioned evaluation, the two types of reshaped human antibody (RVLa/RVHg and RVLb/RVHg) that exhibited binding activity to human IL-8 and extent of production comparable to that of chimeric WS-4 antibody (chL/chH) were respectively purified with a Protein A column, after which binding activity was evaluated accurately using the method described in the section-on ELISA in Example 4. The result showed that chimeric WS-4 antibody (chL/chH), RVLa/RVHg antibody and RVLb/RVHg antibody all exhibited the same extents of binding activity (see FIG. 7).

Based on these findings, it was concluded that antibody having either version "a" (RVLa) or version "b" (RVLb) of the L chain of reshaped human WS-4 antibody and version "g" (RVHg) of the H chain of reshaped human WS-4 antibody reforms a functional antigen binding site that a level of exhibits favorable antigen binding activity, and that a level of antibody production comparable to that of chimeric WS-4 antibody (chL/chH) was exhibited following simultaneous transfection into COS cells.

The inhibitory activity on IL-8 binding to IL-8 receptors of reshaped human antibody consisting of version "a" (RVLa) of the H chain and version "g" (RVHg) of the H chain of reshaped human WS-4 antibody, or version "b" (RVLb) of said L chain and version "g" (RVHg) of said H chain, was evaluated by ligand receptor binding inhibition assay.

Approximately 100 ml of heparinized blood sample from normal subjects was layered in 35 ml aliquots onto 15 ml of Mono-Poly separation solution (ICN Biomedicals), and the human neutrophil layer was isolated by centrifugation according to the instructions provided. After washing these cells with RPMI-1640 medium containing 1% BSA, contaminating erythrocytes were removed with 150 mM ammonium chloride solution. After centrifuging, the cells were washed with RPMI-1640 medium containing 1% BSA and resuspended at a concentration of $2 \times 10^7$ cells/ml. The neutrophil content of this cell suspension was found to be 95% or more as a result of measuring after staining smear specimens prepared using Cytospin (Shandon) with Diff-Quik stain (Green Cross).

The above-mentioned neutrophil suspension was centrifuged and resuspended at a concentration of $2 \times 10^7$ cells/ml with binding buffer (D-PBS containing 1% BSA and 0.1% sodium azide). At this time, SK2 chimeric antibody having an Fc portion identical to that of the human antibody of the present invention (see International Patent Application No. PCT/JP94/00859) and its antigen, human IL-6, were added to concentrations of approximately 50 μg/ml and approximately 40 ng/ml, respectively, and incubated for 30 minutes in an ice bath for the purpose of pre-saturating the Fc receptors on the neutrophils.

Figure 8:
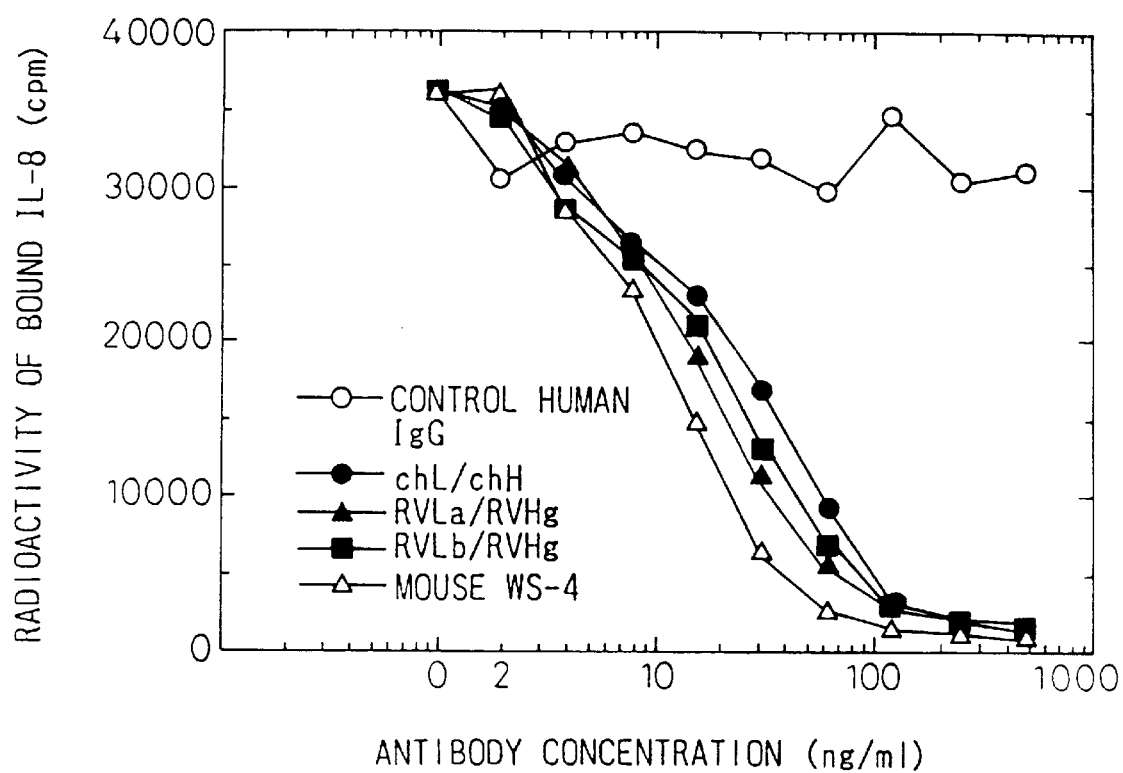
FIG. 8 is a graph indicating the results of ligand receptor binding inhibition assays for comparison of the ability to inhibit binding of IL-8 to the IL-8 receptor, of the purified reshaped human antibodies RVLa/RVHg and RVLb/RVHg of the present invention, with that of the mouse WS-4 antibody and the chimeric WS-4 antibody (chL/chH) of the present invention.

IL-8 radioactively labeled with $^{125}$I (74 TBq/mmol, Amersham) and non-labeled IL-8 (Amersham) prepared by mixing in binding buffer at concentrations of 4 ng/ml each. Chimeric WS-4 antibody (chL/chH), reshaped human antibody (RVLa/RVHg and RVLb/RVHg), negative control human antibody (PAESEL+LOREI) or positive control mouse WS-4 antibody was respectively diluted with binding buffer at concentrations between 2000 ng/ml and approximately 8 ng/ml in stepwise, 2-fold dilutions. 50 μl of IL-8 solution and 50 μl of each of the antibody solutions were incubated for 30 minutes in an ice bath. Next, 100 μl of the above-mentioned neutrophil suspension was added and incubation was continued further for 1 hour with mixing every 15 minutes. Following incubation, the cell suspension was layered onto 200 μl of 20% saccharose solution followed by centrifugation and freezing. In order to measure the IL-8 bound to the cells, the cell sediment was cut away and radioactivity was measured with a gamma counter (Aroka). Those results are shown in FIG. 8.

Antibody having version "a" of the L chain (RVLa) and version "g" of the H chain (RVHg) of reshaped human WS-4 antibody, or version "b" of said L chain and version "g" of said H chain, was clearly shown to have binding inhibitory activity comparable to that of chimeric antibody (chL/chH) in respect of the binding of IL-8 to IL-8 receptors.

Furthermore, the Escherichia coli having the above-mentioned plasmid HEF-RVLa-gκ was deposited as Escherichia coli DH5α (HEF-RVLa-gκ), and the Escherichia coli containing plasmid HEF-RVHg-gγ1 was deposited as Escherichia coli JM109 (HEF-RVHg-gγ1) at the Bioengineering Industrial Technology Research Institute of the Agency of Industrial Science and Technology (1-1-3 Higashi, Tsukuba, Ibaraki, Japan) on Jul. 12, 1994 under the respective names FERM BP-4738 and FERM BP-4741 based on the provisions of the Budapest Convention.

Reference Example 1

Preparation of Hybridoma WS-4

Hybridoma that produces anti-human IL-8 monoclonal antibody was prepared by fusing spleen cells of BALB/c mice immunized with human IL-8 and mouse myeloma cells P3x63-Ag8.653 according to routine methods using polyethylene glycol. Screening was performed using the activity of binding with human IL-8 as the criterion to establish the hybridoma WS-4 (Ko, Y. C. et al., J. Immunol. Methods, 149, 227–235, 1992).

INDUSTRIAL APPLICABILITY

The present invention provides reshaped human antibody against human IL-8, and in this antibody, the CDR of the V region of human antibody is substituted with the CDR of mouse monoclonal antibody against human IL-8. Since the majority of this reshaped human antibody is of human origin and CDR inherently having low antigenicity, the reshaped human antibody of the present invention has low antigenicity to humans, and for this reason can be expected to be useful in medical treatment.

List of Microorganisms Deposited under the Provisions of Article 13 bis of the Patent Cooperation Treaty International Deposit Authority:

Name: National Institute of Bioscience and Human-Technology Agency of Industrial Science and Technology Address: 1-3 Higashi 1-chome, Tsukuba, Ibaraki, Japan Deposit Numbers and Deposition Dates:

(1) *Escherichia coli* DH5α (HEF-RVLa-gκ) Deposit no.: FERM BP-4738 Deposition date: Jul. 12, 1994

(2) *Escherichia coli* DH5α (HEF-chWS4L-gκ) Deposit no.: FERM BP-4739 Deposition date: Jul. 12, 1994

(3) *Escherichia coli* JM109 (HEF-chWS4H-gγ1) Deposit no.: FERM BP-4740 Deposition date: Jul. 12, 1994

(4) *Escherichia coli* JM109 (HEF-RVHg-gγ1) Deposit no.: FERM BP-4741 Deposition date: Jul. 12, 1994

We claim:

1. A polynucleotide which comprises coding regions comprising a nucleotide sequence encoding a V region of an L chain and a V region of an H chain of a reshaped antibody or a fragment thereof that specifically binds human IL-8, wherein said V region of L chain comprises the amino acid sequence from Asp at position numbered 1 to Lys at position numbered 107 of SEQ ID NO: 73 (RVLa) and said V region of H chain comprises the amino acid sequence from Glu at position numbered 1 to Ser at position numbered 122 of SEQ ID NO: 63 (RVHg).

2. The polynucleotide of claim 1, wherein said coding regions further comprise a nucleotide sequence encoding a C region of an L chain and a C region of an H chain of a human antibody.

3. The polynucleotide of claim 1, wherein said coding regions are operably linked to control sequences which effect their expression.

4. The polynucleotide of claim 1, wherein said coding regions are operably linked to control sequences which effect their expression.

5. A recombinant host cell which contains the polynucleotide of claim 3.

6. A recombinant host cell which contains the polynucleotide of claim 4.

7. A method to produce an antibody that specifically binds human IL-8 or a fragment of said antibody, which method comprises culturing the cells of claim 5 under conditions wherein said coding regions are expressed to produce said antibody or said fragment.

8. A method to produce an antibody that specifically binds human IL-8 or a fragment of said antibody, which method comprises culturing the cells of claim 6 under conditions wherein said coding regions are expressed to produce said antibody or said fragment.

9. The method of claim 7, wherein said fragment is Fab, Fab', F(ab')$_2$, or single chain Fv.

10. The method of claim 8, wherein said fragment is Fab, Fab', F(ab')$_2$, or single chain Fv.

11. A polynucleotide which comprises coding regions comprising a nucleotide sequence encoding a variable (V) region of a light (L) chain of a reshaped antibody or a fragment thereof that specifically binds human IL-8, wherein said V region comprises the amino acid sequence from the Asp at position numbered 1 to the Lys at the position numbered 107 of SEQ ID NO: 73 (RVLa).

12. The polynucleotide of claim 11, wherein said coding regions further comprise a nucleotide sequence encoding a constant (C) region of an L chain of a human antibody.

13. The polynucleotide of claim 11, wherein said coding regions are operably linked to control sequences which effect their expression.

14. The polyucleotide of claim 12, wherein said coding regions are operably linked to control sequences which effect their expression.

15. A recombinant host cell which contains the polynucleotide of claim 13.

16. A recombinant host cell which contains the polynucleotide of claim 14.

17. A method to produce an antibody that specifically binds human IL-8 or a fragment of said antibody, which method comprises culturing the cells of claim 15 under conditions wherein said coding regions are expressed to produce said antibody or said fragment.

18. A method to produce an antibody that specifically binds human IL-8 or a fragment of said antibody, which method comprises culturing the cells of claim 16 under conditions wherein said coding regions are expressed to produce said antibody or said fragment.

19. The method of claim 17, wherein said fragment is Fab, Fab', F(ab')$_2$ or single chain Fv.

20. The method of claim 18, wherein said fragment is Fab, Fab', F(ab')$_2$ or single chain Fv.

21. A polynucleotide which comprises coding regions comprising a nucleotide sequence encoding a V region of a heavy (H) chain of a reshaped antibody or a fragment thereof that specifically binds human IL-8, wherein said V region comprises the amino acid sequence from the Glu at position numbered 1 to Ser at position numbered 122 of SEQ ID NO: 63 (RVHg).

22. The polynucleotide of claim 21, wherein said coding regions further comprise a nucleotide sequence encoding a C region of an H chain of a human antibody.

23. The polynucleotide of claim 22, wherein said coding regions are operably linked to control sequences which effect their expression.

24. The polynucleotide of claim 22, wherein said coding regions are operably linked to control sequences which effect their expression.

25. A recombinant host cell which contains the polynucleotide of claim 23.

26. A recombinant host cell which contains the polynucleotide of claim 24.

27. A method to produce an antibody that specifically binds human IL-8 or a fragment of said antibody, which method comprises culturing the cells of claim 25 under conditions wherein said coding regions are expressed to produce said antibody or said fragment.

28. A method to produce an antibody that specifically binds human IL-8 or a fragment of said antibody, which method comprises culturing the cells of claim 26 under conditions wherein said coding regions are expressed to produce said antibody or said fragment.

29. The method of claim 27, wherein said fragment is Fab, Fab', F(ab')$_2$, or single chain Fv.

30. The method of claim 28, wherein said fragment is Fab, Fab', F(ab')$_2$, or single chain Fv.

* * * * *

SEQUENCE LISTING (1) GENERAL INFORMATION:

(iii) NUMBER OF SEQUENCES: 105

(2) INFORMATION FOR SEQ ID NO:1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ix) FEATURE:
      (A) NAME/KEY: Other
      (B) LOCATION: 1...40
      (D) OTHER INFORMATION: MKV1 sequence (xi) SEQUENCE DESCRIPTION: SEQ ID NO:1:

ACTAGTCGAC ATGAAGTTGC CTGTTAGGCT GTTGGTGCTG          40

(2) INFORMATION FOR SEQ ID NO:2:

(i) SEQUENCE CHARACTERISTICS:
      (A) LENGTH: 39 base pairs
      (B) TYPE: nucleic acid
      (C) STRANDEDNESS: single
      (D) TOPOLOGY: linear (ix) FEATURE:
      (A) NAME/KEY: Other
      (B) LOCATION: 1...39
      (D) OTHER INFORMATION: MKV2 sequence (xi) SEQUENCE DESCRIPTION: SEQ ID NO:2:

ACTAGTCGAC ATGGAGWCAG ACACACTCCT GYTATGGGT           39

(2) INFORMATION FOR SEQ ID NO:3:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (ix) FEATURE:
    (A) NAME/KEY: Other
    (B) LOCATION: 1...40
    (D) OTHER INFORMATION: MKV3 sequence (xi) SEQUENCE DESCRIPTION: SEQ ID NO:3:

ACTAGTCGAC ATGAGTGTGC TCACTCAGGT CCTGGSGTTG                40

(2) INFORMATION FOR SEQ ID NO:4:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...43
        (D) OTHER INFORMATION: MKV4 sequence (xi) SEQUENCE DESCRIPTION: SEQ ID NO:4:

ACTAGTCGAC ATGAGGRCCC CTGCTCAGWT TYTTGGMWTC TTG            43

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...40
        (D) OTHER INFORMATION: MKV5 sequence (xi) SEQUENCE DESCRIPTION: SEQ ID NO:5:

ACTAGTCGAC ATGGATTTWC AGGTGCAGAT TWTCAGCTTC                40

(2) INFORMATION FOR SEQ ID NO:6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...37
        (D) OTHER INFORMATION: MKV6 sequence (xi) SEQUENCE DESCRIPTION: SEQ ID NO:6:

ACTAGTCGAC ATGAGGTKCY YTGYTSAGYT YCTGRGG                   37

(2) INFORMATION FOR SEQ ID NO:7:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: Other (B) LOCATION: 1...41
        (D) OTHER INFORMATION: MKV7 sequence (xi) SEQUENCE DESCRIPTION: SEQ ID NO:7:

ACTAGTCGAC ATGGGCWTCA AGATGGAGTC ACAKWYYCWG G                            41

(2) INFORMATION FOR SEQ ID NO:8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...41
        (D) OTHER INFORMATION: MKV8 sequence (xi) SEQUENCE DESCRIPTION: SEQ ID NO:8:

ACTAGTCGAC ATGTGGGGAY CTKTTTYCMM TTTTTCAATT G                            41

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...35
        (D) OTHER INFORMATION: MKV9 sequence (xi) SEQUENCE DESCRIPTION: SEQ ID NO:9:

ACTAGTCGAC ATGGTRTCCW CASCTCAGTT CCTTG                                   35

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...37
        (D) OTHER INFORMATION: MVK10 sequence (xi) SEQUENCE DESCRIPTION: SEQ ID NO:10:

ACTAGTCGAC ATGTATATAT GTTTGTTGTC TATTTCT                                 37

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...38
        (D) OTHER INFORMATION: MVK11 sequence (xi) SEQUENCE DESCRIPTION: SEQ ID NO:11:

ACTAGTCGAC ATGGAAGCCC CAGCTCAGCT TCTCTTCC                                38

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...27
        (D) OTHER INFORMATION: MKC sequence (xi) SEQUENCE DESCRIPTION: SEQ ID NO:12:

GGATCCCGGG TGGATGGTGG GAAGATG                                        27

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...37
        (D) OTHER INFORMATION: MHV1 sequence (xi) SEQUENCE DESCRIPTION: SEQ ID NO:13:

ACTAGTCGAC ATGAAATGCA GCTGGGTCAT STTCTTC                             37

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...36
        (D) OTHER INFORMATION: MHV2 sequence (xi) SEQUENCE DESCRIPTION: SEQ ID NO:14:

ACTAGTCGAC ATGGGATGGA GCTRTATCAT SYTCTT                              36

(2) INFORMATION FOR SEQ ID NO:15:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...37
        (D) OTHER INFORMATION: MHV3 sequence (xi) SEQUENCE DESCRIPTION: SEQ ID NO:15:

ACTAGTCGAC ATGAAGWTGT GGTTAAACTG GGTTTTT                             37

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear -continued (ix) FEATURE:
              (A) NAME/KEY: Other
              (B) LOCATION: 1...35
              (D) OTHER INFORMATION: MHV4 sequence (xi) SEQUENCE DESCRIPTION: SEQ ID NO:16:

ACTAGTCGAC ATGRACTTTG GGYTCAGCTT GRTTT                              35

(2) INFORMATION FOR SEQ ID NO:17:

(i) SEQUENCE CHARACTERISTICS:
              (A) LENGTH: 40 base pairs
              (B) TYPE: nucleic acid
              (C) STRANDEDNESS: single
              (D) TOPOLOGY: linear (ix) FEATURE:
              (A) NAME/KEY: Other
              (B) LOCATION: 1...40
              (D) OTHER INFORMATION: MHV5 sequence (xi) SEQUENCE DESCRIPTION: SEQ ID NO:17:

ACTAGTCGAC ATGGACTCCA GGCTCAATTT AGTTTTCCTT                         40

(2) INFORMATION FOR SEQ ID NO:18:

(i) SEQUENCE CHARACTERISTICS:
              (A) LENGTH: 37 base pairs
              (B) TYPE: nucleic acid
              (C) STRANDEDNESS: single
              (D) TOPOLOGY: linear (ix) FEATURE:
              (A) NAME/KEY: Other
              (B) LOCATION: 1...37
              (D) OTHER INFORMATION: MHV6 sequence (xi) SEQUENCE DESCRIPTION: SEQ ID NO:18:

ACTAGTCGAC ATGGCTGTCY TRGSGCTRCT CTTCTGC                            37

(2) INFORMATION FOR SEQ ID NO:19:

(i) SEQUENCE CHARACTERISTICS:
              (A) LENGTH: 36 base pairs
              (B) TYPE: nucleic acid
              (C) STRANDEDNESS: single
              (D) TOPOLOGY: linear (ix) FEATURE:
              (A) NAME/KEY: Other
              (B) LOCATION: 1...36
              (D) OTHER INFORMATION: MHV7 sequence (xi) SEQUENCE DESCRIPTION: SEQ ID NO:19:

ACTAGTCGAC ATGGRATGGA GCKGGRTCTT TMTCTT                             36

(2) INFORMATION FOR SEQ ID NO:20:

(i) SEQUENCE CHARACTERISTICS:
              (A) LENGTH: 33 base pairs
              (B) TYPE: nucleic acid
              (C) STRANDEDNESS: single
              (D) TOPOLOGY: linear (ix) FEATURE:
              (A) NAME/KEY: Other
              (B) LOCATION: 1...33
              (D) OTHER INFORMATION: MHV8 sequence (xi) SEQUENCE DESCRIPTION: SEQ ID NO:20:

ACTAGTCGAC ATGAGAGTGC TGATTCTTTT GTG                                33

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...40
        (D) OTHER INFORMATION: MHV9 sequence (xi) SEQUENCE DESCRIPTION: SEQ ID NO:21:

ACTAGTCGAC ATGGMTTGGG TGTGGAMCTT GCTATTCCTG          40

(2) INFORMATION FOR SEQ ID NO:22:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...37
        (D) OTHER INFORMATION: MHV10 sequence (xi) SEQUENCE DESCRIPTION: SEQ ID NO:22:

ACTAGTCGAC ATGGGCAGAC TTACATTCTC ATTCCTG             37

(2) INFORMATION FOR SEQ ID NO:23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...38
        (D) OTHER INFORMATION: MHV11 sequence (xi) SEQUENCE DESCRIPTION: SEQ ID NO:23:

ACTAGTCGAC ATGGATTTTG GGCTGATTTT TTTTATTG           38

(2) INFORMATION FOR SEQ ID NO:24:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...37
        (D) OTHER INFORMATION: MHV12 sequence (xi) SEQUENCE DESCRIPTION: SEQ ID NO:24:

ACTAGTCGAC ATGATGGTGT TAAGTCTTCT GTACCTG             37

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single (D) TOPOLOGY: linear (ix) FEATURE:
         (A) NAME/KEY: Other
         (B) LOCATION: 1...28
         (D) OTHER INFORMATION: MHC sequence (xi) SEQUENCE DESCRIPTION: SEQ ID NO:25:

GGATCCCGGG CCAGTGGATA GACAGATG                                                28

(2) INFORMATION FOR SEQ ID NO:26:

(i) SEQUENCE CHARACTERISTICS:
        (A) LENGTH: 382 base pairs
        (B) TYPE: nucleic acid
        (C) STRANDEDNESS: double
        (D) TOPOLOGY: linear (ii) MOLECULE TYPE: cDNA (ix) FEATURE:
         (A) NAME/KEY: Coding Sequence
         (B) LOCATION: 1...381
         (D) OTHER INFORMATION:
         (A) NAME/KEY: mat_peptide
         (B) LOCATION: 64...381
         (D) OTHER INFORMATION:
         (A) NAME/KEY: Signal Sequence
         (B) LOCATION: 1...63
         (D) OTHER INFORMATION:

(xi) SEQUENCE DESCRIPTION: SEQ ID NO:26:

```
ATG AGT GTG CTC ACT CAG GTC CTG GGG TTG CTG CTG CTG TGG CTT ACA        48
Met Ser Val Leu Thr Gln Val Leu Gly Leu Leu Leu Leu Trp Leu Thr
-20             -15                 -10                 -5

GGT GCC AGA TGT GAC ATC CAG ATG ACT CAG TCT CCA GCC TCC CTA TCT        96
Gly Ala Arg Cys Asp Ile Gln Met Thr Gln Ser Pro Ala Ser Leu Ser
                1               5                   10

GCA TCT GTG GGA GAA ACT GTC ACC ATC ACA TGT CGA GCA AGT GAG ATT       144
Ala Ser Val Gly Glu Thr Val Thr Ile Thr Cys Arg Ala Ser Glu Ile
            15                  20                  25

ATT TAC AGT TAT TTA GCA TGG TAT CAG CAG AAA CAG GGA AAA TCT CCT       192
Ile Tyr Ser Tyr Leu Ala Trp Tyr Gln Gln Lys Gln Gly Lys Ser Pro
30                  35                  40

CAG CTC CTG GTC TAT AAT GCA AAA ACC TTA GCA GAT GGT GTG TCA TCA       240
Gln Leu Leu Val Tyr Asn Ala Lys Thr Leu Ala Asp Gly Val Ser Ser
45                  50                  55                  60

AGG TTC AGT GGC AGT GGA TCA GGC ACA CAG TTT TCT CTG CGG ATC AGC       288
Arg Phe Ser Gly Ser Gly Ser Gly Thr Gln Phe Ser Leu Arg Ile Ser
                65                  70                  75

AGC CTG CAG CCT GAA GAT TTT GGG AGT TAT TAC TGT CAA CAT CAT TTT       336
Ser Leu Gln Pro Glu Asp Phe Gly Ser Tyr Tyr Cys Gln His His Phe
            80                  85                  90

GGT TTT CCT CGG ACG TTC GGT GGA GGC ACC AAG CTG GAA CTC AAA C         382
Gly Phe Pro Arg Thr Phe Gly Gly Gly Thr Lys Leu Glu Leu Lys
        95                  100                 105
```

(2) INFORMATION FOR SEQ ID NO:27:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
    (A) NAME/KEY: Signal Sequence
    (B) LOCATION: 1...20
    (D) OTHER INFORMATION:

(xi) SEQUENCE DESCRIPTION: SEQ ID NO:27:

```
Met Ser Val Leu Thr Gln Val Leu Gly Leu Leu Leu Trp Leu Thr
-20             -15             -10              -5

Gly Ala Arg Cys Asp Ile Gln Met Thr Gln Ser Pro Ala Ser Leu Ser
             1               5                  10

Ala Ser Val Gly Glu Thr Val Thr Ile Thr Cys Arg Ala Ser Glu Ile
         15                  20                  25

Ile Tyr Ser Tyr Leu Ala Trp Tyr Gln Gln Lys Gln Gly Lys Ser Pro
     30                  35                  40

Gln Leu Leu Val Tyr Asn Ala Lys Thr Leu Ala Asp Gly Val Ser Ser
45                  50                  55                  60

Arg Phe Ser Gly Ser Gly Ser Gly Thr Gln Phe Ser Leu Arg Ile Ser
             65                  70                  75

Ser Leu Gln Pro Glu Asp Phe Gly Ser Tyr Tyr Cys Gln His His Phe
             80                  85                  90

Gly Phe Pro Arg Thr Phe Gly Gly Gly Thr Lys Leu Glu Leu Lys
         95                  100                 105
```

(2) INFORMATION FOR SEQ ID NO:28:

(i) SEQUENCE CHARACTERISTICS:
        (A) LENGTH: 424 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...423
        (D) OTHER INFORMATION:
        (A) NAME/KEY: mat_peptide
        (B) LOCATION: 61...423
        (D) OTHER INFORMATION:
        (A) NAME/KEY: Signal Sequence
        (B) LOCATION: 1...60
        (D) OTHER INFORMATION:

(xi) SEQUENCE DESCRIPTION: SEQ ID NO:28:

```
ATG AAG TTG TGG TTA AAC TGG GTT TTT CTT GTG ACA CTT TTA AAT GGT        48
Met Lys Leu Trp Leu Asn Trp Val Phe Leu Val Thr Leu Leu Asn Gly
             -15             -10              -5

ATC CAG TGT GAG GTG AAA CTG GTG GAG TCT GGA GGA GGC TTG ATA CAG        96
Ile Gln Cys Glu Val Lys Leu Val Glu Ser Gly Gly Gly Leu Ile Gln
             1               5                  10

CCT GGG GAT TCT CTG AGA CTC TCC TGT GTA ACC TCT GGG TTC ACC TTC       144
Pro Gly Asp Ser Leu Arg Leu Ser Cys Val Thr Ser Gly Phe Thr Phe
         15                  20                  25

AGT GAT TAC TAC CTG AGC TGG GTC CGC CAG CCT CCA GGA AAG GCA CTT       192
Ser Asp Tyr Tyr Leu Ser Trp Val Arg Gln Pro Pro Gly Lys Ala Leu
30                  35                  40                  45

GAG TGG GTG GGT CTC ATT AGA AAC AAA GCC AAT GGT TAC ACA AGA GAG       240
Glu Trp Val Gly Leu Ile Arg Asn Lys Ala Asn Gly Tyr Thr Arg Glu
             50                  55                  60

TAC AGT GCA TCT GTG AAG GGT CGG TTC ACC ATC TCC AGA GAT GAT TCC       288
Tyr Ser Ala Ser Val Lys Gly Arg Phe Thr Ile Ser Arg Asp Asp Ser
         65                  70                  75

CAA AGC ATC CTC TAT CTT CAA ATG AAC ACC TTG AGA GGT GAG GAC AGT       336
Gln Ser Ile Leu Tyr Leu Gln Met Asn Thr Leu Arg Gly Glu Asp Ser
         80                  85                  90
```

```
GCC ACT TAT TAC TGT GCA CGA GAG AAC TAT AGG TAC GAC GTA GAG CTT       384
Ala Thr Tyr Tyr Cys Ala Arg Glu Asn Tyr Arg Tyr Asp Val Glu Leu
    95                  100                 105

GCT TAC TGG GGC CAA GGG ACT CTG GTC ACT GTC TCT GCA G                 424
Ala Tyr Trp Gly Gln Gly Thr Leu Val Thr Val Ser Ala
110             115                 120
```

(2) INFORMATION FOR SEQ ID NO:29:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:29:

```
Met Lys Leu Trp Leu Asn Trp Val Phe Leu Val Thr Leu Leu Asn Gly
            -15                 -10                 -5

Ile Gln Cys Glu Val Lys Leu Val Glu Ser Gly Gly Gly Leu Ile Gln
                1               5                   10

Pro Gly Asp Ser Leu Arg Leu Ser Cys Val Thr Ser Gly Phe Thr Phe
    15                  20                  25

Ser Asp Tyr Tyr Leu Ser Trp Val Arg Gln Pro Pro Gly Lys Ala Leu
30                  35                  40                  45

Glu Trp Val Gly Leu Ile Arg Asn Lys Ala Asn Gly Tyr Thr Arg Glu
                50                  55                  60

Tyr Ser Ala Ser Val Lys Gly Arg Phe Thr Ile Ser Arg Asp Asp Ser
                65                  70                  75

Gln Ser Ile Leu Tyr Leu Gln Met Asn Thr Leu Arg Gly Glu Asp Ser
                80                  85                  90

Ala Thr Tyr Tyr Cys Ala Arg Glu Asn Tyr Arg Tyr Asp Val Glu Leu
    95                  100                 105

Ala Tyr Trp Gly Gln Gly Thr Leu Val Thr Val Ser Ala
110             115                 120
```

(2) INFORMATION FOR SEQ ID NO:30:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...34
        (D) OTHER INFORMATION: chVL backward primer (xi) SEQUENCE DESCRIPTION: SEQ ID NO:30:

ACAAAGCTTC CACCATGAGT GTGCTCACTC AGGT                                 34

(2) INFORMATION FOR SEQ ID NO:31:

(i) SEQUENCE CHARACTERISTICS:
        (A) LENGTH: 37 base pairs
        (B) TYPE: nucleic acid (C) STRANDEDNESS: single
        (D) TOPOLOGY: linear (ix) FEATURE:
        (A) NAME/KEY: Other
        (B) LOCATION: 1...37
        (D) OTHER INFORMATION: chVH backward primer (xi) SEQUENCE DESCRIPTION: SEQ ID NO:31:

GATAAGCTTC CACCATGAAG TTGTGGTTAA ACTGGGT                                   37

(2) INFORMATION FOR SEQ ID NO:32:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...37
        (D) OTHER INFORMATION: chVL forward primer (xi) SEQUENCE DESCRIPTION: SEQ ID NO:32:

CTTGGATCCA CTCACGTTTG AGTTCCAGCT TGGTGCC                                   37

(2) INFORMATION FOR SEQ ID NO:33:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...37
        (D) OTHER INFORMATION: chVH forward primer (xi) SEQUENCE DESCRIPTION: SEQ ID NO:33:

GTCGGATCCA CTCACCTGCA GAGACAGTGA CCAGAGT                                   37

(2) INFORMATION FOR SEQ ID NO:34:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...137
        (D) OTHER INFORMATION: HF1 sequence (xi) SEQUENCE DESCRIPTION: SEQ ID NO:34:

TAAGCTTCCA CCATGGAGTT TGGGCTGAGC TGGGTTTTCC TTGTTGCTAT TTTAAAGGGT          60

GTCCAGTGTG AAGTGCAGCT GTTGGAGTCT GGGGGAGGCT TGGTCCAGCC TGGGGGTTCT         120

CTGAGACTCT CATGTGC                                                       137

(2) INFORMATION FOR SEQ ID NO:35:

(i) SEQUENCE CHARACTERISTICS:
        (A) LENGTH: 143 base pairs
        (B) TYPE: nucleic acid
        (C) STRANDEDNESS: single
        (D) TOPOLOGY: linear (ix) FEATURE:

```
        (A) NAME/KEY: Other
        (B) LOCATION: 1...143
        (D) OTHER INFORMATION: HF2 sequence (xi) SEQUENCE DESCRIPTION: SEQ ID NO:35:

GCACTGTACT CTCTTGTGTA ACCATTGGCT TTGTTTCTAA TGAGACCCAC CAACTCTAGC    60

CCTTTCCCTT GAGCTTGGCG GACCCAGCTC AGGTAGTAAT CACTGAAGGT GAATCCAGAG   120

GCAGCACATG AGAGTCTCAG AGA                                          143

(2) INFORMATION FOR SEQ ID NO:36:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...113
        (D) OTHER INFORMATION: HF3 sequence (xi) SEQUENCE DESCRIPTION: SEQ ID NO:36:

TACACAAGAG AGTACAGTGC ATCTGTGAAG GGCAGACTTA CCATCTCAAG AGAAGATTCA    60

AAGAACACGC TGTATCTGCA AATGAGCAGC CTGAAAACCG AAGACTTGGC CGT          113

(2) INFORMATION FOR SEQ ID NO:37:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...117
        (D) OTHER INFORMATION: HF4 sequence (xi) SEQUENCE DESCRIPTION: SEQ ID NO:37:

TCGGATCCAC TCACCTGAGG AGACGGTGAC CAGGGTTCCC TGGCCCCAGT AAGCAAGCTC    60

TACGTCGTAG CGATAGTTCT CTCTAGCACA GTAATACACG GCCAAGTCTT CGGTTTT     117

(2) INFORMATION FOR SEQ ID NO:38:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...37
        (D) OTHER INFORMATION: RVH5' primer (xi) SEQUENCE DESCRIPTION: SEQ ID NO:38:

GATAAGCTTC CACCATGGAG TTTGGGCTGA GCTGGGT                             37

(2) INFORMATION FOR SEQ ID NO:39:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
```

(A) NAME/KEY: Other
(B) LOCATION: 1...31
(D) OTHER INFORMATION: RVH3' primer (xi) SEQUENCE DESCRIPTION: SEQ ID NO:39:

GTCGGATCCA CTCACCTGAG GAGACGGTGA C                                31

(2) INFORMATION FOR SEQ ID NO:40:

(i) SEQUENCE CHARACTERISTICS:
    (A) LENGTH: 424 base pairs
    (B) TYPE: nucleic acid
    (C) STRANDEDNESS: double
    (D) TOPOLOGY: linear (ix) FEATURE:
    (A) NAME/KEY: Coding Sequence
    (B) LOCATION: 1...423
    (D) OTHER INFORMATION:
    (A) NAME/KEY: mat_peptide
    (B) LOCATION: 61...423
    (D) OTHER INFORMATION:
    (A) NAME/KEY: Signal Sequence
    (B) LOCATION: 1...60
    (D) OTHER INFORMATION:

(xi) SEQUENCE DESCRIPTION: SEQ ID NO:40:

```
ATG GAG TTT GGG CTG AGC TGG GTT TTC CTT GTT GCT ATT TTA AAG GGT        48
Met Glu Phe Gly Leu Ser Trp Val Phe Leu Val Ala Ile Leu Lys Gly
            -15                 -10                  -5

GTC CAG TGT GAA GTG CAG CTG TTG GAG TCT GGG GGA GGC TTG GTC CAG        96
Val Gln Cys Glu Val Gln Leu Leu Glu Ser Gly Gly Gly Leu Val Gln
              1               5                  10

CCT GGG GGT TCT CTG AGA CTC TCA TGT GCT GCC TCT GGA TTC ACC TTC       144
Pro Gly Gly Ser Leu Arg Leu Ser Cys Ala Ala Ser Gly Phe Thr Phe
         15                  20                  25

AGT GAT TAC TAC CTG AGC TGG GTC CGC CAA GCT CAA GGG AAA GGG CTA       192
Ser Asp Tyr Tyr Leu Ser Trp Val Arg Gln Ala Gln Gly Lys Gly Leu
30                  35                  40                  45

GAG TTG GTG GGT CTC ATT AGA AAC AAA GCC AAT GGT TAC ACA AGA GAG       240
Glu Leu Val Gly Leu Ile Arg Asn Lys Ala Asn Gly Tyr Thr Arg Glu
                 50                  55                  60

TAC AGT GCA TCT GTG AAG GGC AGA CTT ACC ATC TCA AGA GAA GAT TCA       288
Tyr Ser Ala Ser Val Lys Gly Arg Leu Thr Ile Ser Arg Glu Asp Ser
                 65                  70                  75

AAG AAC ACG CTG TAT CTG CAA ATG AGC AGC CTG AAA ACC GAA GAC TTG       336
Lys Asn Thr Leu Tyr Leu Gln Met Ser Ser Leu Lys Thr Glu Asp Leu
         80                  85                  90

GCC GTG TAT TAC TGT GCT AGA GAG AAC TAT CGC TAC GAC GTA GAG CTT       384
Ala Val Tyr Tyr Cys Ala Arg Glu Asn Tyr Arg Tyr Asp Val Glu Leu
         95                 100                 105

GCT TAC TGG GGC CAG GGA ACC CTG GTC ACC GTC TCC TCA G                 424
Ala Tyr Trp Gly Gln Gly Thr Leu Val Thr Val Ser Ser
110                 115                 120
```

(2) INFORMATION FOR SEQ ID NO:41:

(i) SEQUENCE CHARACTERISTICS:
    (A) LENGTH: 141 amino acids
    (B) TYPE: amino acid
    (C) STRANDEDNESS: single
    (D) TOPOLOGY: linear (ii) MOLECULE TYPE: protein (v) FRAGMENT TYPE: internal (ix) FEATURE:

(A) NAME/KEY: Signal Sequence
        (B) LOCATION: 1...19
        (D) OTHER INFORMATION:

(xi) SEQUENCE DESCRIPTION: SEQ ID NO:41:

Met Glu Phe Gly Leu Ser Trp Val Phe Leu Val Ala Ile Leu Lys Gly
            -15                 -10                  -5

Val Gln Cys Glu Val Gln Leu Leu Glu Ser Gly Gly Gly Leu Val Gln
             1               5                  10

Pro Gly Gly Ser Leu Arg Leu Ser Cys Ala Ala Ser Gly Phe Thr Phe
             15                  20                  25

Ser Asp Tyr Tyr Leu Ser Trp Val Arg Gln Ala Gln Gly Lys Gly Leu
30                   35                  40                  45

Glu Leu Val Gly Leu Ile Arg Asn Lys Ala Asn Gly Tyr Thr Arg Glu
                 50                  55                  60

Tyr Ser Ala Ser Val Lys Gly Arg Leu Thr Ile Ser Arg Glu Asp Ser
                 65                  70                  75

Lys Asn Thr Leu Tyr Leu Gln Met Ser Ser Leu Lys Thr Glu Asp Leu
                 80                  85                  90

Ala Val Tyr Tyr Cys Ala Arg Glu Asn Tyr Arg Tyr Asp Val Glu Leu
                 95                  100                 105

Ala Tyr Trp Gly Gln Gly Thr Leu Val Thr Val Ser Ser
110                 115                 120

(2) INFORMATION FOR SEQ ID NO:42:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...34
        (D) OTHER INFORMATION: LTW1 sequence (xi) SEQUENCE DESCRIPTION: SEQ ID NO:42:

GGCTAGAGTG GGTGGGTCTC ATTAGAAACA AAGC                                     34

(2) INFORMATION FOR SEQ ID NO:43:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...36
        (D) OTHER INFORMATION: LTW2 sequence (xi) SEQUENCE DESCRIPTION: SEQ ID NO:43:

GAGACCCACC CACTCTAGCC CTTTCCCTTG AGCTTG                                   36

(2) INFORMATION FOR SEQ ID NO:44:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ix) FEATURE:
        (A) NAME/KEY: Coding Sequence (B) LOCATION: 1...423
        (D) OTHER INFORMATION:
        (A) NAME/KEY: mat_peptide
        (B) LOCATION: 61...423
        (D) OTHER INFORMATION:
        (A) NAME/KEY: Signal Sequence
        (B) LOCATION: 1...60
        (D) OTHER INFORMATION:

(xi) SEQUENCE DESCRIPTION: SEQ ID NO:44:

```
ATG GAG TTT GGG CTG AGC TGG GTT TTC CTT GTT GCT ATT TTA AAG GGT         48
Met Glu Phe Gly Leu Ser Trp Val Phe Leu Val Ala Ile Leu Lys Gly
            -15              -10              -5

GTC CAG TGT GAA GTG CAG CTG TTG GAG TCT GGG GGA GGC TTG GTC CAG         96
Val Gln Cys Glu Val Gln Leu Leu Glu Ser Gly Gly Gly Leu Val Gln
            1                5                10

CCT GGG GGT TCT CTG AGA CTC TCA TGT GCT GCC TCT GGA TTC ACC TTC        144
Pro Gly Gly Ser Leu Arg Leu Ser Cys Ala Ala Ser Gly Phe Thr Phe
        15               20               25

AGT GAT TAC TAC CTG AGC TGG GTC CGC CAA GCT CAA GGG AAA GGG CTA        192
Ser Asp Tyr Tyr Leu Ser Trp Val Arg Gln Ala Gln Gly Lys Gly Leu
30              35               40               45

GAG TGG GTG GGT CTC ATT AGA AAC AAA GCC AAT GGT TAC ACA AGA GAG        240
Glu Trp Val Gly Leu Ile Arg Asn Lys Ala Asn Gly Tyr Thr Arg Glu
                50               55               60

TAC AGT GCA TCT GTG AAG GGC AGA CTT ACC ATC TCA AGA GAA GAT TCA        288
Tyr Ser Ala Ser Val Lys Gly Arg Leu Thr Ile Ser Arg Glu Asp Ser
            65               70               75

AAG AAC ACG CTG TAT CTG CAA ATG AGC AGC CTG AAA ACC GAA GAC TTG        336
Lys Asn Thr Leu Tyr Leu Gln Met Ser Ser Leu Lys Thr Glu Asp Leu
        80               85               90

GCC GTG TAT TAC TGT GCT AGA GAG AAC TAT CGC TAC GAC GTA GAG CTT        384
Ala Val Tyr Tyr Cys Ala Arg Glu Asn Tyr Arg Tyr Asp Val Glu Leu
95              100              105

GCT TAC TGG GGC CAG GGA ACC CTG GTC ACC GTC TCC TCA G                  424
Ala Tyr Trp Gly Gln Gly Thr Leu Val Thr Val Ser Ser
110              115              120
```

(2) INFORMATION FOR SEQ ID NO:45:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:45:

```
Met Glu Phe Gly Leu Ser Trp Val Phe Leu Val Ala Ile Leu Lys Gly
            -15              -10              -5

Val Gln Cys Glu Val Gln Leu Leu Glu Ser Gly Gly Gly Leu Val Gln
            1                5                10

Pro Gly Gly Ser Leu Arg Leu Ser Cys Ala Ala Ser Gly Phe Thr Phe
        15               20               25

Ser Asp Tyr Tyr Leu Ser Trp Val Arg Gln Ala Gln Gly Lys Gly Leu
30              35               40               45

Glu Trp Val Gly Leu Ile Arg Asn Lys Ala Asn Gly Tyr Thr Arg Glu
```

```
                    50                  55                  60
Tyr Ser Ala Ser Val Lys Gly Arg Leu Thr Ile Ser Arg Glu Asp Ser
                65                  70                  75

Lys Asn Thr Leu Tyr Leu Gln Met Ser Ser Leu Lys Thr Glu Asp Leu
            80                  85                  90

Ala Val Tyr Tyr Cys Ala Arg Glu Asn Tyr Arg Tyr Asp Val Glu Leu
        95                  100                 105

Ala Tyr Trp Gly Gln Gly Thr Leu Val Thr Val Ser Ser
110                 115                 120
```

(2) INFORMATION FOR SEQ ID NO:46:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ix) FEATURE:
    (A) NAME/KEY: Other
    (B) LOCATION: 1...32
    (D) OTHER INFORMATION: QTP1 sequence (xi) SEQUENCE DESCRIPTION: SEQ ID NO:46:

TGGGTCCGCC AAGCTCCAGG GAAAGGGCTA GA        32

(2) INFORMATION FOR SEQ ID NO:47:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ix) FEATURE:
    (A) NAME/KEY: Other
    (B) LOCATION: 1...32
    (D) OTHER INFORMATION: QTP2 sequence (xi) SEQUENCE DESCRIPTION: SEQ ID NO:47:

TCTAGCCCTT TCCCTGGAGC TTGGCGGACC CA       32

(2) INFORMATION FOR SEQ ID NO:48:

(i) SEQUENCE CHARACTERISTICS:
    (A) LENGTH: 424 base pairs
    (B) TYPE: nucleic acid
    (C) STRANDEDNESS: double
    (D) TOPOLOGY: linear (ix) FEATURE:
    (A) NAME/KEY: Coding Sequence
    (B) LOCATION: 1...423
    (D) OTHER INFORMATION:
    (A) NAME/KEY: mat_peptide
    (B) LOCATION: 61...423
    (D) OTHER INFORMATION:
    (A) NAME/KEY: Signal Sequence
    (B) LOCATION: 1...60
    (D) OTHER INFORMATION:

(xi) SEQUENCE DESCRIPTION: SEQ ID NO:48:

```
ATG GAG TTT GGG CTG AGC TGG GTT TTC CTT GTT GCT ATT TTA AAG GGT    48
Met Glu Phe Gly Leu Ser Trp Val Phe Leu Val Ala Ile Leu Lys Gly
            -15                 -10                 -5

GTC CAG TGT GAA GTG CAG CTG TTG GAG TCT GGG GGA GGC TTG GTC CAG    96
Val Gln Cys Glu Val Gln Leu Leu Glu Ser Gly Gly Gly Leu Val Gln
                1               5                   10
```

```
CCT GGG GGT TCT CTG AGA CTC TCA TGT GCT GCC TCT GGA TTC ACC TTC        144
Pro Gly Gly Ser Leu Arg Leu Ser Cys Ala Ala Ser Gly Phe Thr Phe
    15                  20                  25

AGT GAT TAC TAC CTG AGC TGG GTC CGC CAA GCT CCA GGG AAA GGG CTA        192
Ser Asp Tyr Tyr Leu Ser Trp Val Arg Gln Ala Pro Gly Lys Gly Leu
30                  35                  40                  45

GAG TTG GTG GGT CTC ATT AGA AAC AAA GCC AAT GGT TAC ACA AGA GAG        240
Glu Leu Val Gly Leu Ile Arg Asn Lys Ala Asn Gly Tyr Thr Arg Glu
                50                  55                  60

TAC AGT GCA TCT GTG AAG GGC AGA CTT ACC ATC TCA AGA GAA GAT TCA        288
Tyr Ser Ala Ser Val Lys Gly Arg Leu Thr Ile Ser Arg Glu Asp Ser
                65                  70                  75

AAG AAC ACG CTG TAT CTG CAA ATG AGC AGC CTG AAA ACC GAA GAC TTG        336
Lys Asn Thr Leu Tyr Leu Gln Met Ser Ser Leu Lys Thr Glu Asp Leu
            80                  85                  90

GCC GTG TAT TAC TGT GCT AGA GAG AAC TAT CGC TAC GAC GTA GAG CTT        384
Ala Val Tyr Tyr Cys Ala Arg Glu Asn Tyr Arg Tyr Asp Val Glu Leu
        95                  100                 105

GCT TAC TGG GGC CAG GGA ACC CTG GTC ACC GTC TCC TCA G                  424
Ala Tyr Trp Gly Gln Gly Thr Leu Val Thr Val Ser Ser
110                 115                 120
```

(2) INFORMATION FOR SEQ ID NO:49:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:49:

```
Met Glu Phe Gly Leu Ser Trp Val Phe Leu Val Ala Ile Leu Lys Gly
                -15                 -10                 -5

Val Gln Cys Glu Val Gln Leu Leu Glu Ser Gly Gly Gly Leu Val Gln
            1                   5                   10

Pro Gly Gly Ser Leu Arg Leu Ser Cys Ala Ala Ser Gly Phe Thr Phe
    15                  20                  25

Ser Asp Tyr Tyr Leu Ser Trp Val Arg Gln Ala Pro Gly Lys Gly Leu
30                  35                  40                  45

Glu Leu Val Gly Leu Ile Arg Asn Lys Ala Asn Gly Tyr Thr Arg Glu
                50                  55                  60

Tyr Ser Ala Ser Val Lys Gly Arg Leu Thr Ile Ser Arg Glu Asp Ser
                65                  70                  75

Lys Asn Thr Leu Tyr Leu Gln Met Ser Ser Leu Lys Thr Glu Asp Leu
            80                  85                  90

Ala Val Tyr Tyr Cys Ala Arg Glu Asn Tyr Arg Tyr Asp Val Glu Leu
        95                  100                 105

Ala Tyr Trp Gly Gln Gly Thr Leu Val Thr Val Ser Ser
110                 115                 120
```

(2) INFORMATION FOR SEQ ID NO:50:

(i) SEQUENCE CHARACTERISTICS:
        (A) LENGTH: 424 base pairs

```
            (B) TYPE: nucleic acid
            (C) STRANDEDNESS: double
            (D) TOPOLOGY: linear (ix) FEATURE:
            (A) NAME/KEY: Coding Sequence
            (B) LOCATION: 1...423
            (D) OTHER INFORMATION:
            (A) NAME/KEY: mat_peptide
            (B) LOCATION: 61...423
            (D) OTHER INFORMATION:
            (A) NAME/KEY: Signal Sequence
            (B) LOCATION: 1...60
            (D) OTHER INFORMATION:

(xi) SEQUENCE DESCRIPTION: SEQ ID NO:50:

ATG GAG TTT GGG CTG AGC TGG GTT TTC CTT GTT GCT ATT TTA AAG GGT         48
Met Glu Phe Gly Leu Ser Trp Val Phe Leu Val Ala Ile Leu Lys Gly
            -15                 -10                  -5

GTC CAG TGT GAA GTG CAG CTG TTG GAG TCT GGG GGA GGC TTG GTC CAG         96
Val Gln Cys Glu Val Gln Leu Leu Glu Ser Gly Gly Gly Leu Val Gln
             1                   5                  10

CCT GGG GGT TCT CTG AGA CTC TCA TGT GCT GCC TCT GGA TTC ACC TTC        144
Pro Gly Gly Ser Leu Arg Leu Ser Cys Ala Ala Ser Gly Phe Thr Phe
 15                  20                  25

AGT GAT TAC TAC CTG AGC TGG GTC CGC CAA GCT CCA GGG AAA GGG CTA        192
Ser Asp Tyr Tyr Leu Ser Trp Val Arg Gln Ala Pro Gly Lys Gly Leu
 30                  35                  40                  45

GAG TGG GTG GGT CTC ATT AGA AAC AAA GCC AAT GGT TAC ACA AGA GAG        240
Glu Trp Val Gly Leu Ile Arg Asn Lys Ala Asn Gly Tyr Thr Arg Glu
                 50                  55                  60

TAC AGT GCA TCT GTG AAG GGC AGA CTT ACC ATC TCA AGA GAA GAT TCA        288
Tyr Ser Ala Ser Val Lys Gly Arg Leu Thr Ile Ser Arg Glu Asp Ser
                 65                  70                  75

AAG AAC ACG CTG TAT CTG CAA ATG AGC AGC CTG AAA ACC GAA GAC TTG        336
Lys Asn Thr Leu Tyr Leu Gln Met Ser Ser Leu Lys Thr Glu Asp Leu
                 80                  85                  90

GCC GTG TAT TAC TGT GCT AGA GAG AAC TAT CGC TAC GAC GTA GAG CTT        384
Ala Val Tyr Tyr Cys Ala Arg Glu Asn Tyr Arg Tyr Asp Val Glu Leu
 95                 100                 105

GCT TAC TGG GGC CAG GGA ACC CTG GTC ACC GTC TCC TCA G                  424
Ala Tyr Trp Gly Gln Gly Thr Leu Val Thr Val Ser Ser
110                 115                 120

(2) INFORMATION FOR SEQ ID NO:51:

(i) SEQUENCE CHARACTERISTICS:
            (A) LENGTH: 141 amino acids
            (B) TYPE: amino acid
            (C) STRANDEDNESS: single
            (D) TOPOLOGY: linear (ii) MOLECULE TYPE: protein (v) FRAGMENT TYPE: internal (ix) FEATURE:
            (A) NAME/KEY: Signal Sequence
            (B) LOCATION: 1...19
            (D) OTHER INFORMATION:

(xi) SEQUENCE DESCRIPTION: SEQ ID NO:51:

Met Glu Phe Gly Leu Ser Trp Val Phe Leu Val Ala Ile Leu Lys Gly
            -15                 -10                  -5

Val Gln Cys Glu Val Gln Leu Leu Glu Ser Gly Gly Gly Leu Val Gln
             1                   5                  10

Pro Gly Gly Ser Leu Arg Leu Ser Cys Ala Ala Ser Gly Phe Thr Phe
```

```
                 15                  20                  25

Ser Asp Tyr Tyr Leu Ser Trp Val Arg Gln Ala Pro Gly Lys Gly Leu
 30                  35                  40                  45

Glu Trp Val Gly Leu Ile Arg Asn Lys Ala Asn Gly Tyr Thr Arg Glu
                 50                  55                  60

Tyr Ser Ala Ser Val Lys Gly Arg Leu Thr Ile Ser Arg Glu Asp Ser
             65                  70                  75

Lys Asn Thr Leu Tyr Leu Gln Met Ser Ser Leu Lys Thr Glu Asp Leu
         80                  85                  90

Ala Val Tyr Tyr Cys Ala Arg Glu Asn Tyr Arg Tyr Asp Val Glu Leu
     95                 100                 105

Ala Tyr Trp Gly Gln Gly Thr Leu Val Thr Val Ser Ser
110                 115                 120
```

(2) INFORMATION FOR SEQ ID NO:52:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...26
        (D) OTHER INFORMATION: ATP1 sequence (xi) SEQUENCE DESCRIPTION: SEQ ID NO:52:

```
TGGGTCCGCC AACCTCCAGG GAAAGG                                        26
```

(2) INFORMATION FOR SEQ ID NO:53:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...26
        (D) OTHER INFORMATION: ATP2 sequence (xi) SEQUENCE DESCRIPTION: SEQ ID NO:53:

```
CCTTTCCCTG GAGGTTGGCG GACCCA                                        26
```

(2) INFORMATION FOR SEQ ID NO:54:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 1...423
        (D) OTHER INFORMATION:
        (A) NAME/KEY: mat_peptide
        (B) LOCATION: 61...423
        (D) OTHER INFORMATION:
        (A) NAME/KEY: Signal Sequence
        (B) LOCATION: 1...60
        (D) OTHER INFORMATION:

(xi) SEQUENCE DESCRIPTION: SEQ ID NO:54:

```
ATG GAG TTT GGG CTG AGC TGG GTT TTC CTT GTT GCT ATT TTA AAG GGT    48
Met Glu Phe Gly Leu Ser Trp Val Phe Leu Val Ala Ile Leu Lys Gly
```

```
                  -15               -10                -5
GTC CAG TGT GAA GTG CAG CTG TTG GAG TCT GGG GGA GGC TTG GTC CAG      96
Val Gln Cys Glu Val Gln Leu Leu Glu Ser Gly Gly Gly Leu Val Gln
              1                   5                  10

CCT GGG GGT TCT CTG AGA CTC TCA TGT GCT GCC TCT GGA TTC ACC TTC     144
Pro Gly Gly Ser Leu Arg Leu Ser Cys Ala Ala Ser Gly Phe Thr Phe
 15                  20                  25

AGT GAT TAC TAC CTG AGC TGG GTC CGC CAA CCT CCA GGG AAA GGG CTA     192
Ser Asp Tyr Tyr Leu Ser Trp Val Arg Gln Pro Pro Gly Lys Gly Leu
 30              35                  40                  45

GAG TGG GTG GGT CTC ATT AGA AAC AAA GCC AAT GGT TAC ACA AGA GAG     240
Glu Trp Val Gly Leu Ile Arg Asn Lys Ala Asn Gly Tyr Thr Arg Glu
                 50                  55                  60

TAC AGT GCA TCT GTG AAG GGC AGA CTT ACC ATC TCA AGA GAA GAT TCA     288
Tyr Ser Ala Ser Val Lys Gly Arg Leu Thr Ile Ser Arg Glu Asp Ser
             65                  70                  75

AAG AAC ACG CTG TAT CTG CAA ATG AGC AGC CTG AAA ACC GAA GAC TTG     336
Lys Asn Thr Leu Tyr Leu Gln Met Ser Ser Leu Lys Thr Glu Asp Leu
         80                  85                  90

GCC GTG TAT TAC TGT GCT AGA GAG AAC TAT CGC TAC GAC GTA GAG CTT     384
Ala Val Tyr Tyr Cys Ala Arg Glu Asn Tyr Arg Tyr Asp Val Glu Leu
     95                 100                 105

GCT TAC TGG GGC CAG GGA ACC CTG GTC ACC GTC TCC TCA G               424
Ala Tyr Trp Gly Gln Gly Thr Leu Val Thr Val Ser Ser
110                 115                 120
```

(2) INFORMATION FOR SEQ ID NO:55:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:55:

```
Met Glu Phe Gly Leu Ser Trp Val Phe Leu Val Ala Ile Leu Lys Gly
             -15                 -10                  -5

Val Gln Cys Glu Val Gln Leu Leu Glu Ser Gly Gly Gly Leu Val Gln
              1                   5                  10

Pro Gly Gly Ser Leu Arg Leu Ser Cys Ala Ala Ser Gly Phe Thr Phe
 15                  20                  25

Ser Asp Tyr Tyr Leu Ser Trp Val Arg Gln Pro Pro Gly Lys Gly Leu
 30              35                  40                  45

Glu Trp Val Gly Leu Ile Arg Asn Lys Ala Asn Gly Tyr Thr Arg Glu
                 50                  55                  60

Tyr Ser Ala Ser Val Lys Gly Arg Leu Thr Ile Ser Arg Glu Asp Ser
             65                  70                  75

Lys Asn Thr Leu Tyr Leu Gln Met Ser Ser Leu Lys Thr Glu Asp Leu
         80                  85                  90

Ala Val Tyr Tyr Cys Ala Arg Glu Asn Tyr Arg Tyr Asp Val Glu Leu
     95                 100                 105

Ala Tyr Trp Gly Gln Gly Thr Leu Val Thr Val Ser Ser
110                 115                 120
```

(2) INFORMATION FOR SEQ ID NO:56:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...29
        (D) OTHER INFORMATION: GTA1 sequence (xi) SEQUENCE DESCRIPTION: SEQ ID NO:56:

CAAGCTCCAG GGAAAGCGCT AGAGTGGGT                                     29

(2) INFORMATION FOR SEQ ID NO:57:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...29
        (D) OTHER INFORMATION: GTA2 sequence (xi) SEQUENCE DESCRIPTION: SEQ ID NO:57:

ACCCACTCTA GCGCTTTCCC TGGAGCTTG                                     29

(2) INFORMATION FOR SEQ ID NO:58:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 1...423
        (D) OTHER INFORMATION:
        (A) NAME/KEY: mat_peptide
        (B) LOCATION: 61...423
        (D) OTHER INFORMATION:
        (A) NAME/KEY: Signal Sequence
        (B) LOCATION: 1...60
        (D) OTHER INFORMATION:

(xi) SEQUENCE DESCRIPTION: SEQ ID NO:58:

```
ATG GAG TTT GGG CTG AGC TGG GTT TTC CTT GTT GCT ATT TTA AAG GGT      48
Met Glu Phe Gly Leu Ser Trp Val Phe Leu Val Ala Ile Leu Lys Gly
            -15                 -10                 -5

GTC CAG TGT GAA GTG CAG CTG TTG GAG TCT GGG GGA GGC TTG GTC CAG      96
Val Gln Cys Glu Val Gln Leu Leu Glu Ser Gly Gly Gly Leu Val Gln
             1               5                  10

CCT GGG GGT TCT CTG AGA CTC TCA TGT GCT GCC TCT GGA TTC ACC TTC     144
Pro Gly Gly Ser Leu Arg Leu Ser Cys Ala Ala Ser Gly Phe Thr Phe
 15                  20                  25

AGT GAT TAC TAC CTG AGC TGG GTC CGC CAA GCT CCA GGG AAA GCG CTA     192
Ser Asp Tyr Tyr Leu Ser Trp Val Arg Gln Ala Pro Gly Lys Ala Leu
 30                  35                  40                  45

GAG TGG GTG GGT CTC ATT AGA AAC AAA GCC AAT GGT TAC ACA AGA GAG     240
Glu Trp Val Gly Leu Ile Arg Asn Lys Ala Asn Gly Tyr Thr Arg Glu
                 50                  55                  60

TAC AGT GCA TCT GTG AAG GGC AGA CTT ACC ATC TCA AGA GAA GAT TCA     288
```

-continued

```
Tyr Ser Ala Ser Val Lys Gly Arg Leu Thr Ile Ser Arg Glu Asp Ser
            65                  70                  75

AAG AAC ACG CTG TAT CTG CAA ATG AGC AGC CTG AAA ACC GAA GAC TTG      336
Lys Asn Thr Leu Tyr Leu Gln Met Ser Ser Leu Lys Thr Glu Asp Leu
            80                  85                  90

GCC GTG TAT TAC TGT GCT AGA GAG AAC TAT CGC TAC GAC GTA GAG CTT      384
Ala Val Tyr Tyr Cys Ala Arg Glu Asn Tyr Arg Tyr Asp Val Glu Leu
            95                 100                 105

GCT TAC TGG GGC CAG GGA ACC CTG GTC ACC GTC TCC TCA G                424
Ala Tyr Trp Gly Gln Gly Thr Leu Val Thr Val Ser Ser
110                 115                 120
```

(2) INFORMATION FOR SEQ ID NO:59:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:59:

```
Met Glu Phe Gly Leu Ser Trp Val Phe Leu Val Ala Ile Leu Lys Gly
            -15                 -10                 -5

Val Gln Cys Glu Val Gln Leu Leu Glu Ser Gly Gly Gly Leu Val Gln
             1                   5                  10

Pro Gly Gly Ser Leu Arg Leu Ser Cys Ala Ala Ser Gly Phe Thr Phe
            15                  20                  25

Ser Asp Tyr Tyr Leu Ser Trp Val Arg Gln Ala Pro Gly Lys Ala Leu
30                  35                  40                  45

Glu Trp Val Gly Leu Ile Arg Asn Lys Ala Asn Gly Tyr Thr Arg Glu
            50                  55                  60

Tyr Ser Ala Ser Val Lys Gly Arg Leu Thr Ile Ser Arg Glu Asp Ser
            65                  70                  75

Lys Asn Thr Leu Tyr Leu Gln Met Ser Ser Leu Lys Thr Glu Asp Leu
            80                  85                  90

Ala Val Tyr Tyr Cys Ala Arg Glu Asn Tyr Arg Tyr Asp Val Glu Leu
            95                 100                 105

Ala Tyr Trp Gly Gln Gly Thr Leu Val Thr Val Ser Ser
110                 115                 120
```

(2) INFORMATION FOR SEQ ID NO:60:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...23
        (D) OTHER INFORMATION: LTF1 sequence (xi) SEQUENCE DESCRIPTION: SEQ ID NO:60:

GTGAAGGGCA GATTTACCAT CTC                                                     23

(2) INFORMATION FOR SEQ ID NO:61:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...23
        (D) OTHER INFORMATION: LTF2 sequence (xi) SEQUENCE DESCRIPTION: SEQ ID NO:61:

```
GAGATGGTAA ATCTGCCCTT CAC                                              23
```

(2) INFORMATION FOR SEQ ID NO:62:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 1...423
        (D) OTHER INFORMATION:
        (A) NAME/KEY: mat_peptide
        (B) LOCATION: 61...423
        (D) OTHER INFORMATION:
        (A) NAME/KEY: Signal Sequence
        (B) LOCATION: 1...60
        (D) OTHER INFORMATION:

(xi) SEQUENCE DESCRIPTION: SEQ ID NO:62:

```
ATG GAG TTT GGG CTG AGC TGG GTT TTC CTT GTT GCT ATT TTA AAG GGT         48
Met Glu Phe Gly Leu Ser Trp Val Phe Leu Val Ala Ile Leu Lys Gly
            -15             -10                 -5

GTC CAG TGT GAA GTG CAG CTG TTG GAG TCT GGG GGA GGC TTG GTC CAG         96
Val Gln Cys Glu Val Gln Leu Leu Glu Ser Gly Gly Gly Leu Val Gln
             1               5                  10

CCT GGG GGT TCT CTG AGA CTC TCA TGT GCT GCC TCT GGA TTC ACC TTC        144
Pro Gly Gly Ser Leu Arg Leu Ser Cys Ala Ala Ser Gly Phe Thr Phe
        15              20                  25

AGT GAT TAC TAC CTG AGC TGG GTC CGC CAA GCT CCA GGG AAA GGG CTA        192
Ser Asp Tyr Tyr Leu Ser Trp Val Arg Gln Ala Pro Gly Lys Gly Leu
30              35                  40                  45

GAG TGG GTG GGT CTC ATT AGA AAC AAA GCC AAT GGT TAC ACA AGA GAG        240
Glu Trp Val Gly Leu Ile Arg Asn Lys Ala Asn Gly Tyr Thr Arg Glu
                50                  55                  60

TAC AGT GCA TCT GTG AAG GGC AGA TTT ACC ATC TCA AGA GAA GAT TCA        288
Tyr Ser Ala Ser Val Lys Gly Arg Phe Thr Ile Ser Arg Glu Asp Ser
                65                  70                  75

AAG AAC ACG CTG TAT CTG CAA ATG AGC AGC CTG AAA ACC GAA GAC TTG        336
Lys Asn Thr Leu Tyr Leu Gln Met Ser Ser Leu Lys Thr Glu Asp Leu
                80                  85                  90

GCC GTG TAT TAC TGT GCT AGA GAG AAC TAT CGC TAC GAC GTA GAG CTT        384
Ala Val Tyr Tyr Cys Ala Arg Glu Asn Tyr Arg Tyr Asp Val Glu Leu
        95                  100                 105

GCT TAC TGG GGC CAG GGA ACC CTG GTC ACC GTC TCC TCA G                  424
Ala Tyr Trp Gly Gln Gly Thr Leu Val Thr Val Ser Ser
110             115                 120
```

(2) INFORMATION FOR SEQ ID NO:63:

(i) SEQUENCE CHARACTERISTICS:

(A) LENGTH: 141 amino acids
         (B) TYPE: amino acid
         (C) STRANDEDNESS: single
         (D) TOPOLOGY: linear (ii) MOLECULE TYPE: protein (v) FRAGMENT TYPE: internal (ix) FEATURE:
         (A) NAME/KEY: Signal Sequence
         (B) LOCATION: 1...19
         (D) OTHER INFORMATION:

(xi) SEQUENCE DESCRIPTION: SEQ ID NO:63:

```
Met Glu Phe Gly Leu Ser Trp Val Phe Leu Val Ala Ile Leu Lys Gly
            -15                 -10                 -5

Val Gln Cys Glu Val Gln Leu Leu Glu Ser Gly Gly Gly Leu Val Gln
            1               5                   10

Pro Gly Gly Ser Leu Arg Leu Ser Cys Ala Ala Ser Gly Phe Thr Phe
        15                  20                  25

Ser Asp Tyr Tyr Leu Ser Trp Val Arg Gln Ala Pro Gly Lys Gly Leu
30              35                  40                  45

Glu Trp Val Gly Leu Ile Arg Asn Lys Ala Asn Gly Tyr Thr Arg Glu
                50                  55                  60

Tyr Ser Ala Ser Val Lys Gly Arg Phe Thr Ile Ser Arg Glu Asp Ser
            65                  70                  75

Lys Asn Thr Leu Tyr Leu Gln Met Ser Ser Leu Lys Thr Glu Asp Leu
            80                  85                  90

Ala Val Tyr Tyr Cys Ala Arg Glu Asn Tyr Arg Tyr Asp Val Glu Leu
            95                  100                 105

Ala Tyr Trp Gly Gln Gly Thr Leu Val Thr Val Ser Ser
110                 115                 120
```

(2) INFORMATION FOR SEQ ID NO:64:

(i) SEQUENCE CHARACTERISTICS:
         (A) LENGTH: 424 base pairs
         (B) TYPE: nucleic acid
         (C) STRANDEDNESS: double
         (D) TOPOLOGY: linear (ix) FEATURE:
         (A) NAME/KEY: Coding Sequence
         (B) LOCATION: 1...423
         (D) OTHER INFORMATION:
         (A) NAME/KEY: mat_peptide
         (B) LOCATION: 61...423
         (D) OTHER INFORMATION:
         (A) NAME/KEY: Signal Sequence
         (B) LOCATION: 1...60
         (D) OTHER INFORMATION:

(xi) SEQUENCE DESCRIPTION: SEQ ID NO:64:

```
ATG GAG TTT GGG CTG AGC TGG GTT TTC CTT GTT GCT ATT TTA AAG GGT       48
Met Glu Phe Gly Leu Ser Trp Val Phe Leu Val Ala Ile Leu Lys Gly
            -15                 -10                 -5

GTC CAG TGT GAA GTG CAG CTG TTG GAG TCT GGG GGA GGC TTG GTC CAG       96
Val Gln Cys Glu Val Gln Leu Leu Glu Ser Gly Gly Gly Leu Val Gln
            1               5                   10

CCT GGG GGT TCT CTG AGA CTC TCA TGT GCT GCC TCT GGA TTC ACC TTC      144
Pro Gly Gly Ser Leu Arg Leu Ser Cys Ala Ala Ser Gly Phe Thr Phe
        15                  20                  25

AGT GAT TAC TAC CTG AGC TGG GTC CGC CAA GCT CAA GGG AAA GGG CTA      192
Ser Asp Tyr Tyr Leu Ser Trp Val Arg Gln Ala Gln Gly Lys Gly Leu
30              35                  40                  45
```

```
GAG TGG GTG GGT CTC ATT AGA AAC AAA GCC AAT GGT TAC ACA AGA GAG        240
Glu Trp Val Gly Leu Ile Arg Asn Lys Ala Asn Gly Tyr Thr Arg Glu
             50                  55                  60

TAC AGT GCA TCT GTG AAG GGC AGA TTT ACC ATC TCA AGA GAA GAT TCA        288
Tyr Ser Ala Ser Val Lys Gly Arg Phe Thr Ile Ser Arg Glu Asp Ser
        65                  70                  75

AAG AAC ACG CTG TAT CTG CAA ATG AGC AGC CTG AAA ACC GAA GAC TTG        336
Lys Asn Thr Leu Tyr Leu Gln Met Ser Ser Leu Lys Thr Glu Asp Leu
            80                  85                  90

GCC GTG TAT TAC TGT GCT AGA GAG AAC TAT CGC TAC GAC GTA GAG CTT        384
Ala Val Tyr Tyr Cys Ala Arg Glu Asn Tyr Arg Tyr Asp Val Glu Leu
        95                 100                 105

GCT TAC TGG GGC CAG GGA ACC CTG GTC ACC GTC TCC TCA G                  424
Ala Tyr Trp Gly Gln Gly Thr Leu Val Thr Val Ser Ser
110                 115                 120

(2) INFORMATION FOR SEQ ID NO:65:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:65:

Met Glu Phe Gly Leu Ser Trp Val Phe Leu Val Ala Ile Leu Lys Gly
            -15                 -10                 -5

Val Gln Cys Glu Val Gln Leu Leu Glu Ser Gly Gly Gly Leu Val Gln
             1                   5                  10

Pro Gly Gly Ser Leu Arg Leu Ser Cys Ala Ala Ser Gly Phe Thr Phe
        15                  20                  25

Ser Asp Tyr Tyr Leu Ser Trp Val Arg Gln Ala Gln Gly Lys Gly Leu
 30                  35                  40                  45

Glu Trp Val Gly Leu Ile Arg Asn Lys Ala Asn Gly Tyr Thr Arg Glu
             50                  55                  60

Tyr Ser Ala Ser Val Lys Gly Arg Phe Thr Ile Ser Arg Glu Asp Ser
        65                  70                  75

Lys Asn Thr Leu Tyr Leu Gln Met Ser Ser Leu Lys Thr Glu Asp Leu
            80                  85                  90

Ala Val Tyr Tyr Cys Ala Arg Glu Asn Tyr Arg Tyr Asp Val Glu Leu
        95                 100                 105

Ala Tyr Trp Gly Gln Gly Thr Leu Val Thr Val Ser Ser
110                 115                 120

(2) INFORMATION FOR SEQ ID NO:66:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...124
```

(D) OTHER INFORMATION: LF1 sequence (xi) SEQUENCE DESCRIPTION: SEQ ID NO:66:

TTGAAGCTTC CACCATGGGA TGGAGCTGTA TCATCCTCTT CTTGGTAGCA ACAGCTACAG    60

GTGTCCACTC CGACATCCAG ATGACCCAGA GCCCAAGCAG CCTGAGCGCC AGCGTAGGTG   120

ACAG                                                                124

(2) INFORMATION FOR SEQ ID NO:67:

(i) SEQUENCE CHARACTERISTICS:
        (A) LENGTH: 122 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...122
        (D) OTHER INFORMATION: LF2 sequence (xi) SEQUENCE DESCRIPTION: SEQ ID NO:67:

GCATTGTAGA TCAGCAGCTT TGGAGCCTTT CCTGGCTTCT GCTGGTACCA TGCTAAATAA    60

CTGTAAATAA TCTCGCTTGC TCGACAGGTG ATGGTCACTC TGTCACCTAC GCTGGCGCTC   120

AG                                                                  122

(2) INFORMATION FOR SEQ ID NO:68:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...121
        (D) OTHER INFORMATION: LF3 sequence (xi) SEQUENCE DESCRIPTION: SEQ ID NO:68:

AGCTGCTGAT CTACAATGCA AAAACCTTAG CAGATGGAGT GCCAAGCAGA TTCAGCGGTA    60

GCGGTAGCGG TACCGACTTC ACCTTCACCA TCAGCAGCCT CCAGCCAGAG GACATCGCTA   120

C                                                                   121

(2) INFORMATION FOR SEQ ID NO:69:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...106
        (D) OTHER INFORMATION: LF4 sequence (xi) SEQUENCE DESCRIPTION: SEQ ID NO:69:

GTAGGATCCA CTCACGTTTG ATTTCGACCT TGGTCCCTTG GCCGAACGTC CGAGGAAAAC    60

CAAAATGATG TTGGCAGTAG TAGGTAGCGA TGTCCTCTGG CTGGAG                  106

(2) INFORMATION FOR SEQ ID NO:70:

(i) SEQUENCE CHARACTERISTICS:
        (A) LENGTH: 20 base pairs
        (B) TYPE: nucleic acid (C) STRANDEDNESS: single
        (D) TOPOLOGY: linear (ix) FEATURE:
        (A) NAME/KEY: Other
        (B) LOCATION: 1...20
        (D) OTHER INFORMATION: RVL5' sequence (xi) SEQUENCE DESCRIPTION: SEQ ID NO:70:

TTGAAGCTTC CACCATGGGA                                              20

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...20
        (D) OTHER INFORMATION: RVL3' sequence (xi) SEQUENCE DESCRIPTION: SEQ ID NO:71:

GTAGGATCCA CTCACGTTTG                                              20

(2) INFORMATION FOR SEQ ID NO:72:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 1...378
        (D) OTHER INFORMATION:
        (A) NAME/KEY: mat_peptide
        (B) LOCATION: 61...378
        (D) OTHER INFORMATION:
        (A) NAME/KEY: Signal Sequence
        (B) LOCATION: 1...60
        (D) OTHER INFORMATION:

(xi) SEQUENCE DESCRIPTION: SEQ ID NO:72:

```
ATG GGA TGG AGC TGT ATC ATC CTC TTC TTG GTA GCA ACA GCT ACA GGT        48
Met Gly Trp Ser Cys Ile Ile Leu Phe Leu Val Ala Thr Ala Thr Gly
            -15                 -10                  -5

GTC CAC TCC GAC ATC CAG ATG ACC CAG AGC CCA AGC AGC CTG AGC GCC        96
Val His Ser Asp Ile Gln Met Thr Gln Ser Pro Ser Ser Leu Ser Ala
            1                   5                   10

AGC GTA GGT GAC AGA GTG ACC ATC ACC TGT CGA GCA AGC GAG ATT ATT       144
Ser Val Gly Asp Arg Val Thr Ile Thr Cys Arg Ala Ser Glu Ile Ile
        15                  20                  25

TAC AGT TAT TTA GCA TGG TAC CAG CAG AAG CCA GGA AAG GCT CCA AAG       192
Tyr Ser Tyr Leu Ala Trp Tyr Gln Gln Lys Pro Gly Lys Ala Pro Lys
30                  35                  40                  45

CTG CTG ATC TAC AAT GCA AAA ACC TTA GCA GAT GGA GTG CCA AGC AGA       240
Leu Leu Ile Tyr Asn Ala Lys Thr Leu Ala Asp Gly Val Pro Ser Arg
                50                  55                  60

TTC AGC GGT AGC GGT AGC GGT ACC GAC TTC ACC TTC ACC ATC AGC AGC       288
Phe Ser Gly Ser Gly Ser Gly Thr Asp Phe Thr Phe Thr Ile Ser Ser
                    65                  70                  75

CTC CAG CCA GAG GAC ATC GCT ACC TAC TAC TGC CAA CAT CAT TTT GGT       336
Leu Gln Pro Glu Asp Ile Ala Thr Tyr Tyr Cys Gln His His Phe Gly
            80                  85                  90
```

```
TTT CCT CGG ACG TTC GGC CAA GGG ACC AAG GTC GAA ATC AAA C          379
Phe Pro Arg Thr Phe Gly Gln Gly Thr Lys Val Glu Ile Lys
    95                  100                 105
```

(2) INFORMATION FOR SEQ ID NO:73:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:73:

```
Met Gly Trp Ser Cys Ile Ile Leu Phe Leu Val Ala Thr Ala Thr Gly
                -15                 -10                 -5

Val His Ser Asp Ile Gln Met Thr Gln Ser Pro Ser Ser Leu Ser Ala
     1                   5                   10

Ser Val Gly Asp Arg Val Thr Ile Thr Cys Arg Ala Ser Glu Ile Ile
    15                  20                  25

Tyr Ser Tyr Leu Ala Trp Tyr Gln Gln Lys Pro Gly Lys Ala Pro Lys
30                  35                  40                  45

Leu Leu Ile Tyr Asn Ala Lys Thr Leu Ala Asp Gly Val Pro Ser Arg
                50                  55                  60

Phe Ser Gly Ser Gly Ser Gly Thr Asp Phe Thr Phe Thr Ile Ser Ser
                65                  70                  75

Leu Gln Pro Glu Asp Ile Ala Thr Tyr Tyr Cys Gln His His Phe Gly
            80                  85                  90

Phe Pro Arg Thr Phe Gly Gln Gly Thr Lys Val Glu Ile Lys
        95                  100                 105
```

(2) INFORMATION FOR SEQ ID NO:74:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...38
        (D) OTHER INFORMATION: FTY1 sequence (xi) SEQUENCE DESCRIPTION: SEQ ID NO:74:

```
AGCGGTAGCG GTACCGACTA CACCTTCACC ATCAGCAG                          38
```

(2) INFORMATION FOR SEQ ID NO:75:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...38
        (D) OTHER INFORMATION: FTY2 sequence (xi) SEQUENCE DESCRIPTION: SEQ ID NO:75:

CTGCTGATGG TGAAGGTGTA GTCGGTACCG CTACCGCT          38

(2) INFORMATION FOR SEQ ID NO:76:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 1...378
        (D) OTHER INFORMATION:
        (A) NAME/KEY: mat_peptide
        (B) LOCATION: 61...378
        (D) OTHER INFORMATION:
        (A) NAME/KEY: Signal Sequence
        (B) LOCATION: 1...60
        (D) OTHER INFORMATION:

(xi) SEQUENCE DESCRIPTION: SEQ ID NO:76:

```
ATG GGA TGG AGC TGT ATC ATC CTC TTC TTG GTA GCA ACA GCT ACA GGT      48
Met Gly Trp Ser Cys Ile Ile Leu Phe Leu Val Ala Thr Ala Thr Gly
            -15                 -10                 -5

GTC CAC TCC GAC ATC CAG ATG ACC CAG AGC CCA AGC AGC CTG AGC GCC      96
Val His Ser Asp Ile Gln Met Thr Gln Ser Pro Ser Ser Leu Ser Ala
             1               5                  10

AGC GTA GGT GAC AGA GTG ACC ATC ACC TGT CGA GCA AGC GAG ATT ATT     144
Ser Val Gly Asp Arg Val Thr Ile Thr Cys Arg Ala Ser Glu Ile Ile
    15                  20                  25

TAC AGT TAT TTA GCA TGG TAC CAG CAG AAG CCA GGA AAG GCT CCA AAG     192
Tyr Ser Tyr Leu Ala Trp Tyr Gln Gln Lys Pro Gly Lys Ala Pro Lys
30                  35                  40                  45

CTG CTG ATC TAC AAT GCA AAA ACC TTA GCA GAT GGA GTG CCA AGC AGA     240
Leu Leu Ile Tyr Asn Ala Lys Thr Leu Ala Asp Gly Val Pro Ser Arg
                50                  55                  60

TTC AGC GGT AGC GGT AGC GGT ACC GAC TAC ACC TTC ACC ATC AGC AGC     288
Phe Ser Gly Ser Gly Ser Gly Thr Asp Tyr Thr Phe Thr Ile Ser Ser
            65                  70                  75

CTC CAG CCA GAG GAC ATC GCT ACC TAC TAC TGC CAA CAT CAT TTT GGT     336
Leu Gln Pro Glu Asp Ile Ala Thr Tyr Tyr Cys Gln His His Phe Gly
            80                  85                  90

TTT CCT CGG ACG TTC GGC CAA GGG ACC AAG GTC GAA ATC AAA C           379
Phe Pro Arg Thr Phe Gly Gln Gly Thr Lys Val Glu Ile Lys
            95                  100                 105
```

(2) INFORMATION FOR SEQ ID NO:77:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:77:

```
Met Gly Trp Ser Cys Ile Ile Leu Phe Leu Val Ala Thr Ala Thr Gly
            -15                 -10                 -5
```

Val His Ser Asp Ile Gln Met Thr Gln Ser Pro Ser Ser Leu Ser Ala
 1               5                  10                15

Ser Val Gly Asp Arg Val Thr Ile Thr Cys Arg Ala Ser Glu Ile Ile
             20                  25                  30

Tyr Ser Tyr Leu Ala Trp Tyr Gln Gln Lys Pro Gly Lys Ala Pro Lys
 30              35                  40                  45

Leu Leu Ile Tyr Asn Ala Lys Thr Leu Ala Asp Gly Val Pro Ser Arg
             50                  55                  60

Phe Ser Gly Ser Gly Ser Gly Thr Asp Tyr Thr Phe Thr Ile Ser Ser
             65                  70                  75

Leu Gln Pro Glu Asp Ile Ala Thr Tyr Tyr Cys Gln His His Phe Gly
         80                  85                  90

Phe Pro Arg Thr Phe Gly Gln Gly Thr Lys Val Glu Ile Lys
 95                 100                 105

(2) INFORMATION FOR SEQ ID NO:78:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...18
        (D) OTHER INFORMATION: EF1 sequence (xi) SEQUENCE DESCRIPTION: SEQ ID NO:78:

CAGACAGTGG TTCAAAGT                                                    18

(2) INFORMATION FOR SEQ ID NO:79:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...17
        (D) OTHER INFORMATION: HIP sequence (xi) SEQUENCE DESCRIPTION: SEQ ID NO:79:

GCCCCAAAGC CAAGGTC                                                     17

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: Other
        (B) LOCATION: 1...20
        (D) OTHER INFORMATION: KIP sequence (xi) SEQUENCE DESCRIPTION: SEQ ID NO:80:

AACTCAATGC TTTAGGCAAA                                                  20

(2) INFORMATION FOR SEQ ID NO:81:

(i) SEQUENCE CHARACTERISTICS:

(A) LENGTH: 11 amino acids
       (B) TYPE: amino acid
       (C) STRANDEDNESS: single
       (D) TOPOLOGY: linear (xi) SEQUENCE DESCRIPTION: SEQ ID NO:81:

Arg Ala Ser Glu Ile Ile Tyr Ser Tyr Leu Ala
1               5                  10

(2) INFORMATION FOR SEQ ID NO:82:

(i) SEQUENCE CHARACTERISTICS:
       (A) LENGTH: 7 amino acids
       (B) TYPE: amino acid
       (C) STRANDEDNESS: single
       (D) TOPOLOGY: linear (xi) SEQUENCE DESCRIPTION: SEQ ID NO:82:

Asn Ala Lys Thr Leu Ala Asp
1               5

(2) INFORMATION FOR SEQ ID NO:83:

(i) SEQUENCE CHARACTERISTICS:
       (A) LENGTH: 9 amino acids
       (B) TYPE: amino acid
       (C) STRANDEDNESS: single
       (D) TOPOLOGY: linear (xi) SEQUENCE DESCRIPTION: SEQ ID NO:83:

Gln His His Phe Gly Phe Pro Arg Thr
1               5

(2) INFORMATION FOR SEQ ID NO:84:

(i) SEQUENCE CHARACTERISTICS:
       (A) LENGTH: 5 amino acids
       (B) TYPE: amino acid
       (C) STRANDEDNESS: single
       (D) TOPOLOGY: linear (xi) SEQUENCE DESCRIPTION: SEQ ID NO:84:

Asp Tyr Tyr Leu Ser
1               5

(2) INFORMATION FOR SEQ ID NO:85:

(i) SEQUENCE CHARACTERISTICS:
       (A) LENGTH: 19 amino acids
       (B) TYPE: amino acid
       (C) STRANDEDNESS: single
       (D) TOPOLOGY: linear (xi) SEQUENCE DESCRIPTION: SEQ ID NO:85:

Leu Ile Arg Asn Lys Ala Asn Gly Tyr Thr Arg Glu Tyr Ser Ala Ser
1               5                  10                  15

Val Lys Gly (2) INFORMATION FOR SEQ ID NO:86:

(i) SEQUENCE CHARACTERISTICS:
       (A) LENGTH: 11 amino acids
       (B) TYPE: amino acid
       (C) STRANDEDNESS: single
       (D) TOPOLOGY: linear (xi) SEQUENCE DESCRIPTION: SEQ ID NO:86:

Glu Asn Tyr Arg Tyr Asp Val Glu Leu Ala Tyr (2) INFORMATION FOR SEQ ID NO:87:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:87:

```
Asp Ile Gln Met Thr Gln Ser Pro Ser Ser Leu Ser Ala Ser Val Gly
 1               5                  10                  15

Asp Arg Val Thr Ile Thr Cys
            20
```

(2) INFORMATION FOR SEQ ID NO:88:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:88:

```
Trp Tyr Gln Gln Lys Pro Gly Lys Ala Pro Lys Leu Leu Ile Tyr
 1               5                  10                  15
```

(2) INFORMATION FOR SEQ ID NO:89:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO:89:

```
Gly Val Pro Ser Arg Phe Ser Gly Ser Gly Ser Gly Thr Asp Phe Thr
 1               5                  10                  15

Phe Thr Ile Ser Ser Leu Gln Pro Glu Asp Ile Ala Thr Tyr Tyr Cys
            20                  25                  30
```

(2) INFORMATION FOR SEQ ID NO:90:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:90:

```
Phe Gly Gln Gly Thr Lys Val Glu Ile Lys
 1               5                  10
```

(2) INFORMATION FOR SEQ ID NO:91:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO:91:

```
Gly Val Pro Ser Arg Phe Ser Gly Ser Gly Ser Gly Thr Asp Tyr Thr
 1               5                  10                  15

Phe Thr Ile Ser Ser Leu Gln Pro Glu Asp Ile Ala Thr Tyr Tyr Cys
            20                  25                  30
```

(2) INFORMATION FOR SEQ ID NO:92:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:92:

Glu Val Gln Leu Leu Glu Ser Gly Gly Gly Leu Val Gln Pro Gly Gly
1              5                  10              15

Ser Leu Arg Leu Ser Cys Ala Ala Ser Gly Phe Thr Phe Ser
         20                25              30

(2) INFORMATION FOR SEQ ID NO:93:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:93:

Trp Val Arg Gln Ala Gln Gly Lys Gly Leu Glu Leu Val Gly
1              5                  10

(2) INFORMATION FOR SEQ ID NO:94:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO:94:

Arg Leu Thr Ile Ser Arg Glu Asp Ser Lys Asn Thr Leu Tyr Leu Gln
1              5                  10              15

Met Ser Ser Leu Lys Thr Glu Asp Leu Ala Val Tyr Tyr Cys Ala Arg
         20                25              30

(2) INFORMATION FOR SEQ ID NO:95:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:95:

Trp Gly Gln Gly Thr Leu Val Thr Val Ser Ser
1              5                  10

(2) INFORMATION FOR SEQ ID NO:96:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:96:

Trp Val Arg Gln Ala Gln Gly Lys Gly Leu Glu Trp Val Gly
1              5                  10

(2) INFORMATION FOR SEQ ID NO:97:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:97:

Trp Val Arg Gln Ala Pro Gly Lys Gly Leu Glu Leu Val Gly
 1               5                  10

(2) INFORMATION FOR SEQ ID NO:98:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:98:

Trp Val Arg Gln Ala Pro Gly Lys Gly Leu Glu Trp Val Gly
 1               5                  10

(2) INFORMATION FOR SEQ ID NO:99:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:99:

Trp Val Arg Gln Pro Pro Gly Lys Gly Leu Glu Trp Val Gly
 1               5                  10

(2) INFORMATION FOR SEQ ID NO:100:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:100:

Trp Val Arg Gln Ala Pro Gly Lys Ala Leu Glu Trp Val Gly
 1               5                  10

(2) INFORMATION FOR SEQ ID NO:101:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:101:

Trp Val Arg Gln Ala Pro Gly Lys Gly Leu Glu Trp Val Gly
 1               5                  10

(2) INFORMATION FOR SEQ ID NO:102:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO:102:

Arg Phe Thr Ile Ser Arg Glu Asp Ser Lys Asn Thr Leu Tyr Leu Gln
 1               5                  10                  15

```
Met Ser Ser Leu Lys Thr Glu Asp Leu Ala Val Tyr Tyr Cys Ala Arg
            20                  25                  30
```

(2) INFORMATION FOR SEQ ID NO:103:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:103:

```
Trp Val Arg Gln Ala Gln Gly Lys Gly Leu Glu Trp Val Gly
 1               5                  10
```

(2) INFORMATION FOR SEQ ID NO:104:

(i) SEQUENCE CHARACTERISTICS:
        (A) LENGTH: 80 amino acids
        (B) TYPE: amino acid
        (C) STRANDEDNESS: single
        (D) TOPOLOGY: linear (xi) SEQUENCE DESCRIPTION: SEQ ID NO:104:

```
Asp Ile Gln Met Thr Gln Ser Pro Ser Ser Leu Ser Ala Ser Val Gly
 1               5                  10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
            35                  40                  45

Ser Gly Thr Asp Phe Thr Phe Thr Ile Ser Ser Leu Gln Pro Glu Asp
 50                  55                  60

Ile Ala Thr Tyr Tyr Cys Phe Gly Gln Gly Thr Lys Val Glu Ile Lys
65                  70                  75                  80
```

(2) INFORMATION FOR SEQ ID NO:105:

(i) SEQUENCE CHARACTERISTICS:
        (A) LENGTH: 87 amino acids
        (B) TYPE: amino acid
        (C) STRANDEDNESS: single
        (D) TOPOLOGY: linear (xi) SEQUENCE DESCRIPTION: SEQ ID NO:105:

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Val
            20                  25                  30

Arg Gln Ala Gln Gly Lys Gly Leu Glu Leu Val Gly Arg Leu Thr Ile
            35                  40                  45

Ser Arg Glu Asp Ser Lys Asn Thr Leu Tyr Leu Gln Met Ser Ser Leu
 50                  55                  60

Lys Thr Glu Asp Leu Ala Val Tyr Tyr Cys Ala Arg Trp Gly Gln Gly
65                  70                  75                  80

Thr Leu Val Thr Val Ser Ser
                    85
```